(12) United States Patent
Yu et al.

(10) Patent No.: US 11,174,210 B2
(45) Date of Patent: Nov. 16, 2021

(54) COMPOUND, COATING COMPOSITION COMPRISING SAME, ORGANIC LIGHT-EMITTING DEVICE USING SAME AND METHOD FOR PREPARING SAME

(71) Applicant: LG CHEM, LTD., Seoul (KR)

(72) Inventors: Soyoung Yu, Daejeon (KR);
Sungkyoung Kang, Daejeon (KR);
Jaesoon Bae, Daejeon (KR); Kilsun Lee, Daejeon (KR); Donggu Lee, Daejeon (KR); Jaechol Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 305 days.

(21) Appl. No.: 16/341,380

(22) PCT Filed: May 18, 2018

(86) PCT No.: PCT/KR2018/005716
§ 371 (c)(1),
(2) Date: Apr. 11, 2019

(87) PCT Pub. No.: WO2018/230848
PCT Pub. Date: Dec. 20, 2018

(65) Prior Publication Data
US 2020/0055803 A1 Feb. 20, 2020

(30) Foreign Application Priority Data

Jun. 16, 2017 (KR) .................. 10-2017-0076688

(51) Int. Cl.
C07C 13/567 (2006.01)
C07D 209/58 (2006.01)
H01L 51/00 (2006.01)

(52) U.S. Cl.
CPC .......... *C07C 13/567* (2013.01); *C07D 209/58* (2013.01); *H01L 51/006* (2013.01); *H01L 51/0058* (2013.01); *H01L 51/0069* (2013.01); *H01L 51/0072* (2013.01)

(58) Field of Classification Search
None
See application file for complete search history.

(56) References Cited

FOREIGN PATENT DOCUMENTS

| EP | 3018120 A1 | 5/2016 |
|---|---|---|
| JP | 11-144875 A | 5/1999 |
| JP | 2017-514654 A | 6/2004 |
| JP | 2007-291064 A | 11/2007 |
| KR | 10-2012-0112277 A | 10/2012 |
| KR | 10-2017-0027250 A | 3/2017 |

OTHER PUBLICATIONS

Lengvinaite, et al.: "Cross-linkable fluorenyl-substituted aromatic amines for polymeric hole transporting networks", XP055588873, Reactive & Functional Polymers, Elsevier Ltd., vol. 71, No. 5, Mar. 5, 2011, pp. 574-578.

*Primary Examiner* — Jay Yang
(74) *Attorney, Agent, or Firm* — Dentons US LLP

(57) ABSTRACT

The present specification relates to a compound of Chemical Formula 1, a coating composition including the compound of Chemical Formula 1, an organic light emitting device using the same, and a method for manufacturing the same.

13 Claims, 7 Drawing Sheets

【FIG. 1】
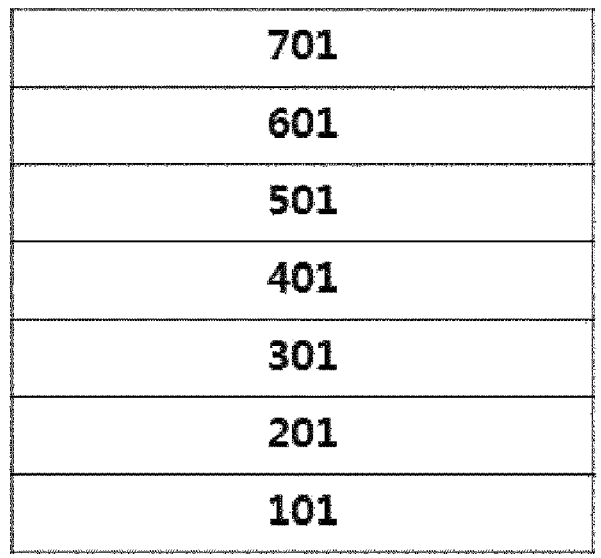
【FIG. 2】
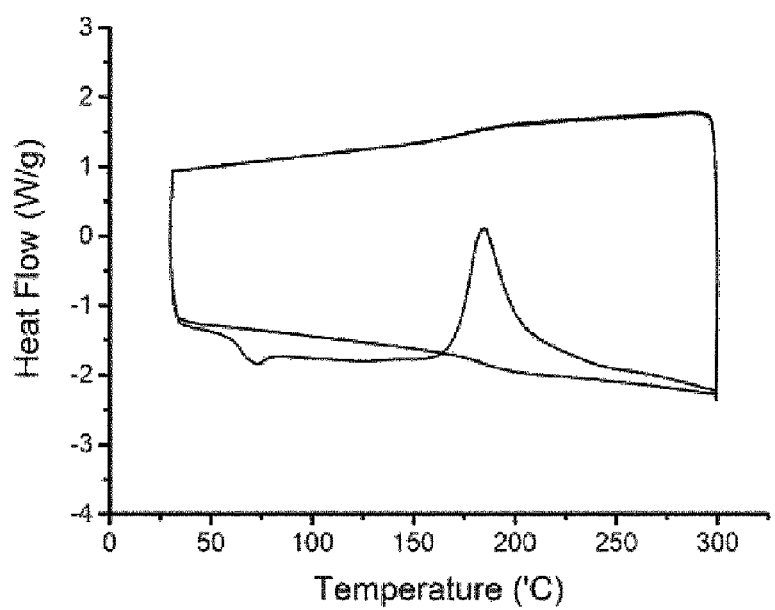

【FIG. 3】
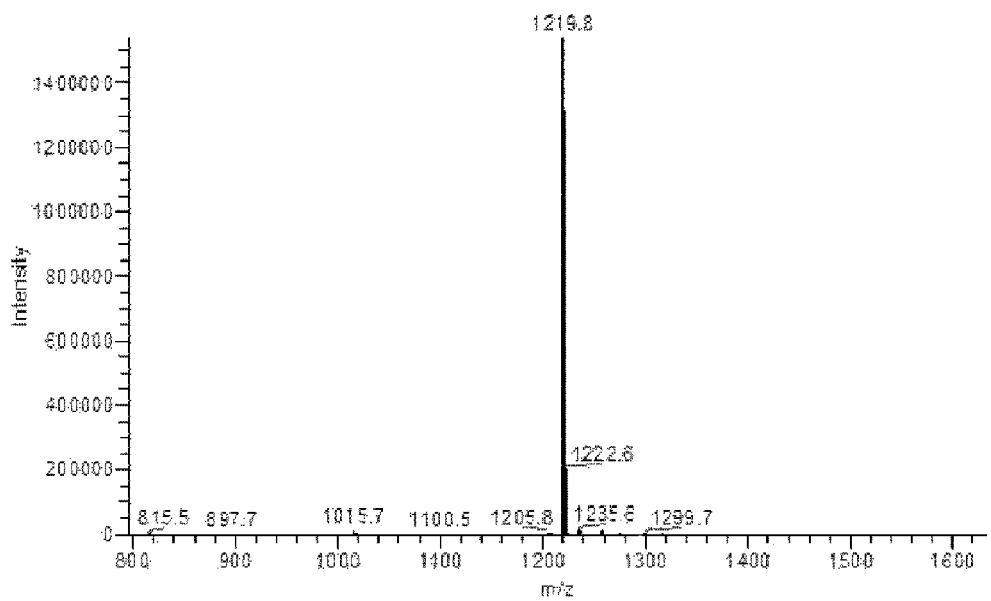
【FIG. 4】
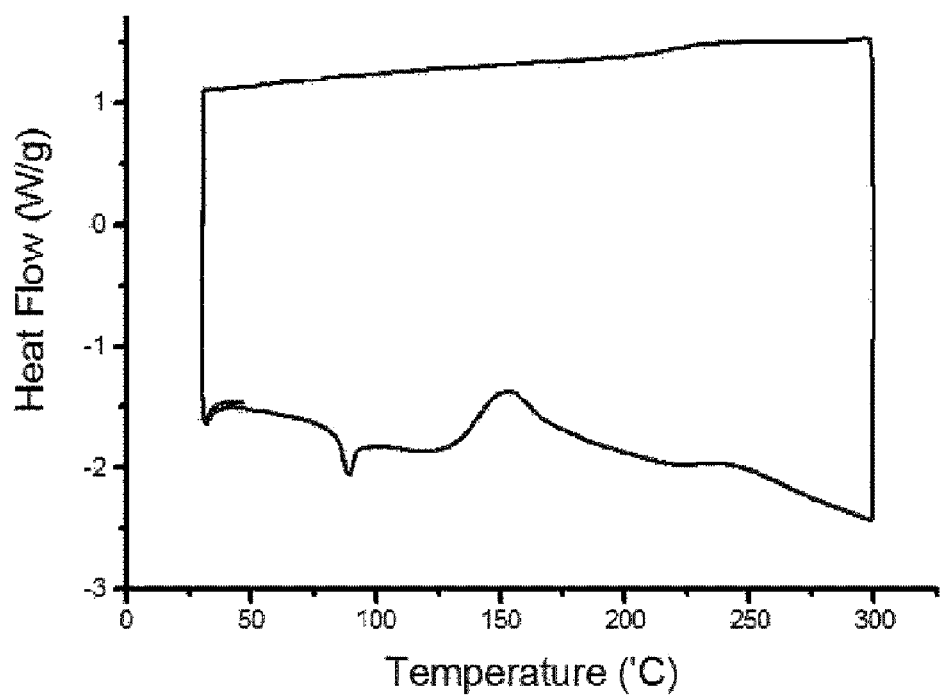

【FIG 5】
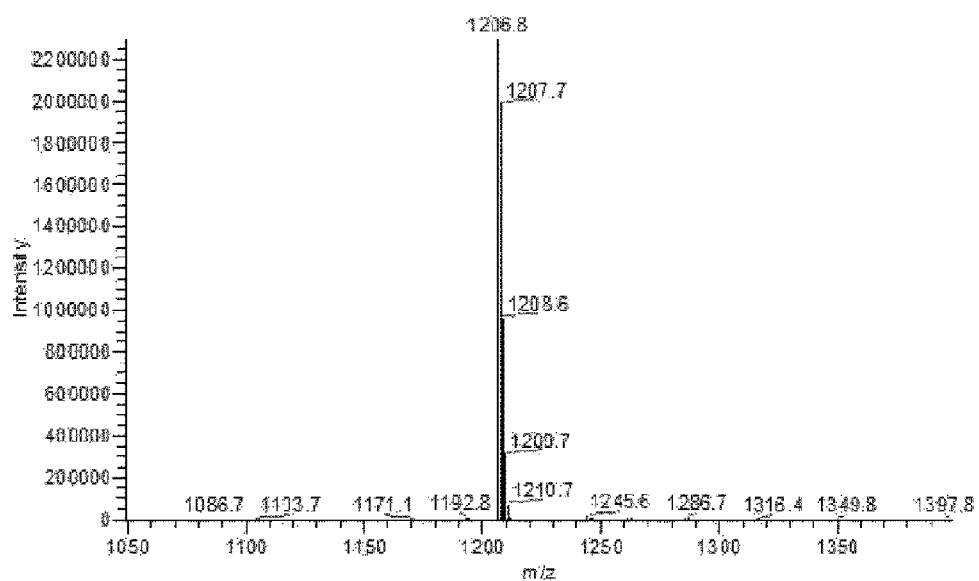
【FIG 6】
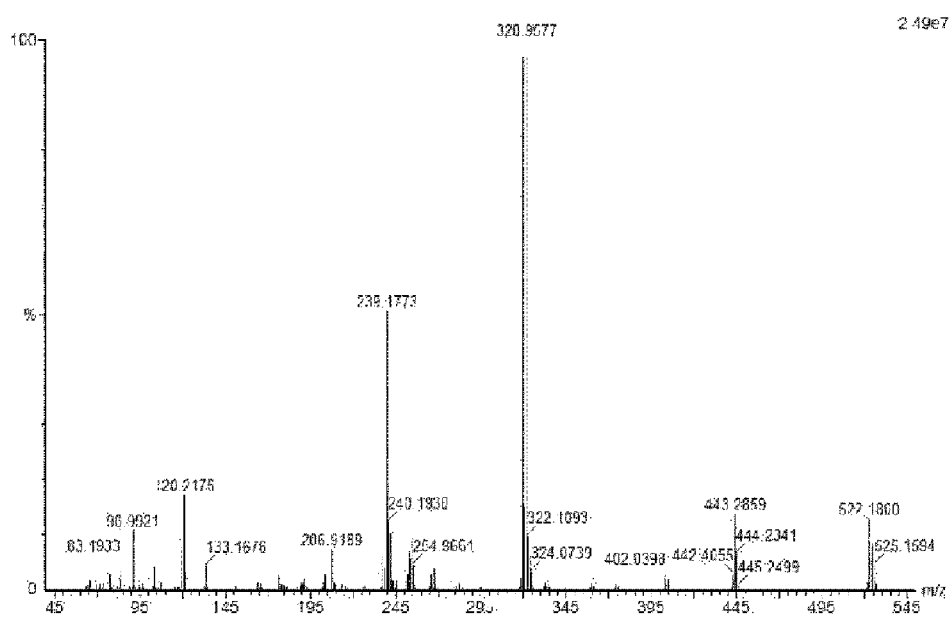

【FIG. 7】
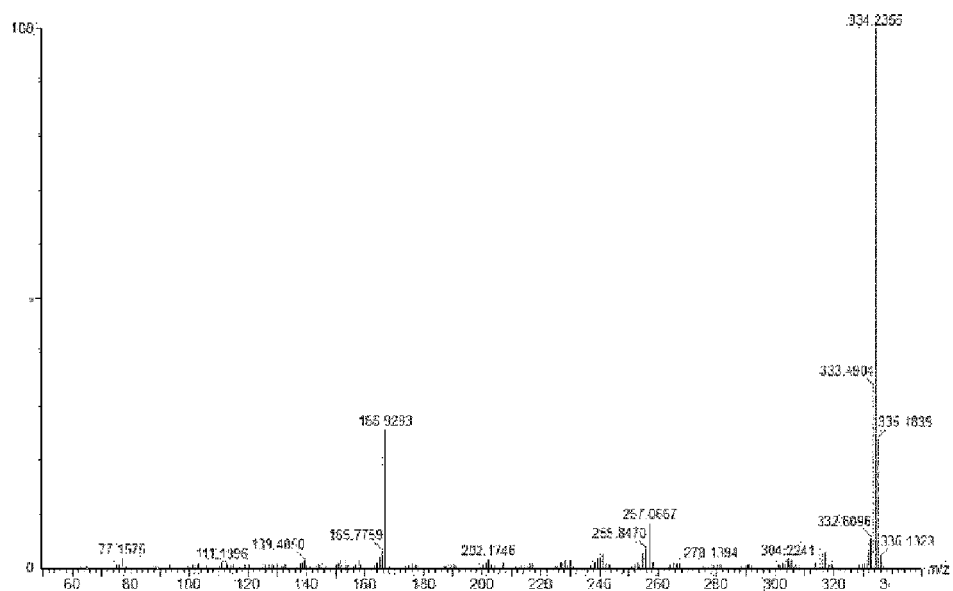
【FIG. 8】
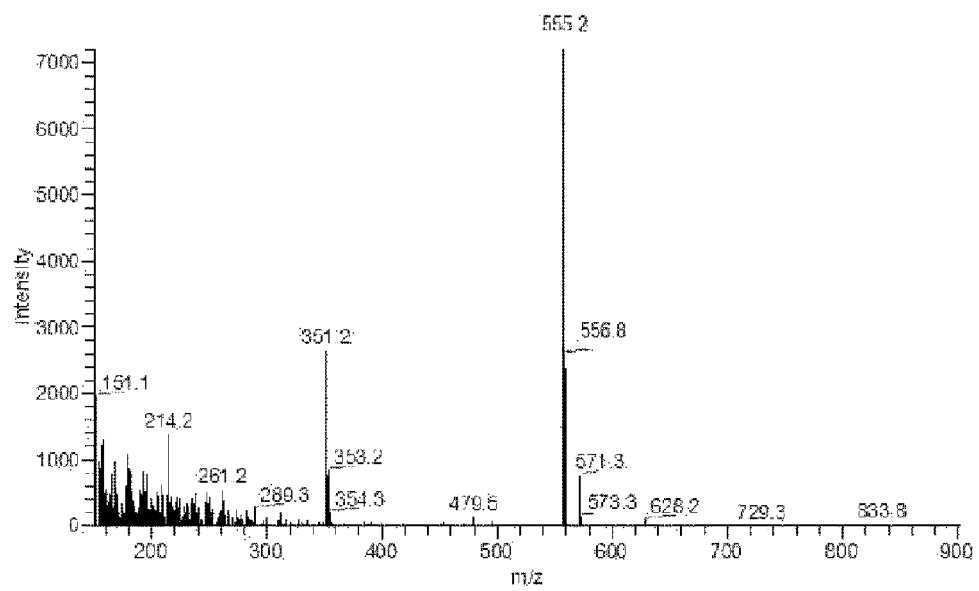

【FIG 9】
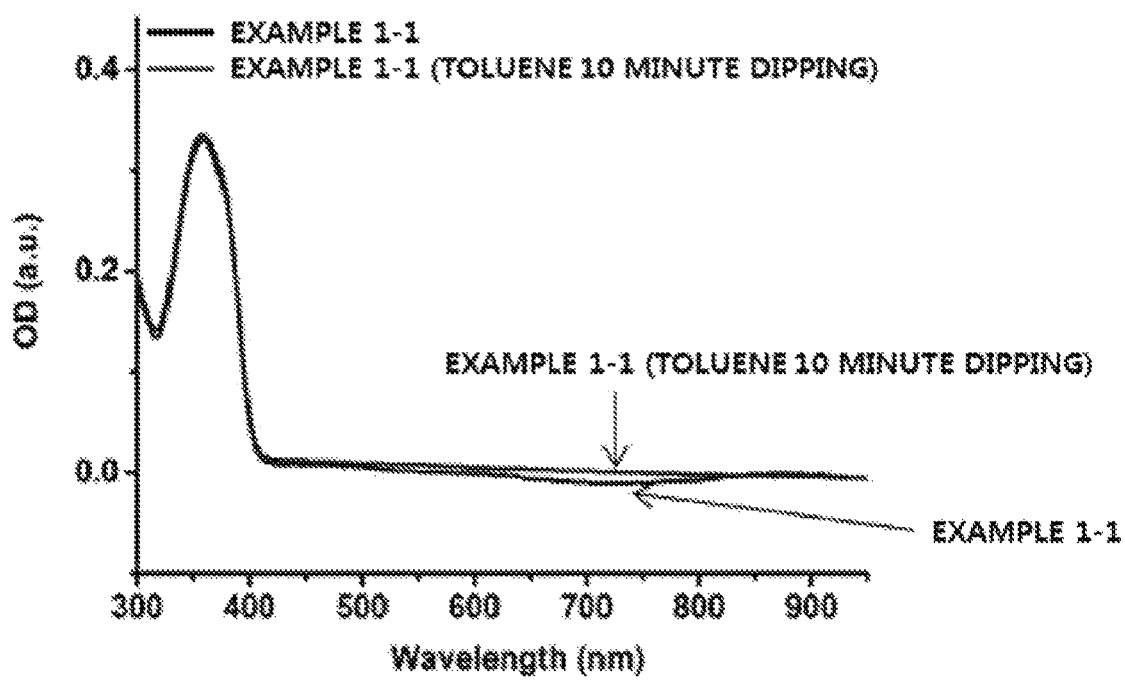
【FIG. 10】
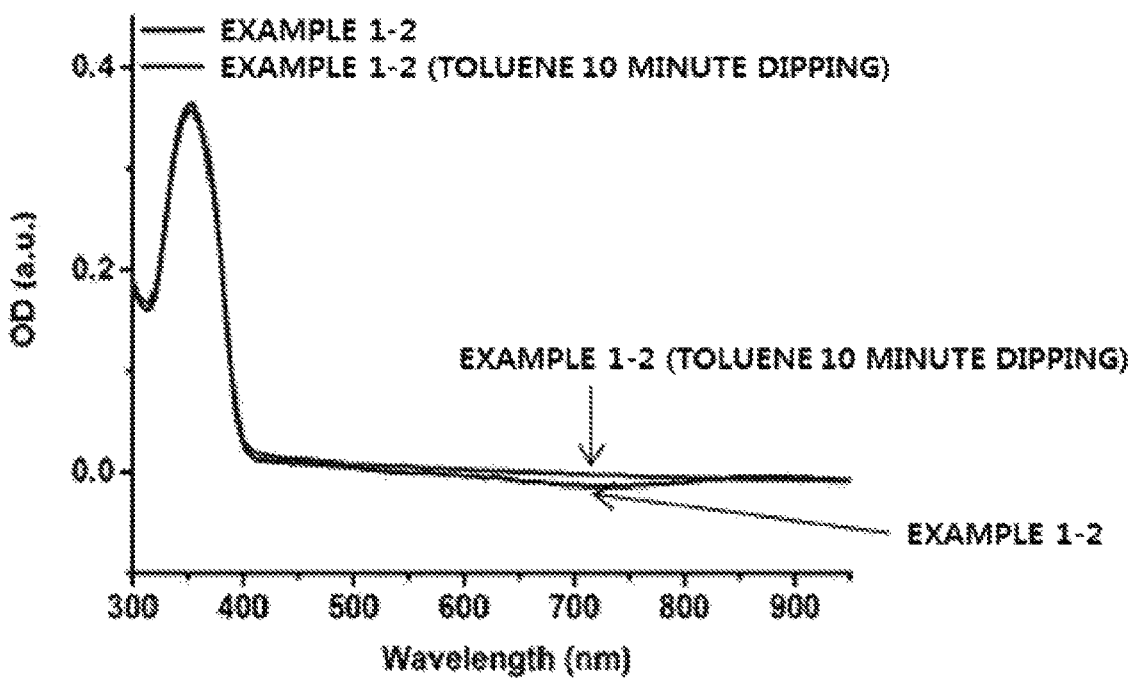

[FIG 11]
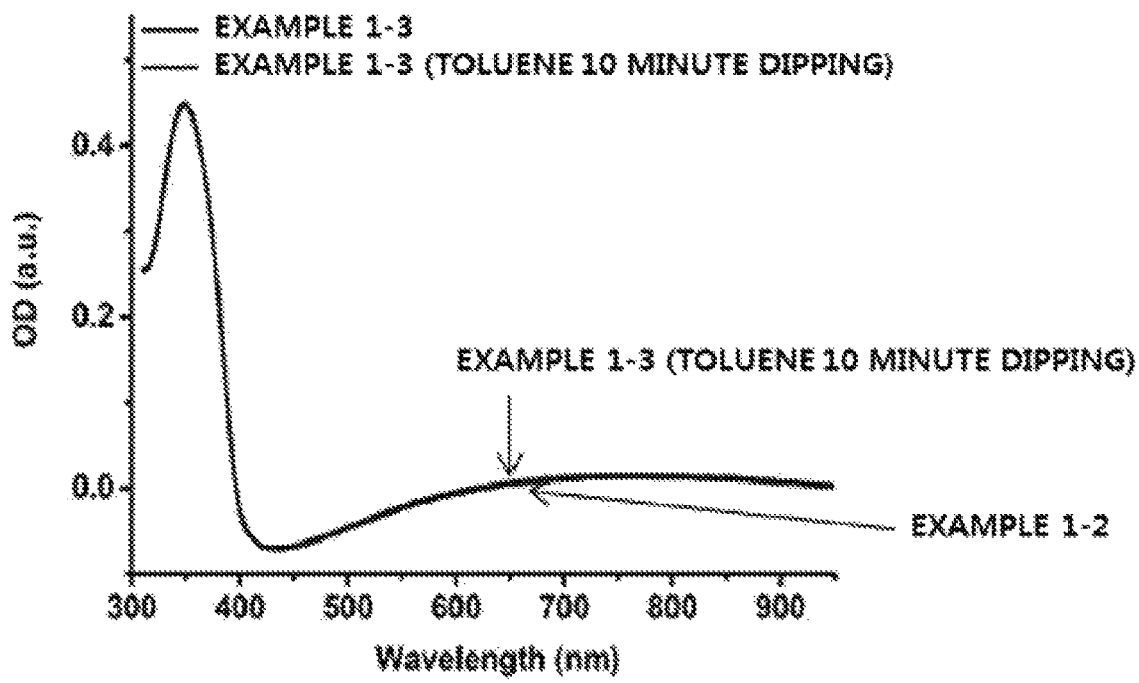
[FIG 12]
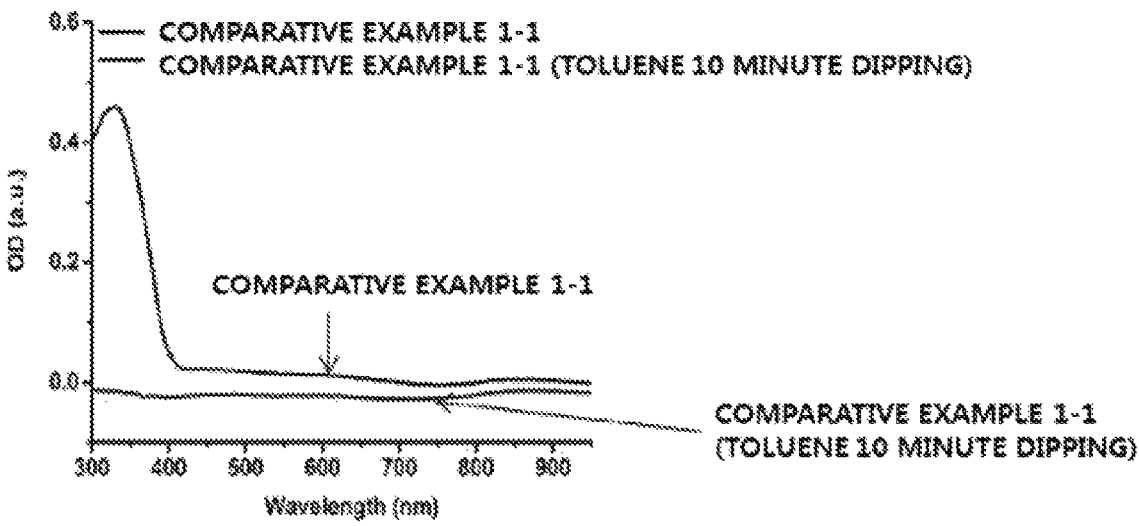

[FIG. 13]
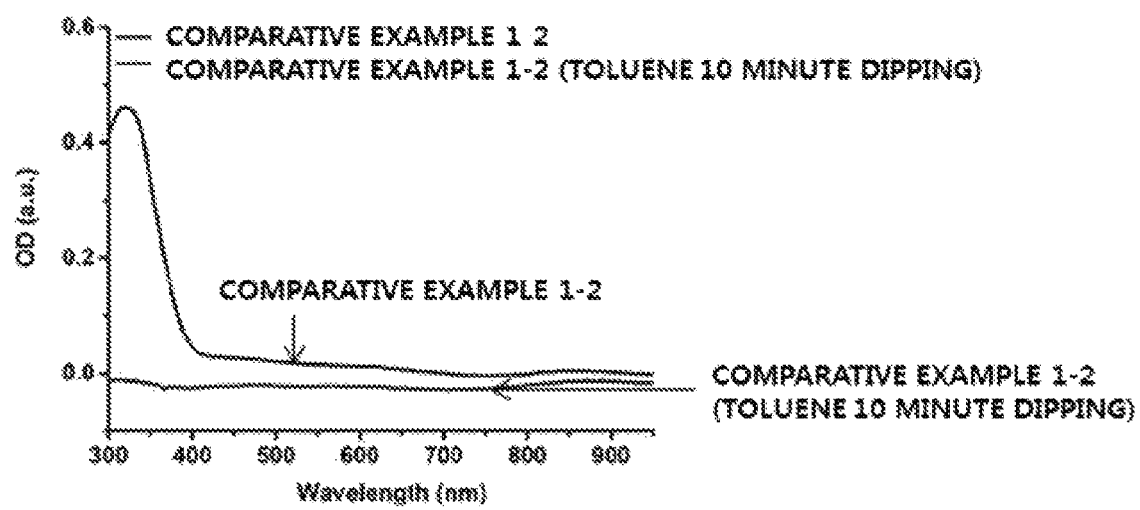

COMPOUND, COATING COMPOSITION COMPRISING SAME, ORGANIC LIGHT-EMITTING DEVICE USING SAME AND METHOD FOR PREPARING SAME

The present application is a National Phase entry, pursuant to 35 U.S.C. § 371, of International Application Serial No. PCT/KR2018/005716, filed May 18, 2018, and claims priority to and the benefit of Korean Patent Application No. 10-2017-0076688, filed with the Korean Intellectual Property Office on Jun. 16, 2017, the entire contents of which are incorporated herein by reference.

FIELD

The present specification relates to a compound, a coating composition including the compound, an organic light emitting device formed using the coating composition, and a method for manufacturing the same.

BACKGROUND

An organic light emission phenomenon is one example of converting current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic light emitting device using such a principle may be generally formed with a cathode, an anode, and an organic material layer placed therebetween, for example, an organic material layer including a hole injection layer, a hole transfer layer, a light emitting layer and an electron transfer layer.

A deposition process has been normally used in the art for manufacturing an organic light emitting device. However, manufacturing an organic light emitting device using a deposition process has a problem of high material loss, and in order to resolve such a problem, technologies for manufacturing a device through a solution process capable of increasing production efficiency with low material loss have been developed, and the development of materials usable in a solution process has been required.

Materials used in an organic light emitting device for a solution process need to have the following properties.

First, a storable homogeneous solution needs to be formed. Commercial materials for a deposition process have favorable crystallinity, and are not well-dissolved in a solution, or crystals are readily caught even when forming a solution. Therefore, a concentration gradient of the solution may change depending on the storage time, or the possibility of forming a defective device is high.

Second, layers going through a solution process need to have resistance to solvents and materials used in processes forming other layers, excellent current efficiency, and excellent lifetime properties, are required when manufacturing an organic light emitting device.

SUMMARY

The present specification is directed to providing a compound capable of being used in an organic light emitting device for a solution process, and an organic light emitting device including the same.

One embodiment of the present specification provides a compound represented by the following Chemical Formula 1.

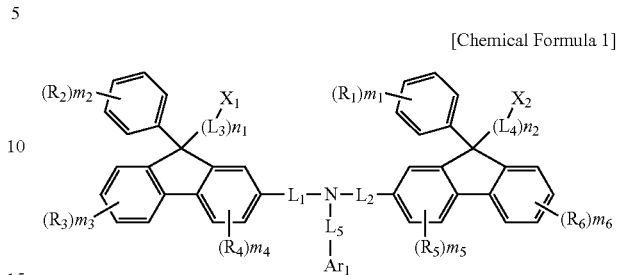

[Chemical Formula 1]

In Chemical Formula 1, $L_1$ and $L_2$ are the same as or different from each other, and each independently a direct bond; a substituted or unsubstituted arylene group; or a substituted or unsubstituted heteroarylene group, $L_3$ and $L_4$ are the same as or different from each other, and each independently a direct bond; or a substituted or unsubstituted alkylene group, $L_5$ is a direct bond; or a substituted or unsubstituted arylene group, $R_1$ to $R_6$ are the same as or different from each other, and each independently hydrogen; deuterium; a halogen group; a nitrile group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; a substituted or unsubstituted alkylamine group; a substituted or unsubstituted arylamine group; a substituted or unsubstituted heteroarylamine group; or a substituted or unsubstituted heteroaryl group, $Ar_1$ is hydrogen; a substituted or unsubstituted aryl group; a substituted or unsubstituted alkylamine group; a substituted or unsubstituted arylamine group; a substituted or unsubstituted heteroarylamine group; or a substituted or unsubstituted heteroaryl group, $X_1$ and $X_2$ are the same as or different from each other, and each independently a functional group crosslinkable by heat or light, $n_1$ and $n_2$ are each an integer of 0 to 12, $m_1$ and $m_2$ are each an integer of 0 to 5, $m_3$ and $m_6$ are each an integer of 0 to 4, and $m_4$ and $m_5$ are each an integer of 0 to 3.

One embodiment of the present specification provides a coating composition including the compound of Chemical Formula 1.

In addition, one embodiment of the present specification provides an organic light emitting device including a cathode; an anode; and one or more organic material layers provided between the cathode and the anode, wherein one or more layers of the organic material layers include a cured material of the coating composition, and the cured material of the coating composition is in a cured state by heat treating or light treating the coating composition.

Lastly, one embodiment of the present specification provides a method for manufacturing an organic light emitting device including preparing a substrate; forming a cathode or an anode on the substrate; forming one or more organic material layers on the cathode or the anode; and forming an anode or a cathode on the organic material layer, wherein the forming of organic material layers includes forming one or more organic material layers using the coating composition.

A compound according to one embodiment of the present disclosure can be prepared using a solution process, and therefore, large area devices can be manufactured. The compound can be used as a material of an organic material layer of an organic light emitting device. The resulting device exhibits low driving voltage, high light emission efficiency, and long service lifetime properties.

In addition, by including a functional group crosslinkable by heat or light, and introducing an alkyl group to which one arylene group and a curing group bond to the number 9 carbon of fluorene, a compound according to one embodiment of the present disclosure lowers curing temperature by increasing solubility and amorphous properties of the compound, and as a result, a thin film having excellent solvent resistance is obtained.

BRIEF DESCRIPTION OF THE DRAWING FIGURES

FIG. 1 is a diagram illustrating an organic light emitting device according to one embodiment of the present specification.

FIG. 2 shows a graph measuring Compound 1-1 using a differential scanning calorimeter (DSC).

FIG. 3 shows MS data of Compound 1-1.

FIG. 4 shows a graph measuring Compound 1-3 using a differential scanning calorimeter (DSC).

FIG. 5 shows MS data of Compound 1-3.

FIG. 6 shows an MS graph of Intermediate 1.

FIG. 7 shows an MS graph of Intermediate 2.

FIG. 8 shows an MS graph of Intermediate 3.

FIG. 9 is a diagram showing a UV spectrum of a thin film prepared in Example 1-1.

FIG. 10 is a diagram showing a UV spectrum of a thin film prepared in Example 1-2.

FIG. 11 is a diagram showing a UV spectrum of a thin film prepared in Example 1-3.

FIG. 12 is a diagram showing a UV spectrum of a thin film prepared in Comparative Example 2-1.

FIG. 13 is a diagram showing a UV spectrum of a thin film prepared in Comparative Example 2-2.

101: Substrate

201: Anode

301: Hole Injection Layer

401: Hole Transfer Layer

501: Light Emitting Layer

601: Electron Injection Layer

701: Cathode

DETAILED DESCRIPTION

Hereinafter, the present specification will be described in detail.

One embodiment of the present specification provides a compound represented by the following Chemical Formula 1.

[Chemical Formula 1]

In Chemical Formula 1, $L_1$ and $L_2$ are the same as or different from each other, and each independently a direct bond; a substituted or unsubstituted arylene group; or a substituted or unsubstituted heteroarylene group, $L_3$ and $L_4$ are the same as or different from each other, and each independently a direct bond; or a substituted or unsubstituted alkylene group, $L_5$ is a direct bond; or a substituted or unsubstituted arylene group, $R_1$ to $R_6$ are the same as or different from each other, and each independently hydrogen; deuterium; a halogen group; a nitrile group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; a substituted or unsubstituted alkylamine group; a substituted or unsubstituted arylamine group; a substituted or unsubstituted heteroarylamine group; a substituted or unsubstituted arylheteroarylamine group; or a substituted or unsubstituted heteroaryl group, $Ar_1$ is hydrogen; a substituted or unsubstituted aryl group; a substituted or unsubstituted alkylamine group; a substituted or unsubstituted arylamine group; a substituted or unsubstituted heteroarylamine group; a substituted or unsubstituted arylheteroarylamine group; or a substituted or unsubstituted heteroaryl group, $X_1$ and $X_2$ are the same as or different from each other, and each independently a functional group crosslinkable by heat or light, $n_1$ and $n_2$ are each an integer of 0 to 12, $m_1$ and $m_2$ are each an integer of 0 to 5, $m_3$ and $m_6$ are each an integer of 0 to 4, and $m_4$ and $m_5$ are each an integer of 0 to 3.

By using the compound according to one embodiment of the present disclosure, a coating composition having excellent solubility may be prepared, and when forming a thin film using the coating composition, a thin film having high uniformity and having excellent solvent resistance may be prepared. In addition, when manufacturing an organic light emitting device including the compound, an effect of excellent light emission efficiency is obtained.

In the present specification, a description of a certain member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated to the contrary.

In the present specification, the term "combination thereof" included in a Markush-type expression means mixing or combining two or more selected from the group consisting of constituents described in the Markush-type expression, and means including one or more selected from the group consisting of the constituents.

In one embodiment of the present specification, the compound of Chemical Formula 1 preferably includes compounds having solubility for proper organic solvents.

In the present specification, the "functional group crosslinkable by heat or light" may mean a reactive substituent crosslinking compounds by being exposed to heat or light. The crosslinkage may be produced by linking radicals produced while carbon-carbon multiple bonds or cyclic structures are disintegrated by heat treatment or light irradiation.

In one embodiment of the present specification, an organic light emitting device may be manufactured using a solution coating method with the compound including the functional group crosslinkable by heat or light, which is economically effective in terms of time and costs.

In addition, when forming a coating layer using a coating composition including the compound including the functional group crosslinkable by heat or light, the functional group crosslinkable by heat or light forms crosslinkage by heat or light, and therefore, fluorene derivatives included in the coating composition being washed away by a solvent may be prevented when laminating additional layers on the top of the coating layer, and additional layers may be laminated on the top while maintaining the coating layer.

In addition, forming a coating layer through the functional group crosslinkable by heat or light forming crosslinkage is effective in increasing chemical resistance of the coating layer for a solvent, and having a high film retention rate.

Furthermore, with the compound according to one embodiment of the present specification, an organic light emitting device may be manufactured using a solution coating method, and therefore, large area devices may be manufactured.

The compound forming crosslinkage through heat treatment or light irradiation according to one embodiment of the present specification is provided in a thin film form in an organic light emitting device by a plurality of the compounds of Chemical Formula 1 being crosslinked, which is effective in obtaining excellent thermal stability.

In addition, the compound according to one embodiment of the present specification includes an amine structure in the core structure, and therefore, may have proper energy level and bandgap as a hole injection, hole transfer or light emitting material in an organic light emitting device. The proper energy level and bandgap may also be finely adjusted by controlling substituents of the compound of Chemical Formula 1 according to one embodiment of the present specification, and by enhancing interfacial properties between organic materials, an organic light emitting device having low driving voltage and high light emission efficiency may be provided.

Hereinafter, substituents of the present specification will be described in detail.

In the present specification,

means a site bonding to other substituents or bonding sites.

The term "substitution" in the present specification means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of deuterium; a halogen group; a nitrile group; a hydroxyl group; a silyl group; a boron group; an alkyl group; a cycloalkyl group; an alkoxy group; an alkenyl group; an aryl group; an alkylamine group; an arylamine group; a heteroarylamine group; an arylheteroarylamine group; and a heterocyclic group, or being substituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, the halogen group is fluorine (F), chlorine (Cl), bromine (Br) or iodine (I).

In the present specification, the silyl group may be represented by a chemical formula of $—SiR_aR_bR_c$, and $R_a$, $R_b$ and $R_c$ may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by a chemical formula of $—BR_aR_b$, and $R_a$ and $R_b$ may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms may be from 1 to 30, and according to one embodiment, the number of carbon atoms of the alkyl group may be from 1 to 20. According to another embodiment, the number of carbon atoms of the alkyl group is from 1 to 10. Specific examples of the alkyl group may include a methyl group, an ethyl group, a propyl group, an isopropyl group, a butyl group, an isobutyl group, a tert-butyl group, a sec-butyl group, a 1-methyl-butyl group, a 1-ethyl-butyl group, a pentyl group, an isopentyl group, a neopentyl group, a tert-pentyl group, a 1-methylpentyl group, a 2-methylpentyl group, a 4-methyl-2-pentyl group, a hexyl group, an isohexyl group, a 4-methylhexyl group, a 5-methylhexyl group, a heptyl group and the like, but are not limited thereto.

In the present specification, the cycloalkyl group is not particularly limited, but may have 3 to 60 carbon atoms, and according to one embodiment, the number of carbon atoms of the cycloalkyl group is from 3 to 40. According to another embodiment, the number of carbon atoms of the cycloalkyl group is from 3 to 20. Specific examples of the cycloalkyl group may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may be linear, branched or cyclic. The number of carbon atoms of the alkoxy group is not particularly limited, but may be from 1 to 20. Specific examples of the alkoxy group may include a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, an 2-ethylbutyloxy group, an n-octyloxy group, an n-nonyloxy group, an n-decyloxy group, a benzyloxy group, a p-methylbenzyloxy group and the like, but are not limited thereto.

In the present specification, the alkenyl group may be linear or branched, and although not particularly limited thereto, the number of carbon atoms may be from 2 to 30, and according to one embodiment, the number of carbon atoms of the alkenyl group may be from 2 to 20. Specific examples of the alkenyl group may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the aryl group is not particularly limited, but may have 6 to 60 carbon atoms, and may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the polycyclic aryl group may include a naphthyl group, an anthracenyl group, a phenanthrenyl group, a pyrenyl group, a perylenyl group, a triphenyl group, a chrysenyl group, a fluorenyl group and the like, but are not limited thereto.

In the present specification, the fluorenyl group may be substituted, and two substituents may bond to each other to form a spiro structure.

When the fluorenyl group is substituted, spirofluorenyl groups such as

and

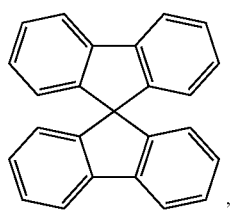 [SMILES: c1ccc2c(c1)-c1ccccc1C21c2ccccc2-c2ccccc21]

, and substituted fluorenyl groups such as

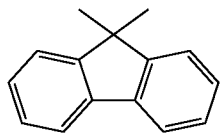

(9,9-dimethylfluorenyl group) and

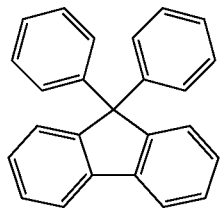 [SMILES: c1ccc(C2(c3ccccc3)c3ccccc3-c3ccccc32)cc1]

(9,9-diphenylfluorenyl group) may be included. However, the structure is not limited thereto.

In the present specification, the heteroaryl group is a group including one or more atoms that are not carbon, that is, heteroatoms, and specifically, the heteroatom may include one or more atoms selected from the group consisting of O, N, Se, Si, S and the like. The number of carbon atoms of the heteroaryl group is not particularly limited, but may be from 2 to 60, and according to one embodiment, the number of carbon atoms may be from 2 to 30. According to another embodiment, the number of carbon atoms may be from 2 to 20. Specific examples of the heterocyclic group may include a thiophene group, a furan group, a pyrrole group, a pyrimidyl group, a pyridazinyl group, an oxazole group, a pyrazole group, a triazinyl group, an indole group, a carbazole group, a dibenzofuranyl group, a dibenzothiophenyl group or the like, but are not limited thereto.

In the present specification, the number of carbon atoms of the alkylamine group is not particularly limited, but is preferably from 1 to 40. Specific examples of the alkylamine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include monocyclic aryl groups, polycyclic aryl groups, or both monocyclic aryl groups and polycyclic aryl groups.

Specific examples of the arylamine group may include phenylamine, naphthylamine, biphenylamine, a dibiphenylamine group, a 9,9-dimethylfluorenylbiphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a ditolylamine group, a phenyltolylamine group, carbazole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a polycyclic heterocyclic group. The heteroarylamine group including two or more heterocyclic groups may include monocyclic heterocyclic groups, polycyclic heterocyclic groups, or both monocyclic heterocyclic groups and polycyclic heterocyclic groups.

In the present specification, descriptions of the aryl group provided above may be applied to the aryl group in the arylheteroarylamine group.

In the present specification, descriptions of the aryl group provided above apply to the arylene group except for being divalent.

In the present specification, descriptions of the heteroaryl group provided above apply to the heteroarylene group except for being divalent.

In the present specification, descriptions of the alkyl group provided above apply to the alkylene group except for being divalent.

In one embodiment of the present specification, $X_1$ to $X_6$ are the same as or different from each other, and each independently a functional group crosslinkable by heat or light.

In one embodiment of the present specification, the functional group crosslinkable by heat or light is any one of the following structures.

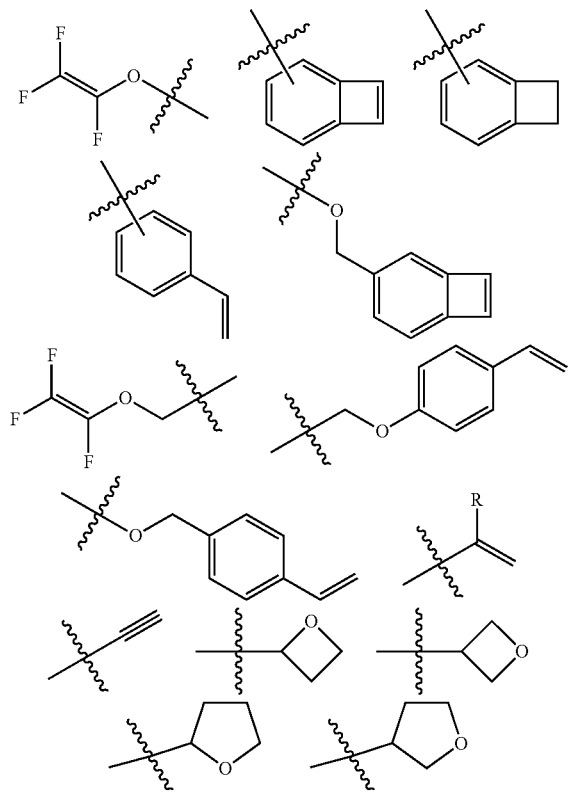

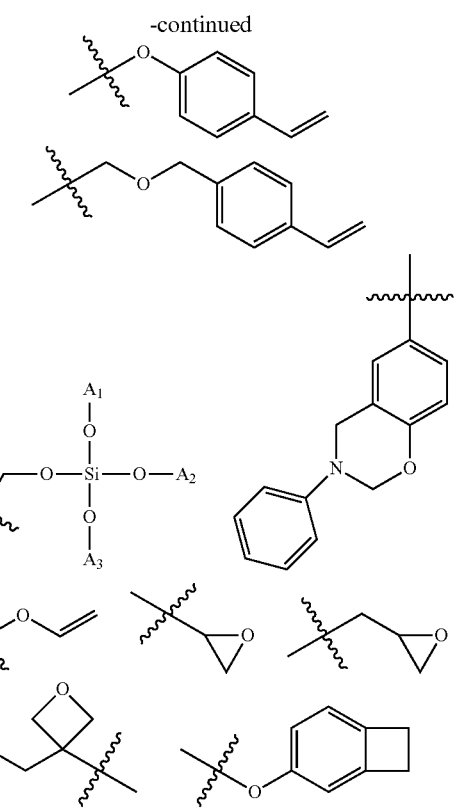

In these structures,

R is hydrogen; or a substituted or unsubstituted alkyl group, $A_1$ to $A_3$ are the same as or different from each other, and each independently a substituted or unsubstituted alkyl group having 1 to 6 carbon atoms.

In one embodiment, R is hydrogen; or a substituted or unsubstituted alkyl group having 1 to 30 carbon atoms.

In another embodiment, R is hydrogen; or a substituted or unsubstituted alkyl group having 1 to 20 carbon atoms.

According to another embodiment, R is hydrogen; a substituted or unsubstituted methyl group; a substituted or unsubstituted ethyl group; a substituted or unsubstituted propyl group; a substituted or unsubstituted isopropyl group; a substituted or unsubstituted butyl group; or a substituted or unsubstituted tert-butyl group.

In another embodiment, R is hydrogen; a methyl group; an ethyl group; a propyl group; an isopropyl group; a butyl group; or a tert-butyl group.

According to another embodiment, R is hydrogen.

In one embodiment of the present specification, $A_1$ to $A_3$ are the same as or different from each other, and each independently a substituted or unsubstituted methyl group; a substituted or unsubstituted ethyl group; a substituted or unsubstituted propyl group; a substituted or unsubstituted isopropyl group; a substituted or unsubstituted butyl group; a substituted or unsubstituted tert-butyl group; a substituted or unsubstituted pentyl group; or a substituted or unsubstituted hexyl group.

In another embodiment, $A_1$ to $A_3$ are the same as or different from each other, and each independently a methyl group; an ethyl group; a propyl group; an isopropyl group; a butyl group; a tert-butyl group; a pentyl group; or a hexyl group.

In one embodiment of the present specification, $L_1$ and $L_2$ are the same as or different from each other, and each independently a direct bond; a substituted or unsubstituted arylene group having 6 to 60 carbon atoms; or a substituted or unsubstituted heteroarylene group having 2 to 60 carbon atoms.

In another embodiment, $L_1$ and $L_2$ are the same as or different from each other, and each independently a direct bond; a substituted or unsubstituted arylene group having 6 to carbon atoms; or a substituted or unsubstituted heteroarylene group having 2 to 30 carbon atoms.

In another embodiment, $L_1$ and $L_2$ are the same as or different from each other, and each independently a direct bond or a substituted or unsubstituted arylene group having 6 to 30 carbon atoms.

In another embodiment, $L_1$ and $L_2$ are the same as or different from each other, and each independently a direct bond; a substituted or unsubstituted phenylene group; a substituted or unsubstituted biphenylylene group; or a substituted or unsubstituted naphthylene group.

According to another embodiment, $L_1$ and $L_2$ are the same as or different from each other, and each independently a direct bond; a phenylene group; a biphenylylene group; or a naphthylene group.

In another embodiment, $L_1$ and $L_2$ are the same as or different from each other, and each independently a direct bond; or a substituted or unsubstituted phenylene group.

According to another embodiment, $L_1$ and $L_2$ are the same as or different from each other, and each independently a direct bond or a phenylene group.

In another embodiment, $L_1$ and $L_2$ are a direct bond.

In another embodiment, $L_1$ and $L_2$ are a phenylene group.

In one embodiment of the present specification, $L_3$ and $L_4$ are the same as or different from each other, and each independently a direct bond; or a substituted or unsubstituted alkylene group having 1 to 30 carbon atoms.

According to another embodiment, $L_3$ and $L_4$ are the same as or different from each other, and each independently a direct bond; or a substituted or unsubstituted alkylene group having 1 to 20 carbon atoms.

In another embodiment, $L_3$ and $L_4$ are the same as or different from each other, and each independently a direct bond; or a substituted or unsubstituted alkylene group having 1 to 12 carbon atoms.

According to another embodiment, $L_3$ and $L_4$ are the same as or different from each other, and each independently a direct bond; a substituted or unsubstituted methylene group; a substituted or unsubstituted ethylene group; a substituted or unsubstituted propylene group; a substituted or unsubstituted butylene group; a substituted or unsubstituted pentylene group; or a substituted or unsubstituted hexylene group.

According to another embodiment, $L_3$ and $L_4$ are the same as or different from each other, and each independently a direct bond; a methylene group; an ethylene group; a propylene group; a butylene group; a pentylene group; or a hexylene group.

In another embodiment, $L_3$ and $L_4$ are a methylene group.

In one embodiment of the present specification, $n_1$ and $n_2$ are each an integer of 0 to 12.

In another embodiment, $n_1$ and $n_2$ are each an integer of 1 to 12.

According to another embodiment, $n_1$ and $n_2$ are each an integer of 0 to 6.

In another embodiment, $n_1$ and $n_2$ are each an integer of 1 to 6.

In one embodiment of the present specification, $L_3$ and $L_4$ are a methylene group, and $n_1$ and $n_2$ are each an integer of 1 to 12.

In another embodiment, $L_3$ and $L_4$ are a methylene group, and $n_1$ and $n_2$ are each an integer of 1 to 6.

In one embodiment of the present specification, $L_5$ is a direct bond; or a substituted or unsubstituted arylene group having 6 to 60 carbon atoms.

According to another embodiment, $L_5$ is a direct bond; or a substituted or unsubstituted arylene group having 6 to 30 carbon atoms.

In another embodiment, $L_5$ is a direct bond; or a substituted or unsubstituted arylene group having 6 to 20 carbon atoms.

According to another embodiment, $L_5$ is a direct bond; a substituted or unsubstituted phenylene group; a substituted or unsubstituted biphenylylene group; a substituted or unsubstituted fluorenylene group; a substituted or unsubstituted terphenylene group; or a substituted or unsubstituted naphthylene group.

In another embodiment, $L_5$ is a direct bond; a substituted or unsubstituted phenylene group; a substituted or unsubstituted biphenylylene group; or a substituted or unsubstituted fluorenylene group.

In another embodiment, $L_5$ is a direct bond; a phenylene group unsubstituted or substituted with an alkyl group; a biphenylylene group unsubstituted or substituted with an alkyl group; or a fluorenylene group unsubstituted or substituted with an alkyl group.

According to another embodiment, $L_5$ is a direct bond; a phenylene group unsubstituted or substituted with a methyl group or an ethyl group; a biphenylylene group unsubstituted or substituted with a methyl group or an ethyl group; or a fluorenylene group unsubstituted or substituted with a methyl group or an ethyl group.

In another embodiment, $L_5$ is a direct bond; a phenylene group; a biphenylylene group; or a 9,9-dimethylfluorenylene group.

In one embodiment of the present specification, $R_1$ to $R_6$ are the same as or different from each other, and each independently hydrogen; deuterium; a halogen group; a silyl group; a boron group; a substituted or unsubstituted alkyl group; a substituted or unsubstituted aryl group; or a substituted or unsubstituted heteroaryl group.

In another embodiment, $R_1$ to $R_6$ are the same as or different from each other, and each independently a halogen group; a silyl group; a boron group; a substituted or unsubstituted alkyl group having 1 to 30 carbon atoms; a substituted or unsubstituted aryl group having 6 to 60 carbon atoms; or a substituted or unsubstituted heteroaryl group having 2 to 60 carbon atoms.

According to another embodiment, $R_1$ to $R_6$ are the same as or different from each other, and each independently hydrogen; deuterium; a halogen group; a silyl group; a boron group; a substituted or unsubstituted alkyl group having 1 to 20 carbon atoms; a substituted or unsubstituted aryl group having 6 to 30 carbon atoms; or a substituted or unsubstituted heteroaryl group having 2 to 30 carbon atoms.

According to another embodiment, $R_1$ to $R_6$ are the same as or different from each other, and each independently hydrogen; deuterium; a halogen group; a silyl group; a boron group; a substituted or unsubstituted alkyl group having 1 to 10 carbon atoms; a substituted or unsubstituted aryl group having 6 to 20 carbon atoms; or a substituted or unsubstituted heteroaryl group having 2 to 20 carbon atoms.

In another embodiment, $R_1$ to $R_6$ are the same as or different from each other, and each independently hydrogen; deuterium; a halogen group; a silyl group; a boron group; a substituted or unsubstituted methyl group; a substituted or unsubstituted ethyl group; a substituted or unsubstituted propyl group; a substituted or unsubstituted isopropyl group; a substituted or unsubstituted butyl group; a substituted or unsubstituted t-butyl group; a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted carbazole group; a substituted or unsubstituted dibenzofuranyl group; or a substituted or unsubstituted dibenzothiophenyl group.

According to another embodiment, $R_1$ to $R_6$ are the same as or different from each other, and each independently hydrogen; deuterium; a halogen group; a trimethylsilyl group; a trimethylboron group; a methyl group; an ethyl group; a propyl group; an isopropyl group; a butyl group; a t-butyl group; a phenyl group; a biphenyl group; a terphenyl group; a naphthyl group; a 9,9-dimethylfluorenyl group; a 9,9-diphenylfluorenyl group; a carbazole group; an N-phenylcarbazole group; a dibenzofuranyl group; or a dibenzothiophenyl group.

In another embodiment, $R_1$ to $R_6$ are hydrogen.

In one embodiment of the present specification, $m_1$ and $m_2$ are each an integer of 0 to 5.

In another embodiment, $m_1$ and $m_2$ are each an integer of 1 to 5.

In one embodiment of the present specification, $m_3$ and $m_6$ are each an integer of 0 to 4.

In another embodiment, $m_3$ and $m_6$ are each an integer of 1 to 4.

In one embodiment of the present specification, $m_4$ and $m_5$ are each an integer of 0 to 3.

In another embodiment, $m_4$ and $m_5$ are each an integer of 1 to 3.

According to another embodiment, when $m_1$ to $m_5$ are each 2 or greater, substituents in the parentheses are the same as or different from each other.

In one embodiment of the present specification, $Ar_1$ is hydrogen; a substituted or unsubstituted aryl group having 6 to carbon atoms; a substituted or unsubstituted alkylamine group having 1 to 30 carbon atoms; a substituted or unsubstituted arylamine group having 6 to 60 carbon atoms; a substituted or unsubstituted heteroarylamine group having 2 to 60 carbon atoms; a substituted or unsubstituted arylheteroarylamine group having 8 to 60 carbon atoms; or a substituted or unsubstituted heteroaryl group having 2 to 60 carbon atoms.

According to another embodiment, $Ar_1$ is hydrogen; a substituted or unsubstituted aryl group having 6 to 30 carbon atoms; a substituted or unsubstituted alkylamine group having 1 to 20 carbon atoms; a substituted or unsubstituted arylamine group having 6 to 30 carbon atoms; a substituted or unsubstituted heteroarylamine group having 2 to 30 carbon atoms; a substituted or unsubstituted arylheteroarylamine group having 8 to 30 carbon atoms; or a substituted or unsubstituted heteroaryl group having 2 to 30 carbon atoms.

In another embodiment, $Ar_1$ is hydrogen; a substituted or unsubstituted aryl group; a substituted or unsubstituted arylamine group; a substituted or unsubstituted heteroarylamine group; a substituted or unsubstituted arylheteroarylamine group; or a substituted or unsubstituted heteroaryl group.

According to another embodiment, $Ar_1$ is hydrogen; a substituted or unsubstituted aryl group having 6 to 60 carbon atoms; a substituted or unsubstituted arylamine group having 6 to 60 carbon atoms; a substituted or unsubstituted heteroarylamine group having 2 to 60 carbon atoms; a substituted or unsubstituted arylheteroarylamine group having 8 to 60 carbon atoms; or a substituted or unsubstituted heteroaryl group having 2 to 60 carbon atoms.

In another embodiment, $Ar_1$ is hydrogen; a substituted or unsubstituted aryl group having 6 to 30 carbon atoms; a substituted or unsubstituted arylamine group having 6 to 30 carbon atoms; a substituted or unsubstituted heteroarylamine group having 2 to 30 carbon atoms; a substituted or unsubstituted arylheteroarylamine group having 8 to 30 carbon atoms; or a substituted or unsubstituted heteroaryl group having 2 to 30 carbon atoms.

According to another embodiment, $Ar_1$ is hydrogen; a substituted or unsubstituted phenyl group; a substituted or unsubstituted biphenyl group; a substituted or unsubstituted fluorenyl group; a substituted or unsubstituted N-phenylcarbazole group; a substituted or unsubstituted dibenzofuran group; a substituted or unsubstituted dibenzothiophene group; a substituted or unsubstituted diphenylamine group; a substituted or unsubstituted dibiphenylamine group; a substituted or unsubstituted N-phenylcarbazole phenylamine group; a substituted or unsubstituted N-phenylcarbazole biphenylamine group; a substituted or unsubstituted fluorenylbiphenylamine group; or a substituted or unsubstituted di-N-phenylcarbazole amine group.

In another embodiment, $Ar_1$ is hydrogen; a phenyl group; a biphenyl group; a 9,9-dimethylfluorenyl group; an N-phenylcarbazole group; an N-phenylcarbazole group substituted with a phenyl group; an N-phenylcarbazole group substituted with a phenyl group substituted with a t-butyl group; a dibenzofuran group; a dibenzothiophene group; a diphenylamine group; a diphenylamine group substituted with a diphenylamine group; a dibiphenylamine group; an N-phenylcarbazole phenylamine group; an N-phenylcarbazole biphenylamine group; a 9,9-dimethylfluorenyl biphenylamine group; or a di-N-phenylcarbazole amine group.

According to one embodiment of the present specification, the compound of Chemical Formula 1 may be any one selected from among the following structures.

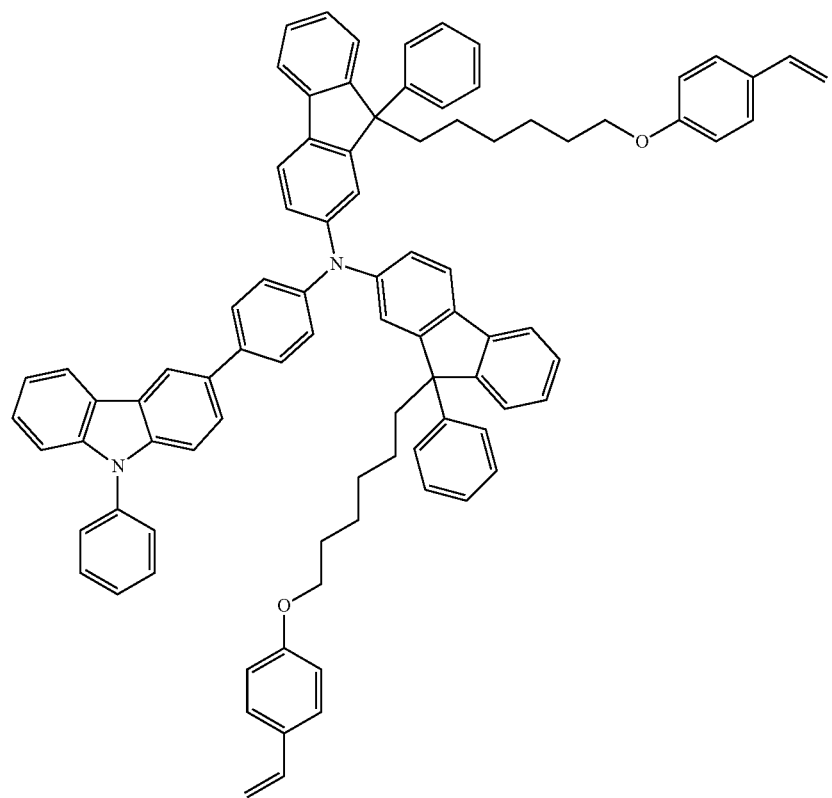
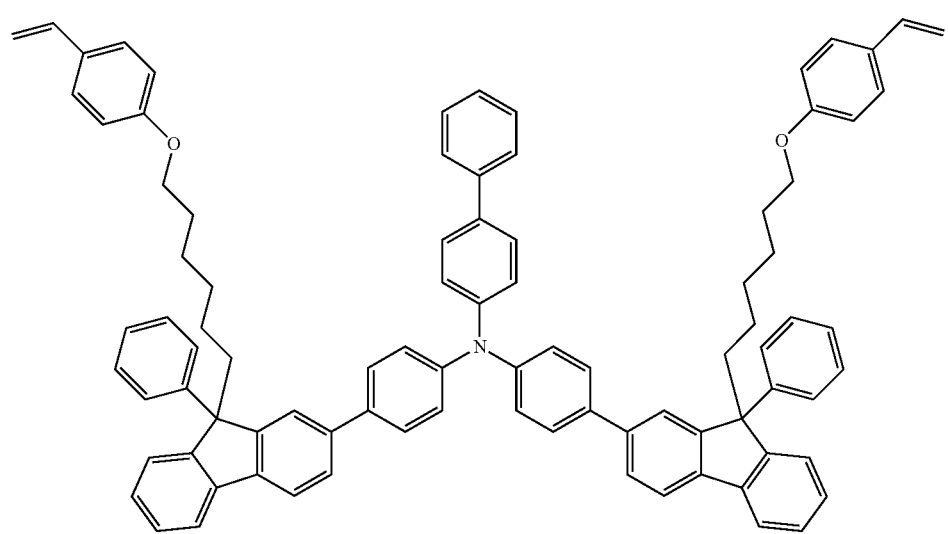

-continued
17
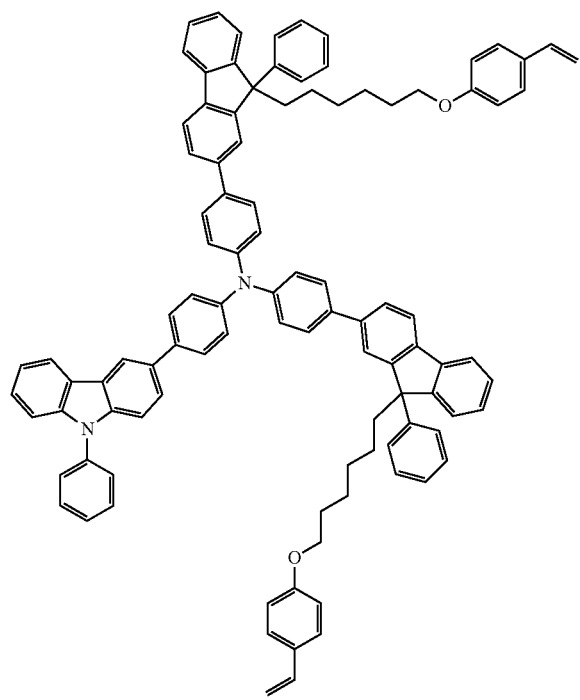
18
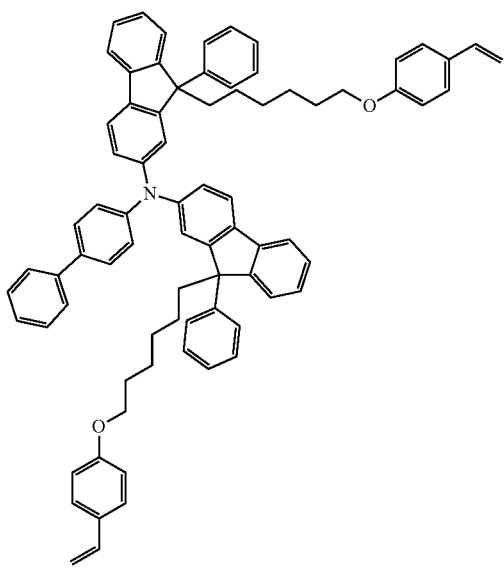
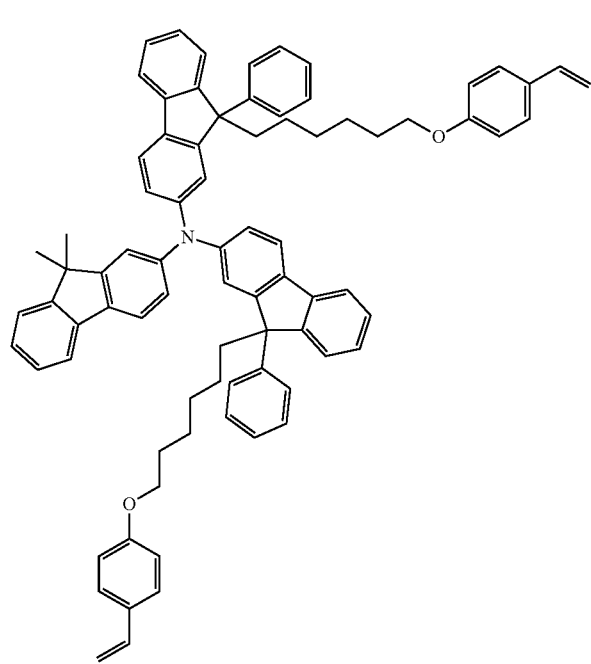
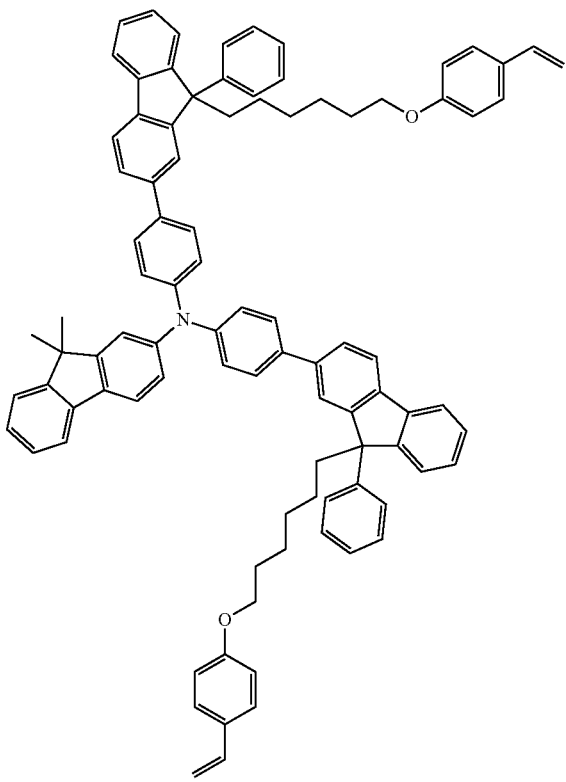

-continued
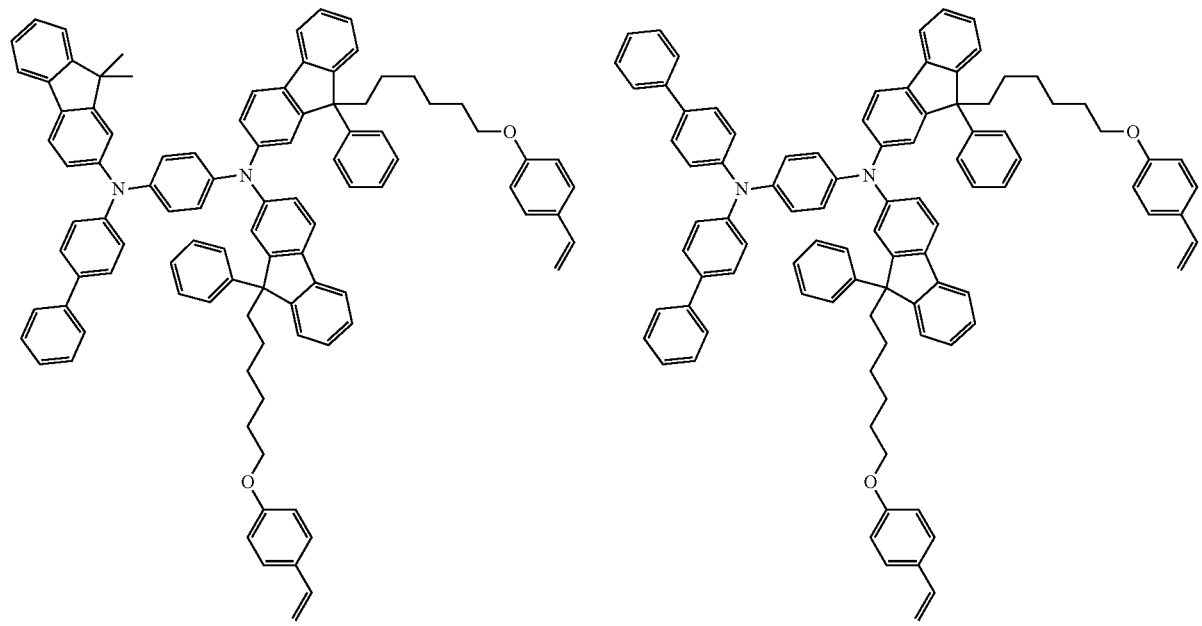
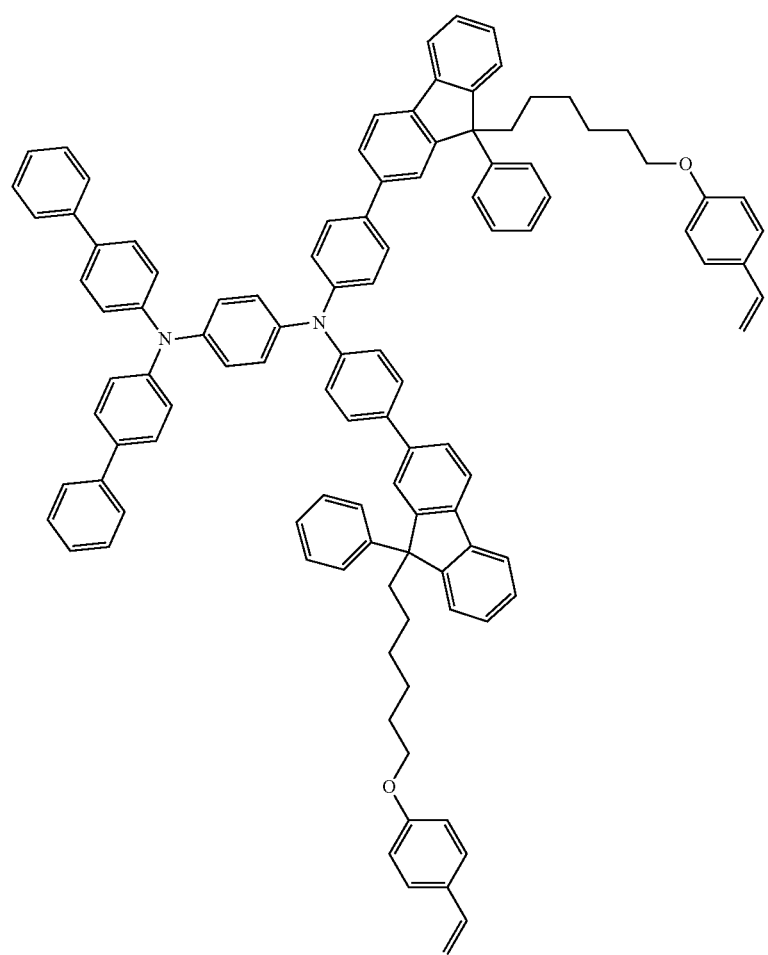

21
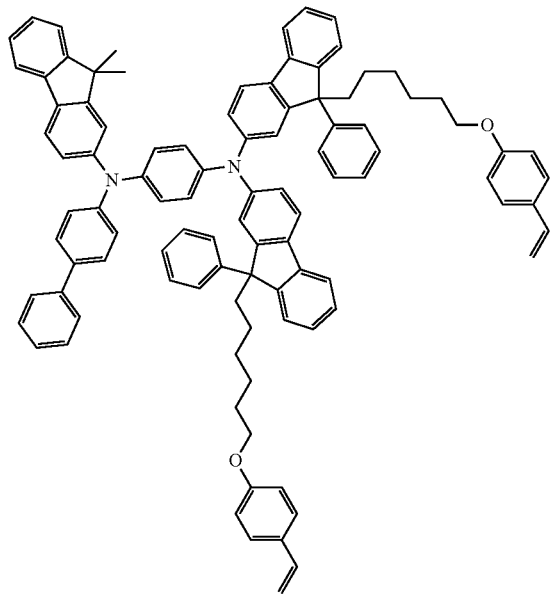
22
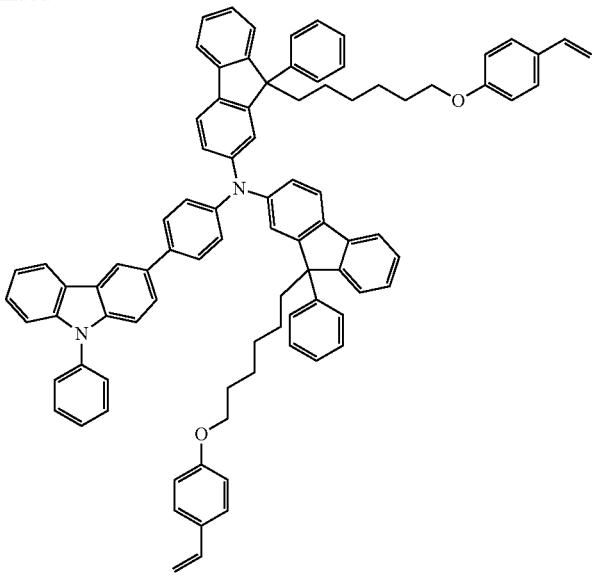
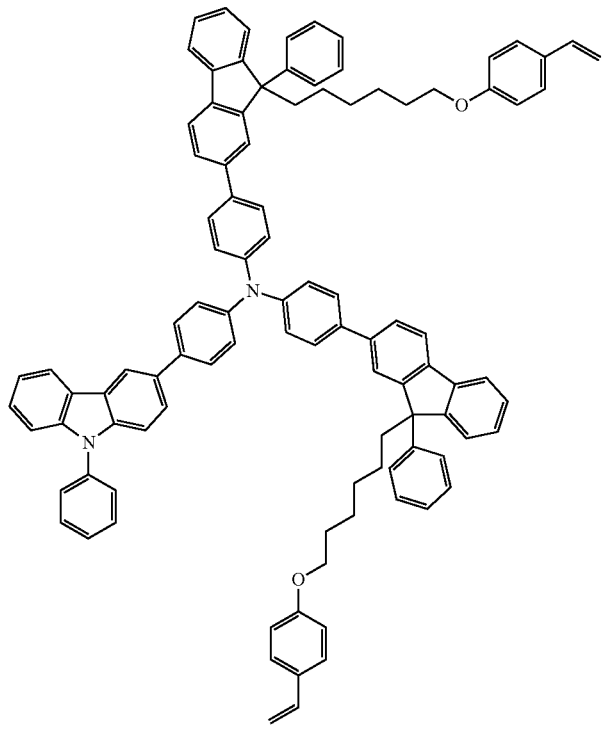
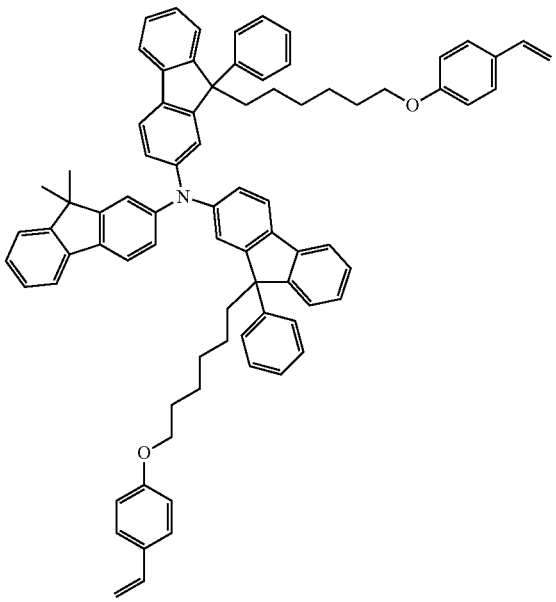

23
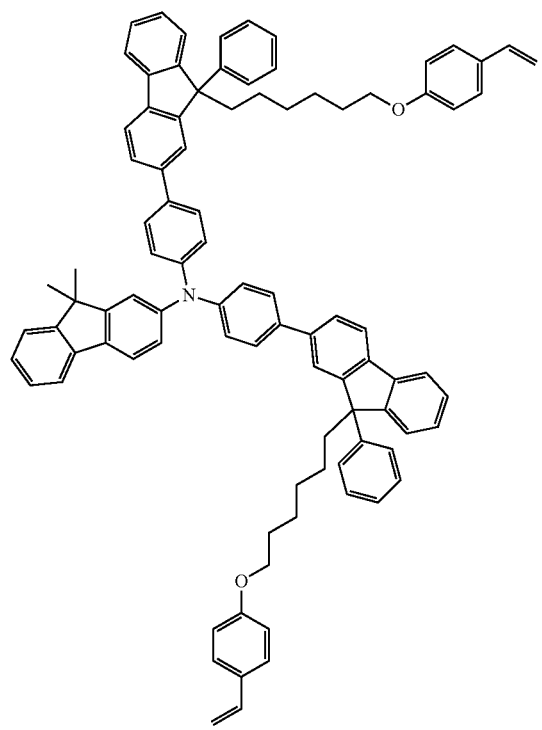
24
-continued
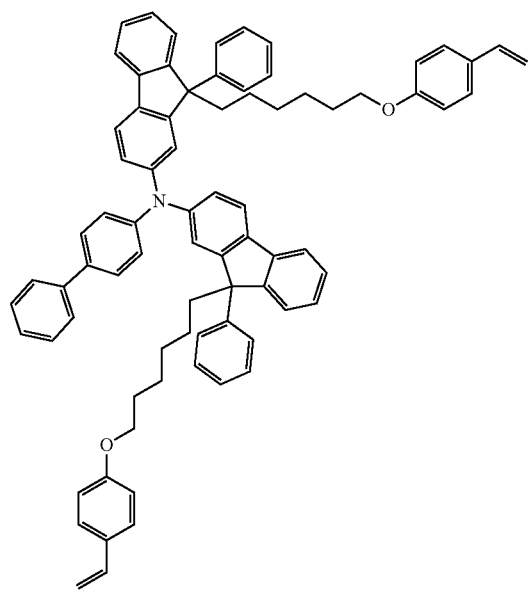
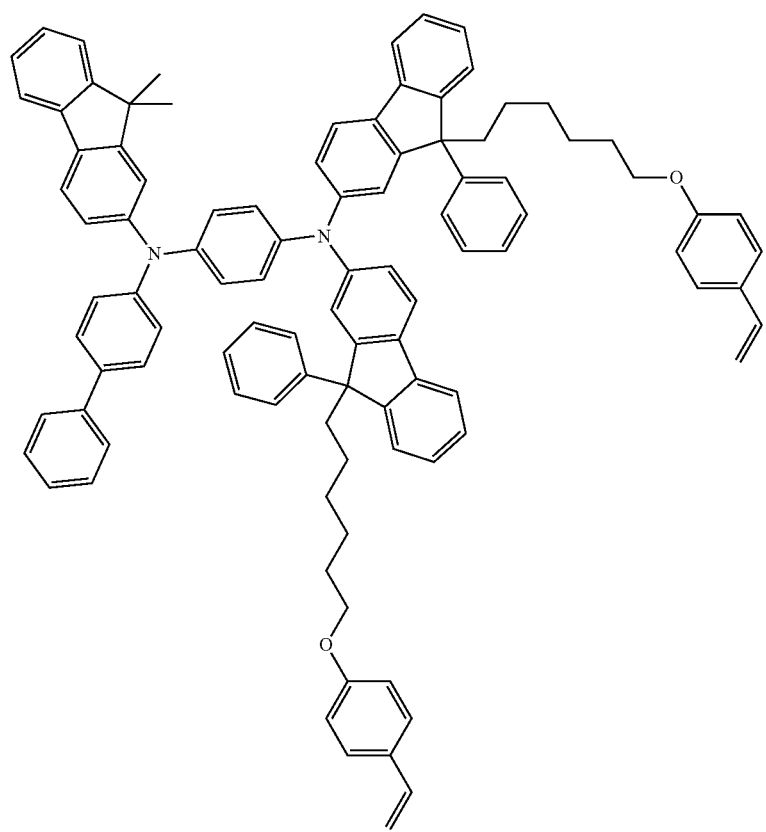

-continued
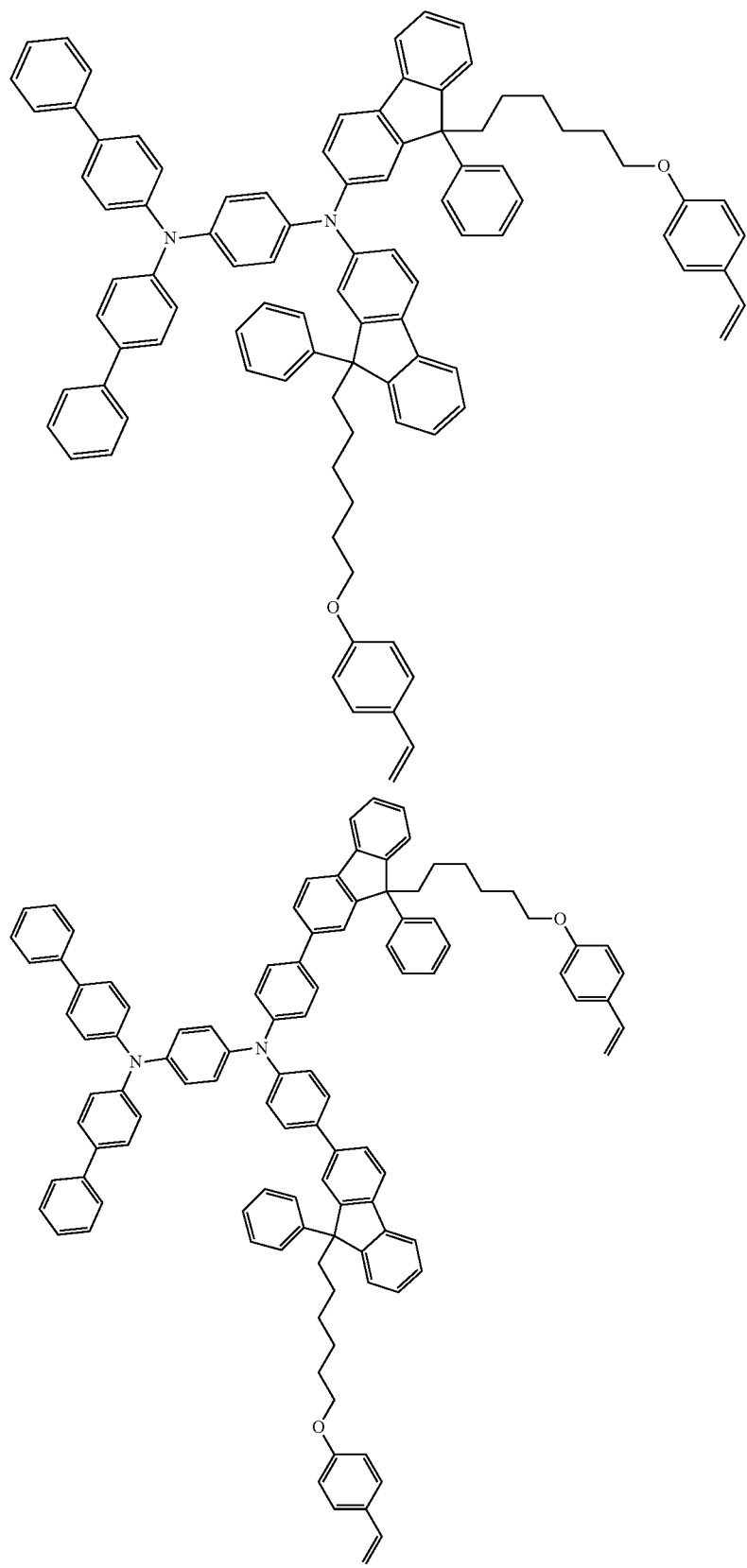

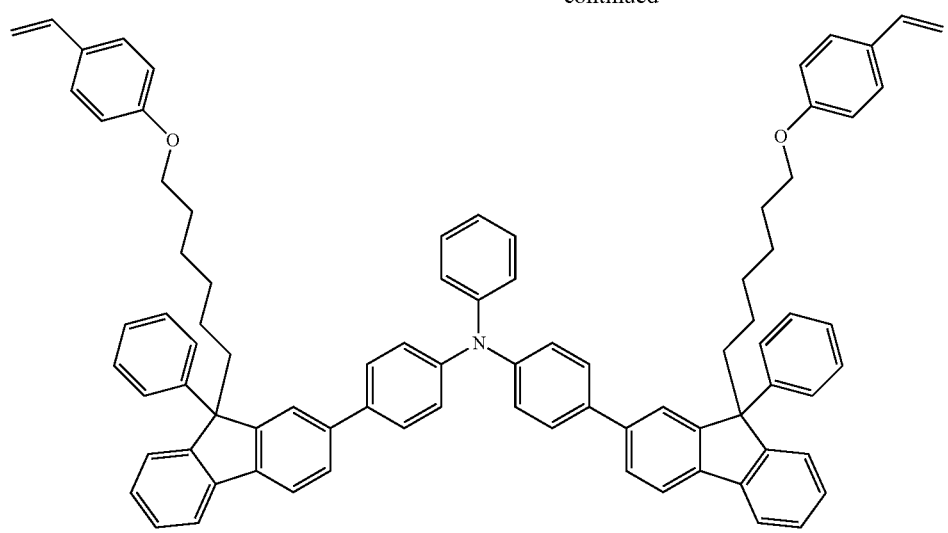
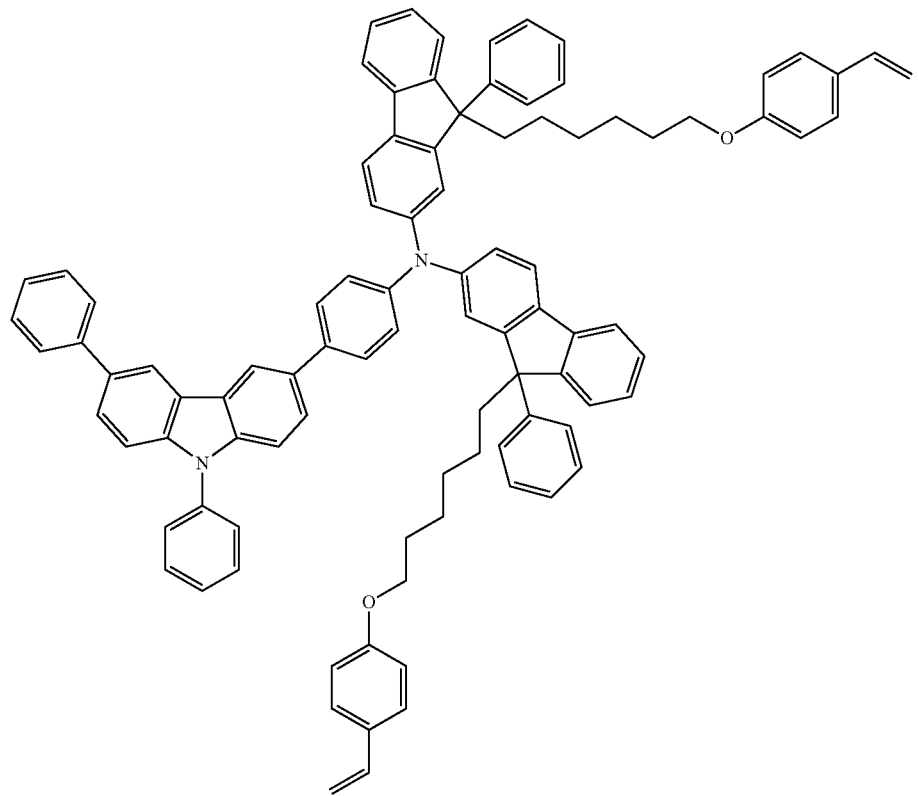

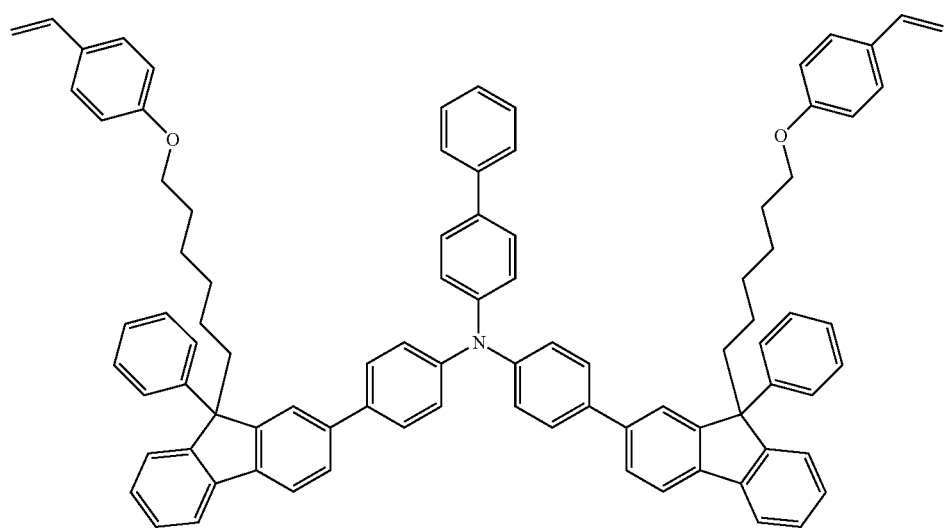
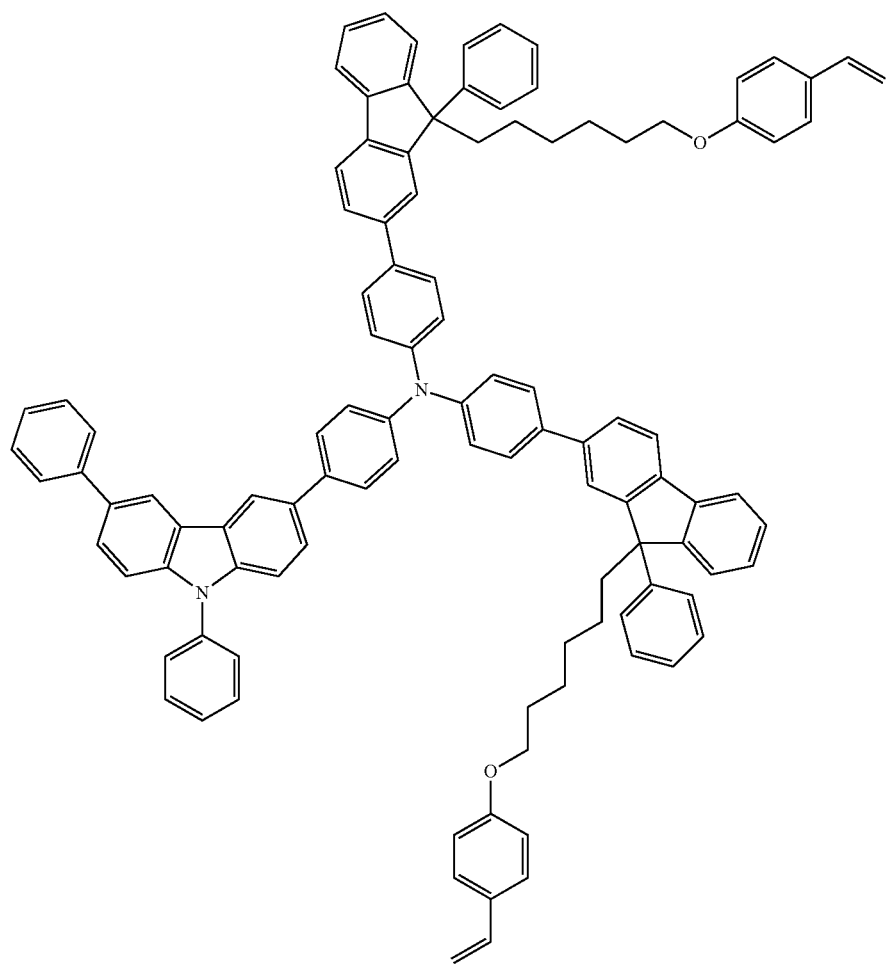

-continued
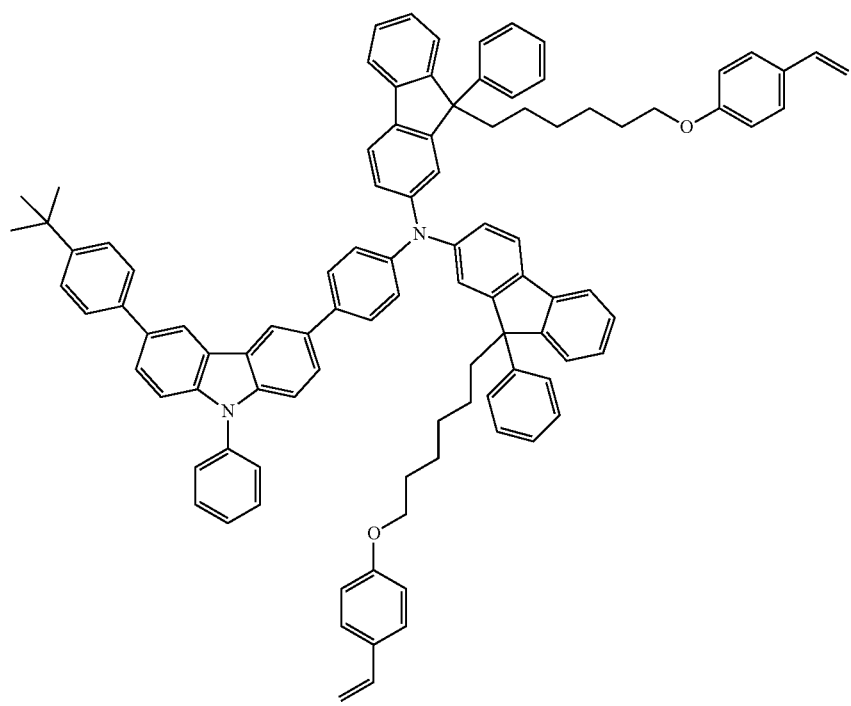
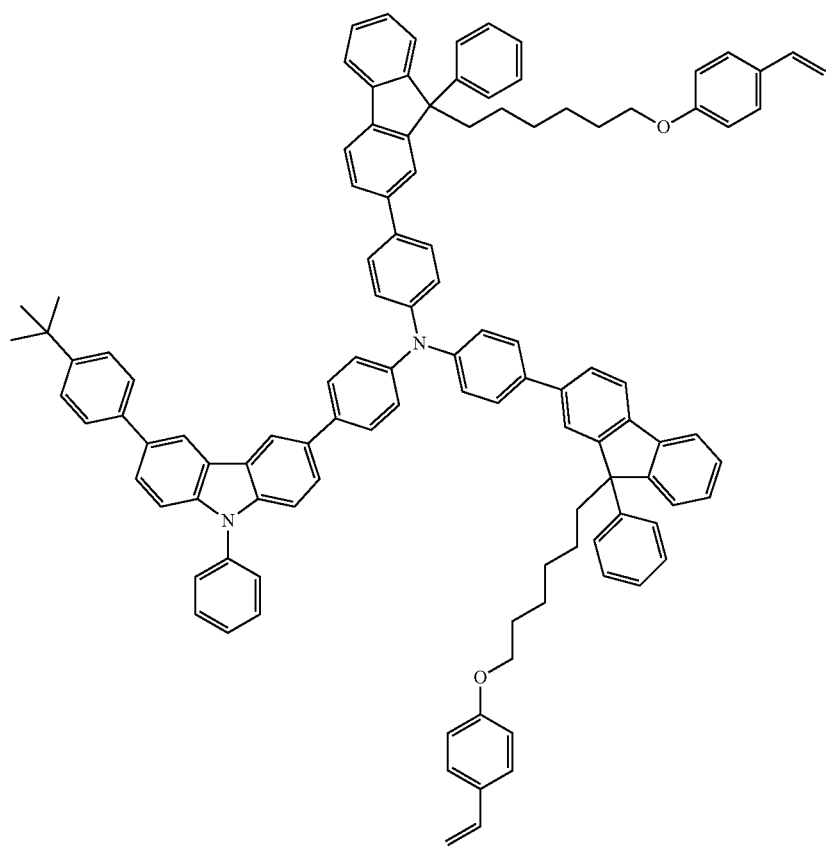

-continued
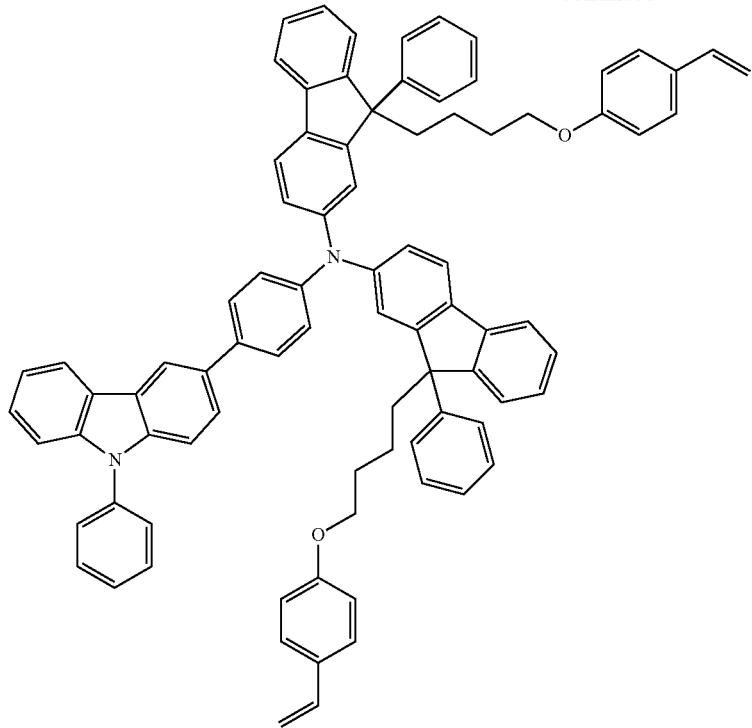
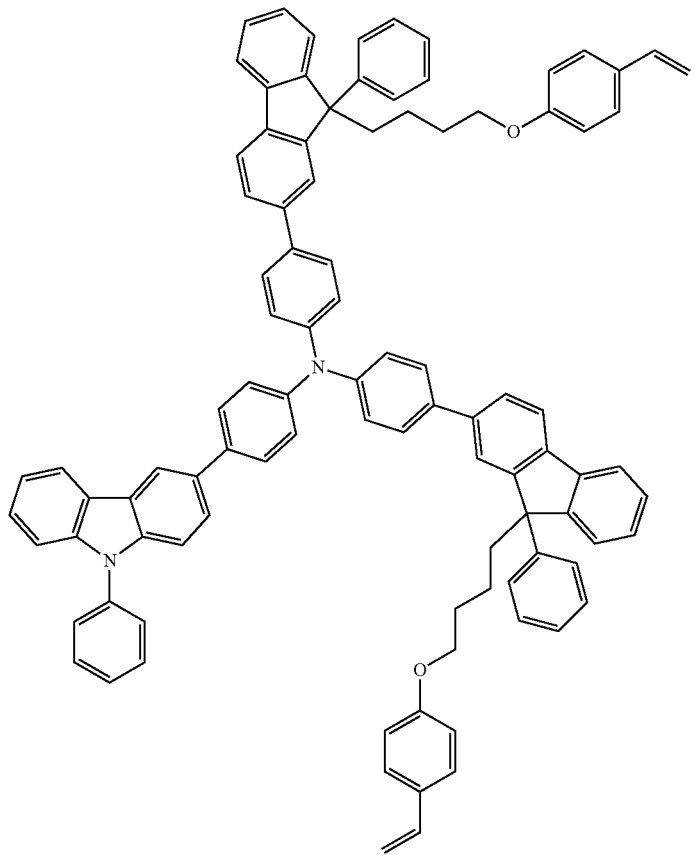

-continued
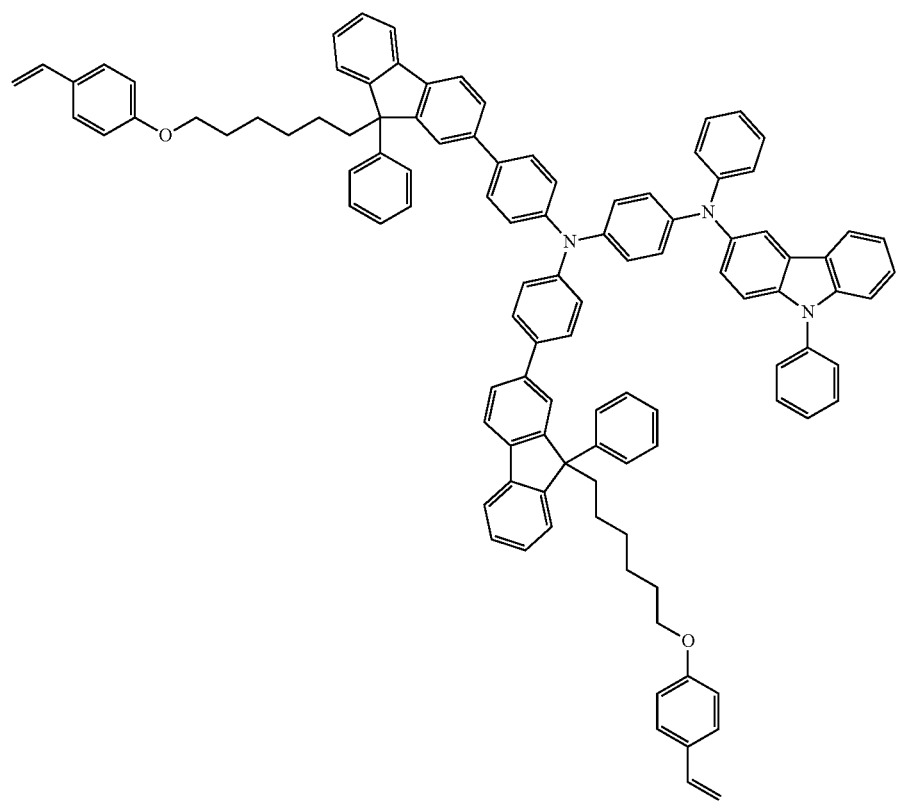
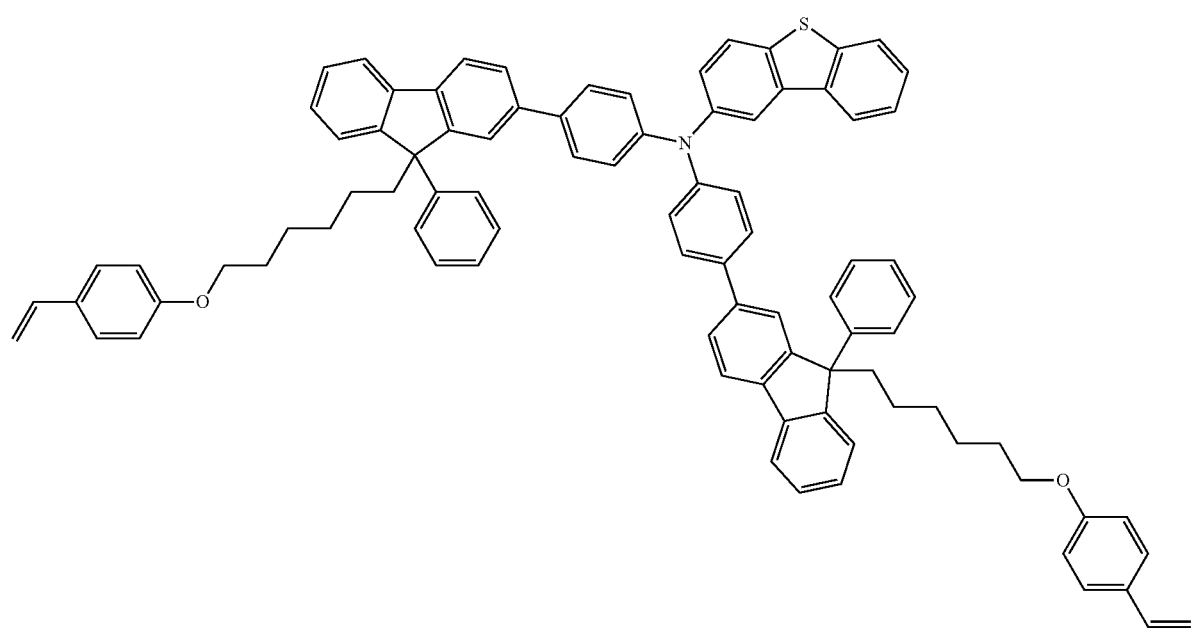

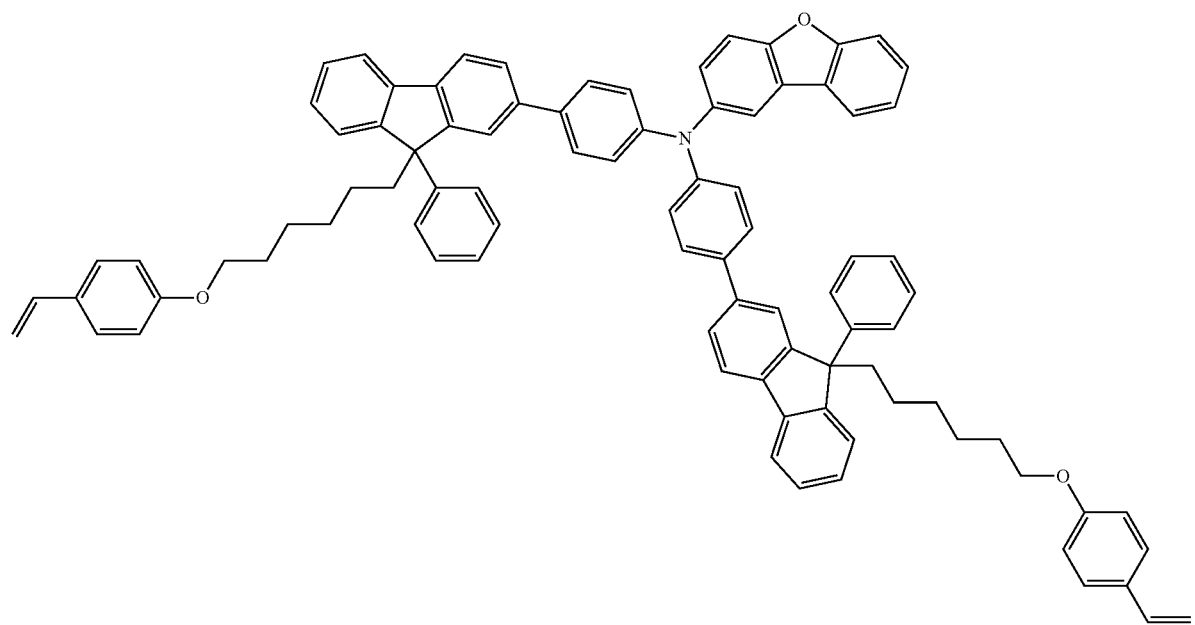
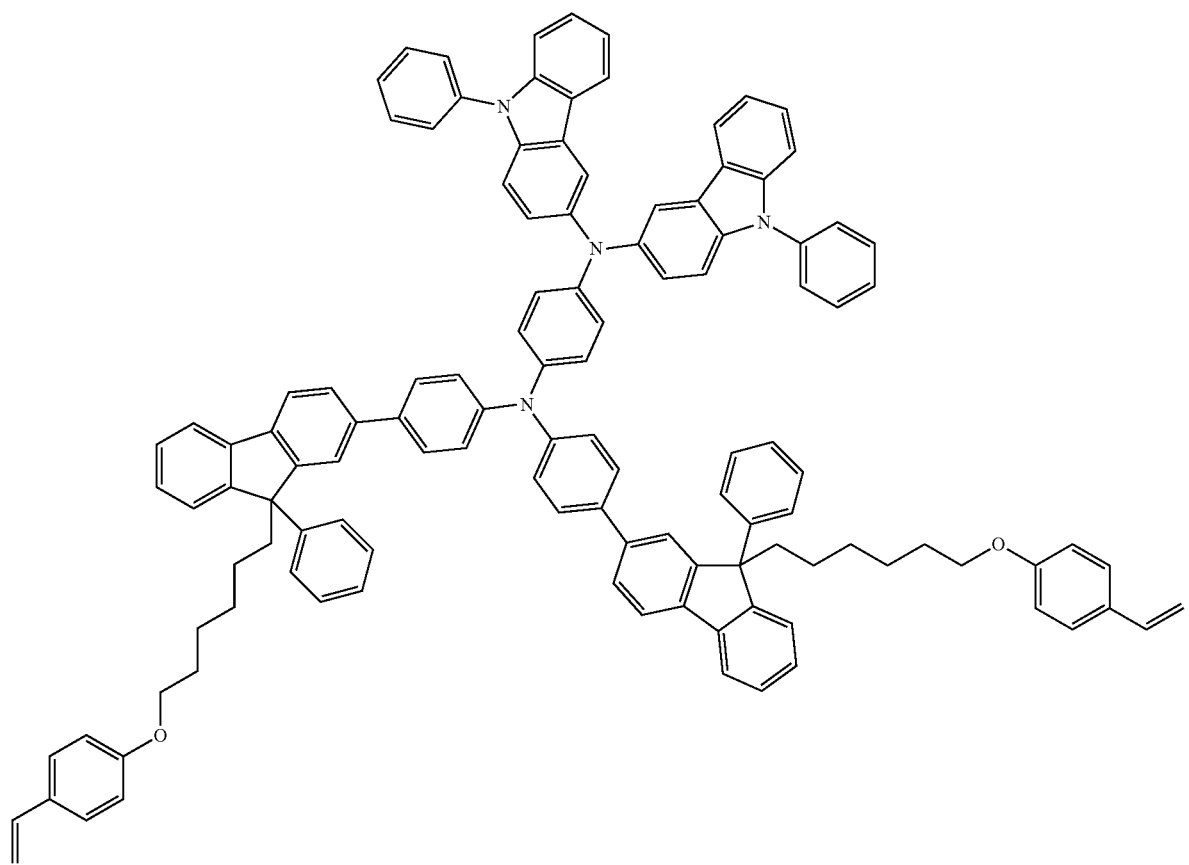

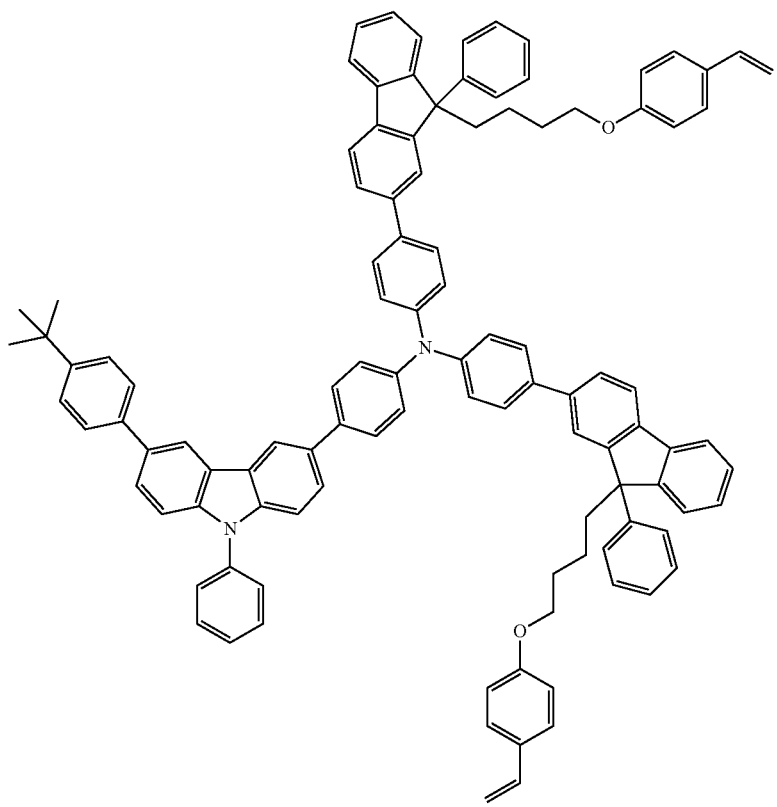
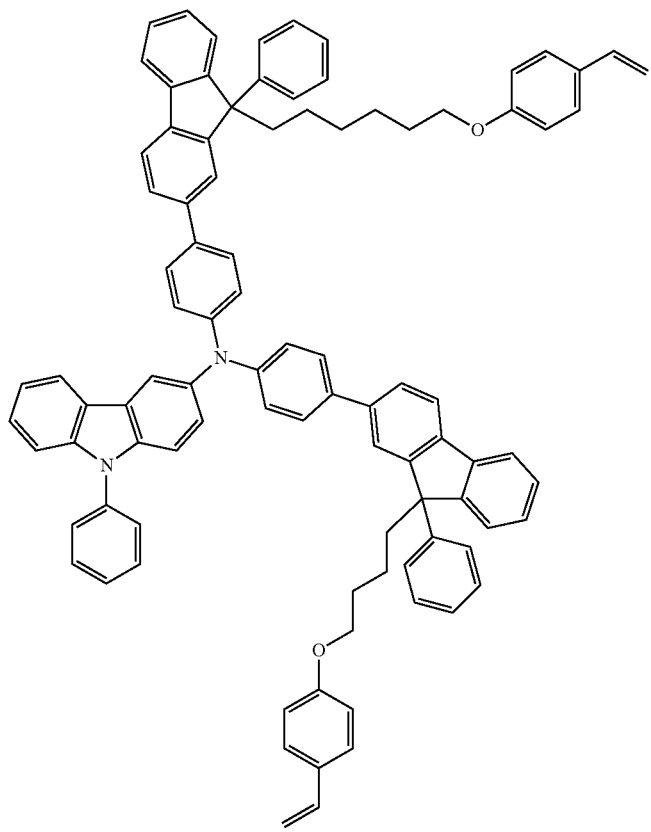

-continued
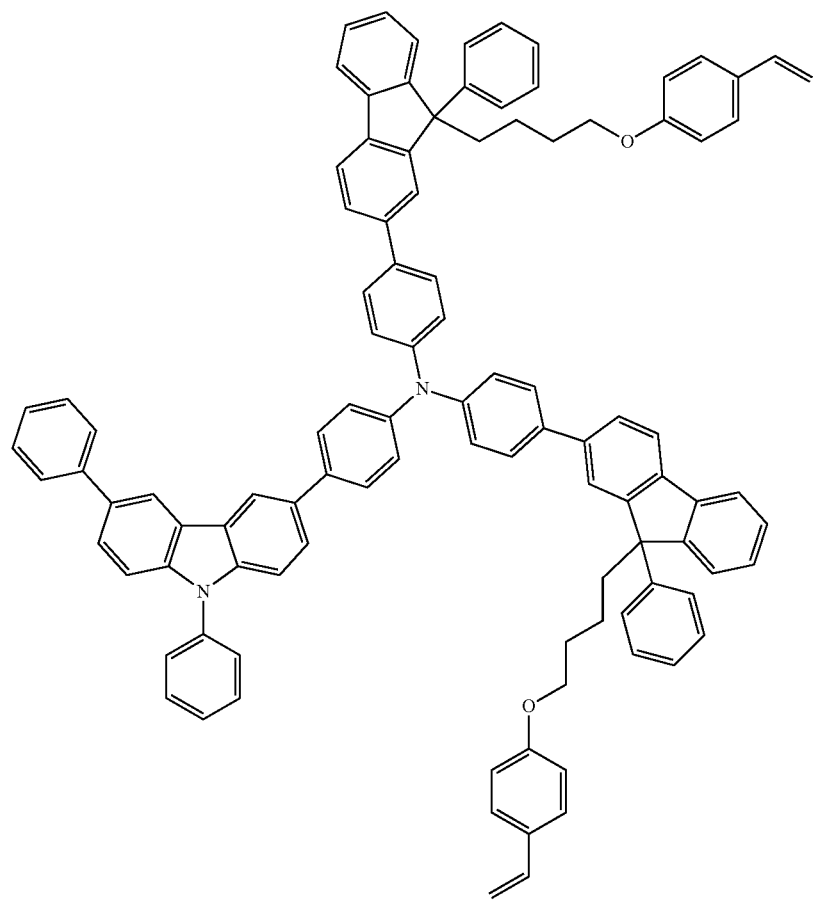
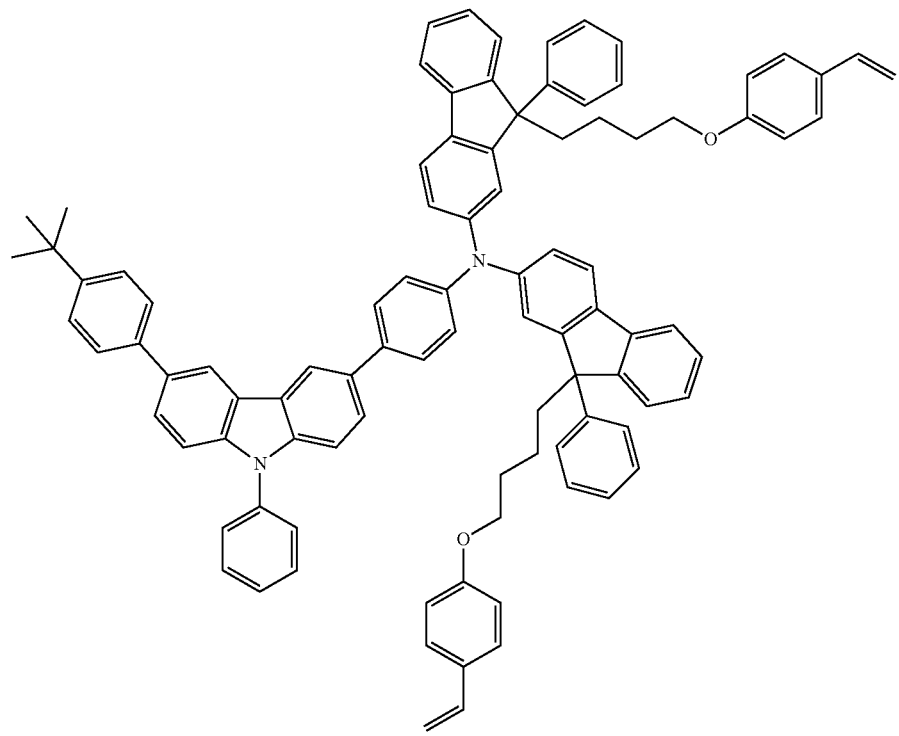

43
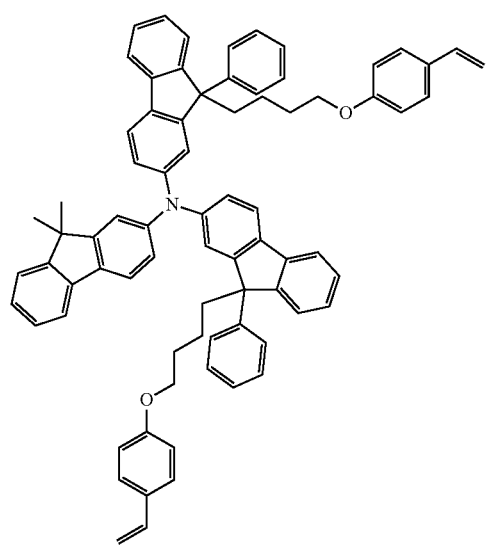
44
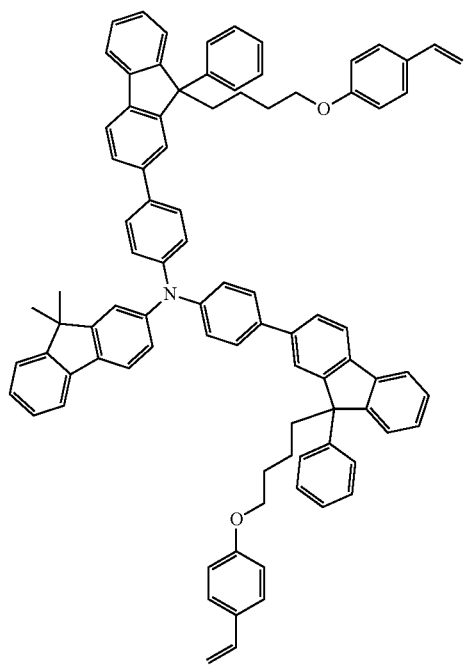
-continued
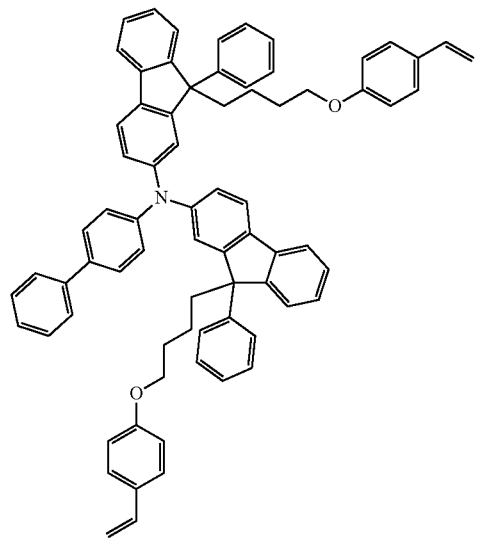
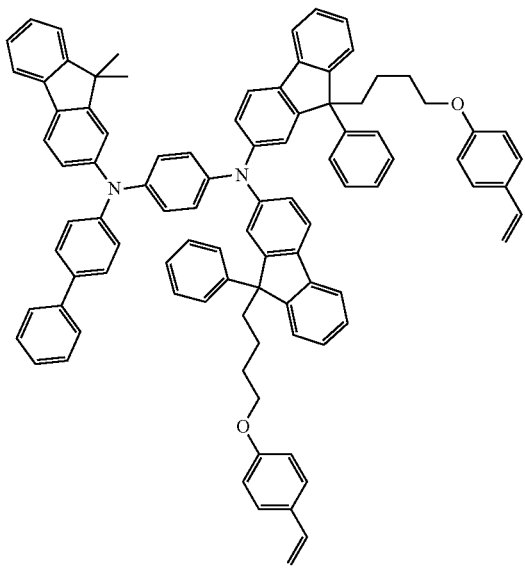

-continued
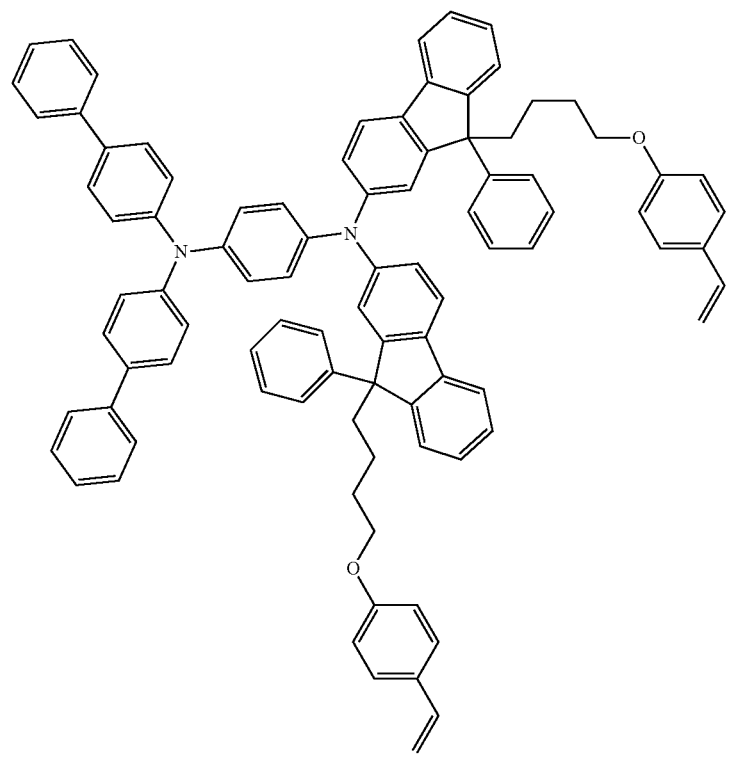
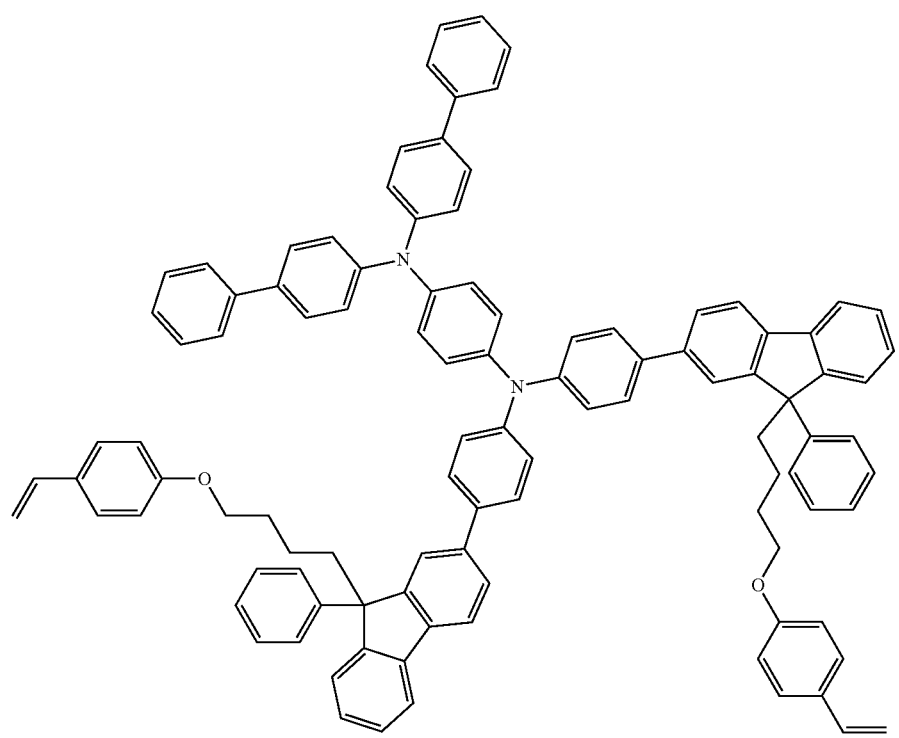

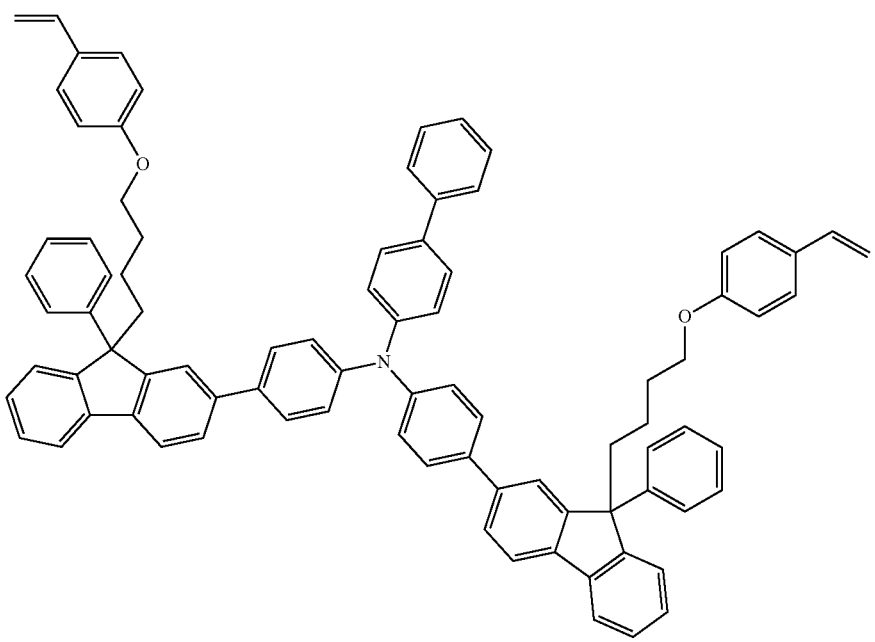
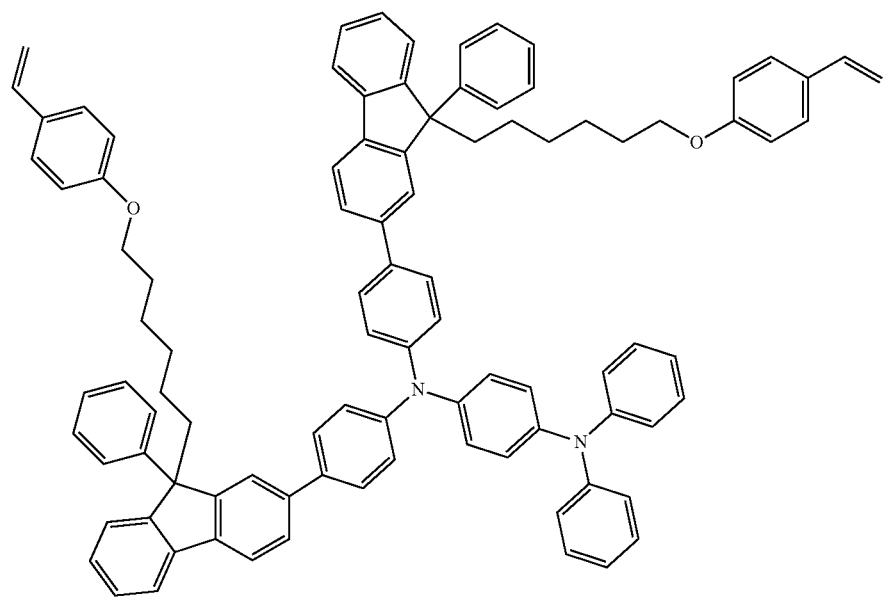

-continued
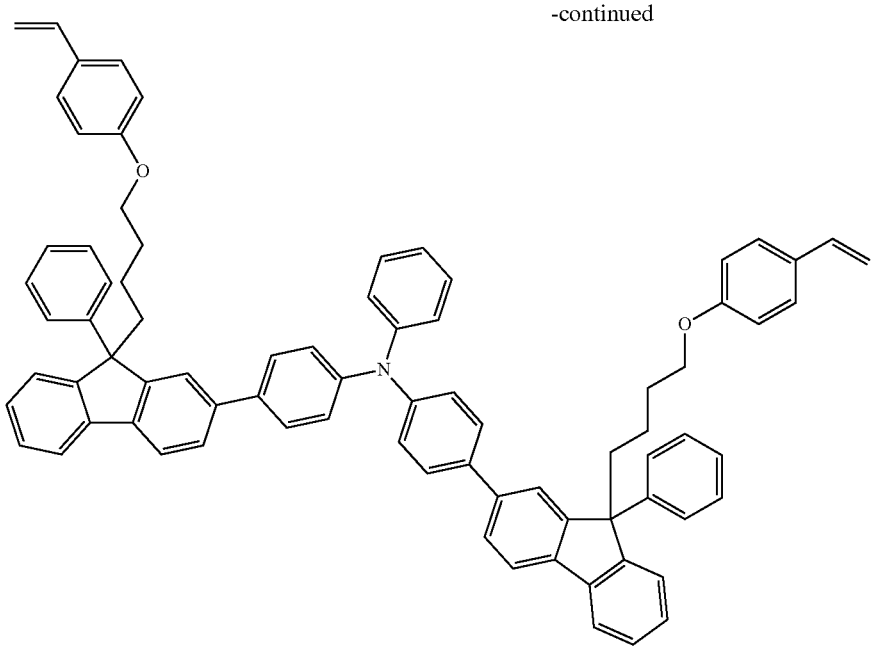
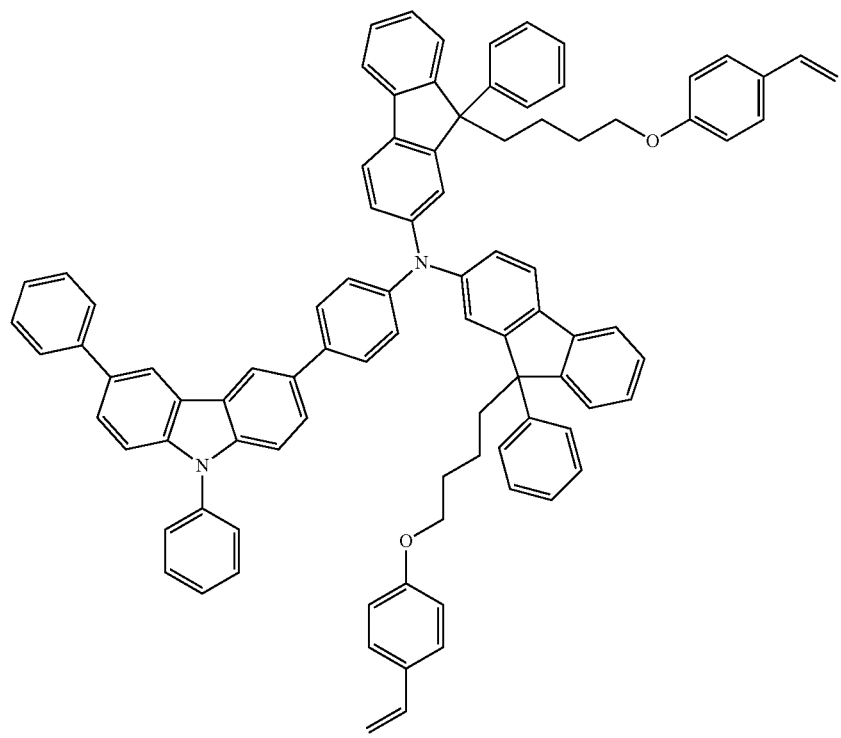

-continued
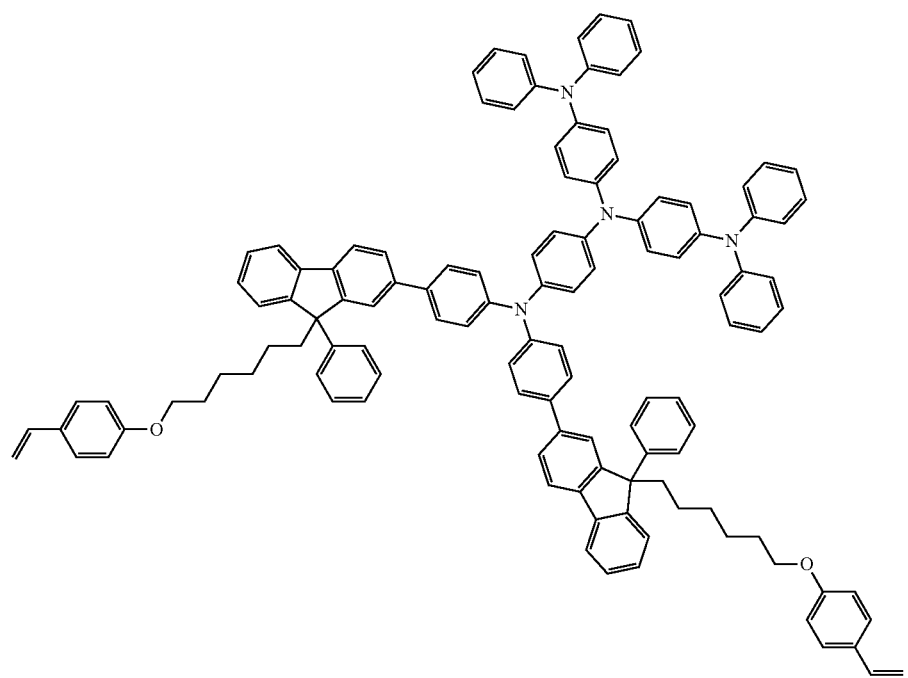
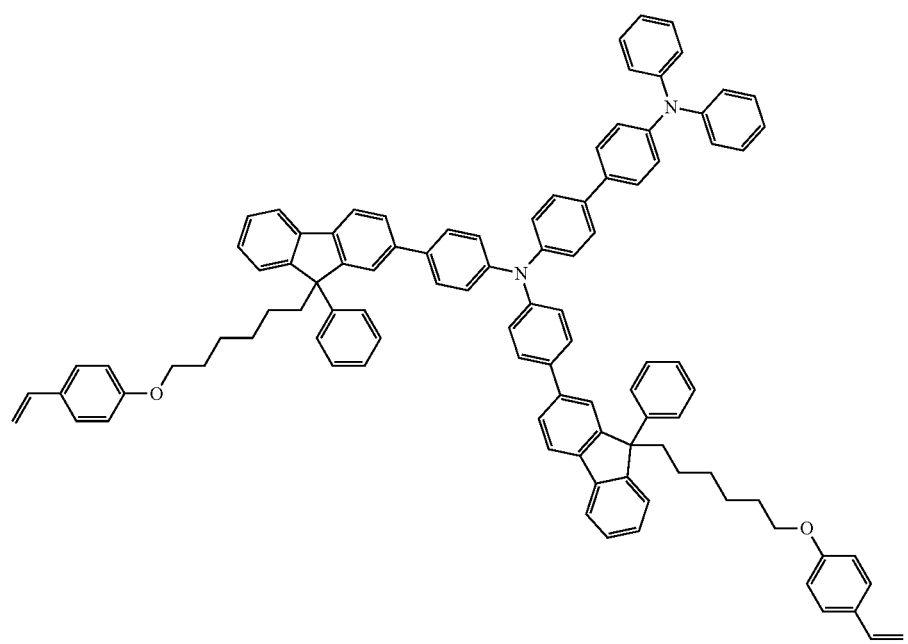

-continued
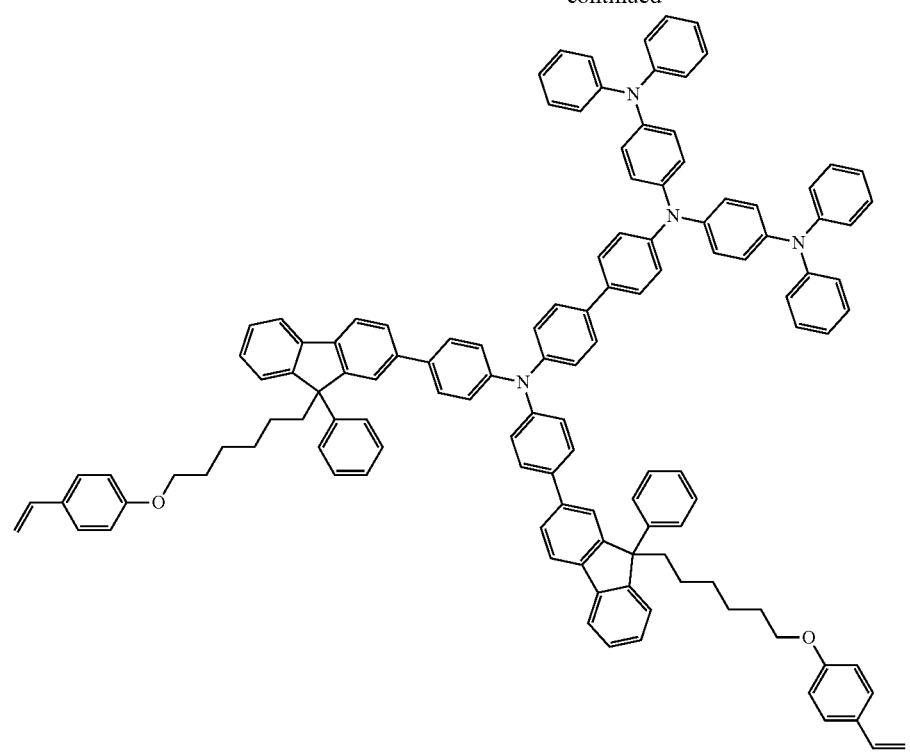
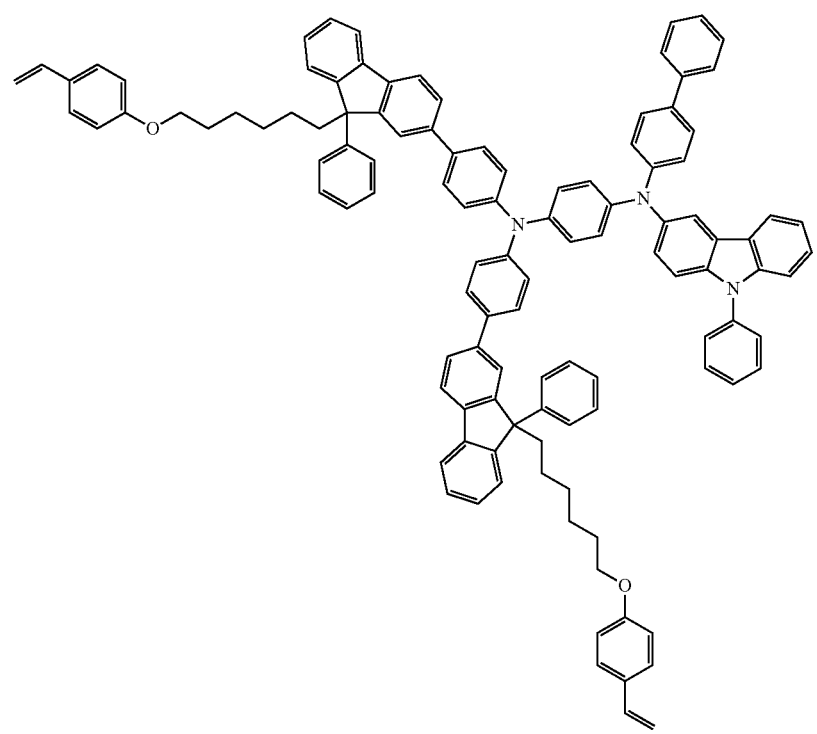 [SMILES: C=Cc1ccc(OCCCCCCC2(c3ccccc3)c3ccccc3-c3ccc(-c4ccc(N(c5ccc(-c6ccc7c(c6)C(CCCCCCOc6ccc(C=C)cc6)(c6ccccc6)c6ccccc6-7)cc5)c5ccc(N(c6ccc(-c7ccccc7)cc6)c6ccc7c(c6)c6ccccc6n7-c6ccccc6)cc5)cc4)cc32)cc1]

The compound according to one embodiment of the present specification may be prepared using a preparation method to describe below.

For example, the compound of Chemical Formula 1 may have its core structure prepared as in the following Reaction Formula 1. Substituents may bond using methods known in the art, and types, positions or the number of the substituents may vary depending on technologies known in the art.

<General Preparation Method of Chemical Formula 1>

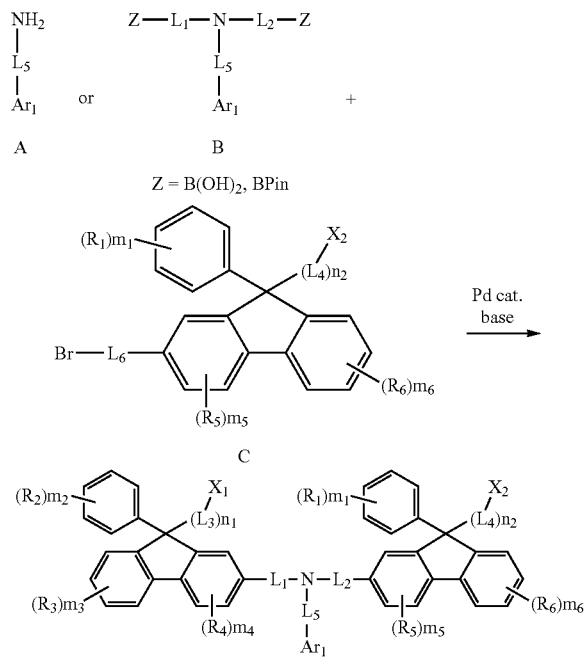

BPin means boronic acid pinacol ester

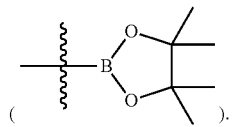 [SMILES: *B1OC(C)(C)C(C)(C)O1]

In the preparation method of Chemical Formula 1, Chemical Formula 1 may be prepared through a C—N or C—C coupling reaction using primary amine or a substituted or unsubstituted alkylamine group (A); or boronic ester or boronic acid including a substituted or unsubstituted arylamine group (B); and aryl bromide (C) including a curing group.

Substituents of Chemical Formula 1 have the same definitions as set forth above.

One embodiment of the present specification provides a coating composition including the compound of Chemical Formula 1 described above.

In one embodiment of the present specification, the coating composition includes the compound of Chemical Formula 1 and a solvent.

In one embodiment of the present specification, the coating composition may further include one or two types of compounds selected from the group consisting of a compound having a functional group crosslinkable by heat or light introduced into the molecule, and a polymer compound.

In one embodiment of the present specification, the coating composition may further include a compound having a functional group crosslinkable by heat or light introduced into the molecule. When the coating composition further includes a compound having a functional group crosslinkable by heat or light introduced into the molecule, the degree of curing of the coating composition may be further increased.

In one embodiment of the present specification, the compound having a functional group crosslinkable by heat or light introduced into the molecule has a molecular weight of 1,000 g/mol to 3,000 g/mol.

In one embodiment of the present specification, the coating composition may further include a polymer compound. When the coating composition further includes a polymer compound, ink properties of the coating composition may be further increased. In other words, the coating composition further including a polymer compound may provide proper viscosity for coating or ink jetting.

In one embodiment of the present specification, the polymer compound has a molecular weight of 10,000 g/mol to 200,000 g/mol.

In one embodiment of the present specification, the polymer compound may further include a crosslinkable functional group.

In one embodiment of the present specification, the coating composition may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene or o-dichlorobenzene; ether-based solvents such as tetrahydrofuran or dioxane; aromatic hydrocarbon-based solvents such as toluene, xylene, trimethylbenzene or mesitylene; aliphatic hydrocarbon-based solvents such as cyclohexane, methylcyclohexane, n-pentane, n-hexane, n-heptane, n-octane, n-nonane or n-decane; ketone-based solvents such as acetone, methyl ethyl ketone, cyclohexanone, isophorone, tetralone, decalone or acetylacetone; ester-based solvents such as ethyl acetate, butyl acetate or ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin or 1,2-hexanediol, and derivatives thereof; alcohol-based solvents such as methanol, ethanol, propanol, isopropanol or cyclohexanol; sulfoxide-based solvents such as dimethyl sulfoxide; amide-based solvents such as N-methyl-2-pyrrolidone or N,N-dimethylformamide; tetraline, and the like, however, the solvent is not limited thereto as long as it is a solvent capable of dissolving or dispersing the compound of Chemical Formula 1 according to one embodiment of the present disclosure.

In another embodiment, the solvent may be used either alone as one type, or as a mixture mixing two or more solvent types.

In one embodiment of the present specification, the coating composition may further include one, two or more types of additives selected from the group consisting of thermal polymerization initiators and photopolymerization initiators.

Examples of the thermal polymerization initiator may include peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5, 5-trimethyl hexanoyl peroxide, lauryl peroxide, benzoyl peroxide, p-chlorobenzoyl peroxide, dicumyl peroxide, 2,5-dimethyl-2,5-(t-butyloxy)-hexane, 1,3-bis(t-butylperoxy-isopropyl)benzene, t-butyl cumyl peroxide, di-t-butyl peroxide, 2,5-dimethyl-2,5-(di-t-butylperoxy)hexane-3, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate or di-t-butyl peroxytrimethyl adipate; or azo-based such as azobis isobutylnitrile, azobis dimethylvaleronitrile or azobis cyclohexyl nitrile, but are not limited thereto.

Examples of the photopolymerization initiator may include acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one or 1-phenyl-1,2-propanedion-2-(0-ethoxycarbonyl)oxime; benzoin ether-based photopolymerization initiators such as benzoin, benzoin methyl ether, benzoin ethyl ether, benzoin isobutyl ether or benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone or 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone or 2,4-dichlorothioxanthone; and, as other photopolymerization initiators, ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds and imidazole-based compounds. In addition, those having a photopolymerization facilitating effect may be used either alone or together with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

In one embodiment of the present specification, the coating composition does not further include a p-doping material.

In one embodiment of the present specification, the coating composition further includes a p-doping material.

In the present specification, the p-doping material may facilitate thermal curing or photocuring.

In the present specification, the p-doping material means a material enabling a host material to have a p semiconductor property. The p semiconductor property means a property receiving holes through injection or transferring holes at a highest occupied molecular orbital (HOMO) energy level, that is, a material having high hole conductivity.

In one embodiment of the present specification, the p-doping material may be represented by any one of the following Chemical Formulae 3 to 9, but is not limited thereto.

[Chemical Formula 3]

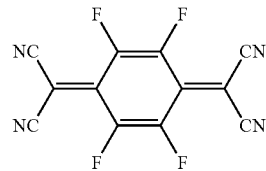

[Chemical Formula 4]

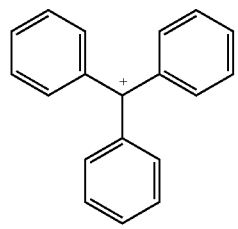

[Chemical Formula 5]

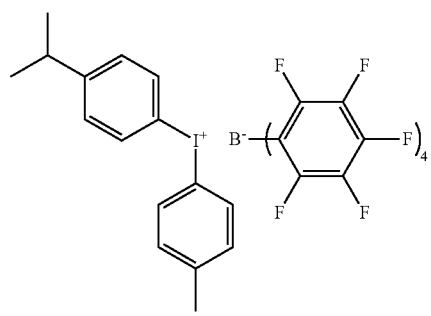

[Chemical Formula 6]

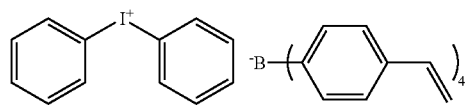

[Chemical Formula 7]

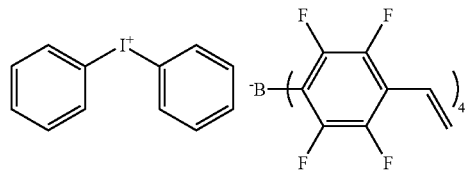

[Chemical Formula 8]

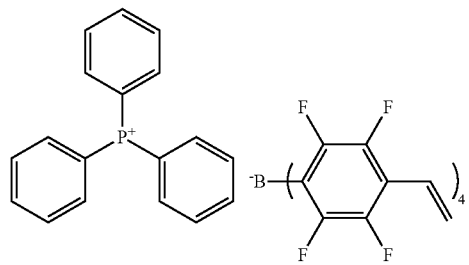

[Chemical Formula 9]

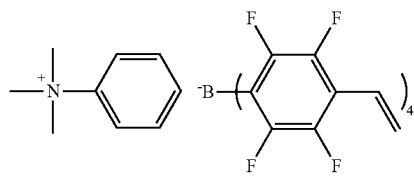

In the present specification, the p-doping material is not limited as long as it has a p semiconductor property, and one, two or more types thereof may be used, and types thereof are not limited.

In one embodiment of the present specification, a content of the p-doping material is from 0% by weight to 50% by weight based on the compound of Chemical Formula 1.

In one embodiment of the present specification, a content of the p-doping material is from 0% by weight to 30% by weight based on a total solid content of the coating composition. In one embodiment of the present specification, a content of the p-doping material is preferably from 1% by weight to 30% by weight based on a total solid content of the coating composition, and in another embodiment, a content of the p-doping material is more preferably from 1% by weight to 30% by weight based on a total solid content of the coating composition.

In another embodiment, the coating composition may further include a monomer including a functional group crosslinkable by heat or light; or a monomer including an end group capable of forming a polymer by heat. The monomer including a functional group crosslinkable by heat or light; or the monomer including an end group capable of forming a polymer by heat as above may be a compound having molecular weight of 2,000 g/mol or less.

In one embodiment of the present specification, the coating composition has a molecular weight of 2,000 g/mol or less, and further includes a monomer including a functional group crosslinkable by heat or light; or a monomer including an end group capable of forming a polymer by heat.

The monomer including a functional group crosslinkable by heat or light; or the monomer including an end group capable of forming a polymer by heat may mean a monomer in which aryl of phenyl, biphenyl, fluorene or naphthalene; arylamine; or fluorene is substituted with a functional group crosslinkable by heat or light or an end group capable of forming a polymer by heat.

The crosslinkable functional group has the same definition as above.

In addition, in one embodiment of the present specification, the monomer including a crosslinkable functional group may include the following structures, but is not limited thereto as long as it does not harm properties of the coating composition of the present specification.

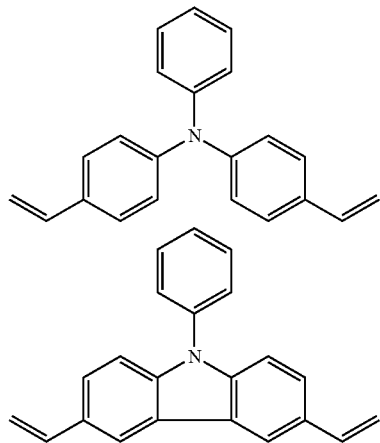

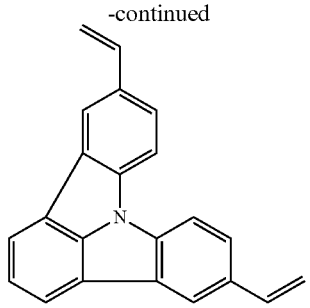

In another embodiment, the monomer including an end group capable of forming a polymer by heat may include the following structures, but is not limited thereto as long as it does not harm properties of the coating composition of the present specification.

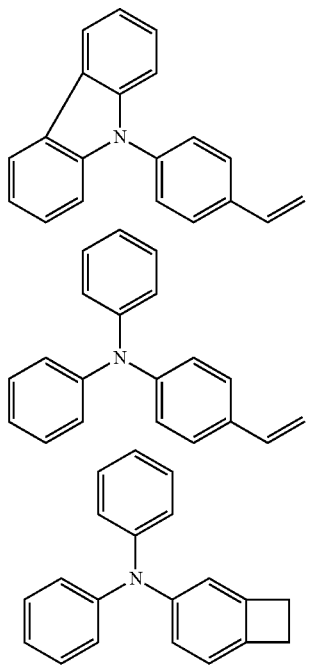

In another embodiment, the coating composition has viscosity of 2 cP to 15 cP.

Satisfying the above-mentioned viscosity is advantageous in manufacturing a device.

Another embodiment of the present specification provides an organic light emitting device formed using the coating composition.

In one embodiment of the present specification, the organic light emitting device includes a cathode; an anode; and one or more organic material layers provided between the cathode and the anode, wherein one or more layers of the organic material layers includes a cured material of the coating composition, and the cured material of the coating composition means being in a cured state by heat treating or light treating the coating composition.

In one embodiment of the present specification, the organic material layer including the cured material of the coating composition is a hole transfer layer, a hole injection layer or a layer carrying out hole transfer and hole injection at the same time.

In another embodiment, the organic material layer formed using the coating composition is a light emitting layer.

In another embodiment, the organic material layer including the cured material of the coating composition is a light emitting layer, and the light emitting layer includes the compound of Chemical Formula 1 as a host of the light emitting layer.

In one embodiment of the present specification, the organic light emitting device further includes one, two or more layers selected from the group consisting of a hole injection layer, a hole transfer layer. an electron transfer layer, an electron injection layer, an electron blocking layer and a hole blocking layer.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

For example, a structure of the organic light emitting device according to one embodiment of the present specification is illustrated in FIG. 1.

FIG. 1 illustrates a structure of the organic light emitting device in which an anode (201), a hole injection layer (301), a hole transfer layer (401), a light emitting layer (501), an electron injection layer (601) and a cathode (701) are consecutively laminated on a substrate (101).

FIG. 1 illustrates the organic light emitting device, however, the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers are formed using the coating composition including the compound of Chemical Formula 1.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, one embodiment of the present specification provides a method for manufacturing an organic light emitting device formed using the coating composition.

Specifically, the method for manufacturing an organic light emitting device in one embodiment of the present specification includes preparing a substrate; forming a cathode or an anode on the substrate; forming one or more organic material layers on the cathode or the anode; and forming an anode or a cathode on the organic material layer, wherein the forming of organic material layers includes forming one or more organic material layers using the coating composition.

In one embodiment of the present specification, the organic material layer formed using the coating composition is formed using spin coating.

In another embodiment, the organic material layer formed using the coating composition is formed using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer formed using the coating composition includes coating the coating composition on the cathode or the anode; and heat treating or light treating the coated coating composition.

In one embodiment of the present specification, the temperature of heat treatment in the heat treating is 230° C. or lower, and more specifically from 80° C. to 230° C.

In another embodiment, the time of heat treatment in the heat treating is from 1 minute to 1 hour.

In one embodiment of the present specification, when the coating composition does not include additives, polymerization is preferably progressed by heat treatment at a temperature of 80° C. to 230° C., and polymerization is more preferably progressed at a temperature of 80° C. to 200° C. In addition, the coating composition of the present specification may include an initiator, however, it is more preferred not to use an initiator.

When the heat treatment or the light treatment is included in the forming of an organic material layer formed using the coating composition, an organic material layer including a thin-filmed structure by a plurality of the compounds of Chemical Formula 1 included in the coating composition forming crosslinkage may be provided. In this case, being dissolved by a solvent or being morphologically affected or decomposed may be prevented when other layers are laminated on a surface of the organic material layer formed using the coating composition.

Accordingly, when the organic material layer formed using the coating composition is formed including heat treatment or light treatment, resistance for the solvent increases, and multiple layers may be formed by repeatedly performing solution deposition and crosslinking methods, and as a result, lifetime properties of a device may be enhanced by increasing stability.

In one embodiment of the present specification, the coating composition including the compound of Chemical Formula 1 may use a coating composition mixed and dispersed into a polymer binder.

As the polymer binder in one embodiment of the present specification, those that do not extremely inhibit charge transfer are preferred, and those that do not exhibit strong absorption for visible light are preferably used. Examples of the polymer binder include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

In addition, by the compound of Chemical Formula 1 according to one embodiment of the present specification including a fluorene or amine group, the compound of Chemical Formula 1 may be included alone in the organic material layer, the coating composition including the compound of Chemical Formula 1 may be thin-filmed through heat treatment or light treatment, or a coating composition mixed with other monomers may be included as a copolymer. In addition, a coating composition mixed with other polymers may be included as a copolymer or included as a mixture.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as barium, magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole-based compounds; dimerized styryl compounds; BAlq; 10-hydroxybenzo quinoline-metal compounds; benzoxazole-, benzthiazole- and benzimidazole-based compounds; poly(p-phenylenevinylene) (PPV)-based polymers; spiro compounds; polyfluorene, rubrene, or the like, but are not limited thereto.

The light emitting layer may include a host material and a dopant material.

The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and includes arylamino group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted.

Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, or the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato) (0-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, BCP, aluminum complexes and the like are included, however, the material is not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

Preparation Example

Preparation Example 1. Preparation of Compound 1-1

1) Synthesis of Intermediate 1

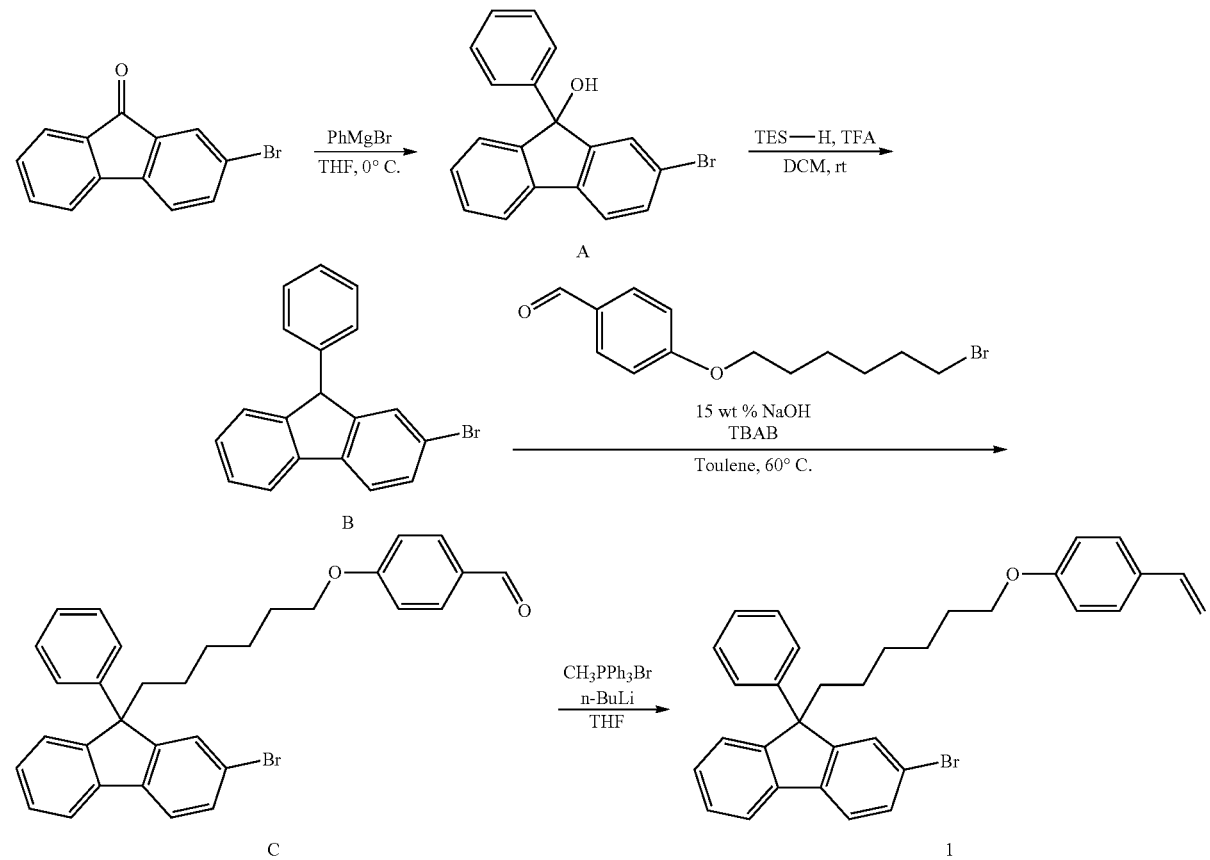

In a 500 mL 1-neck RBF, 2-bromo-9H-fluoren-9-one (20 g, 77.2 mmol) was introduced and dissolved in THF (250 ml). 3.0 M PhMgBr (38 ml) dissolved in diethyl ether was added thereto in an ice bath. The result was reacted for approximately 1 hour, and then quenched with $NH_4Cl$.

Water was further added thereto, and the organic layer was extracted using ethyl acetate (EA). The obtained organic layer was dried with MgSO$_4$, concentrated and then column purified to obtain Compound A.

In a 500 mL 1-neck RBF, A (20 g, 60 mmol) was placed, and dissolved by adding dichloromethane (150 ml) thereto. Triethylsilane (14 ml, 90 mmol) and trifluoroacetic acid (7 ml, mmol) were added dropwise thereto, and the result was stirred for 24 hours. Silica gel was dropped for adsorption, and then the result was columned using hexane to obtain Compound B.

In a 100 mL 1-neck RBF, B (2.8 g, 8.7 mmol), 4-((6-bromohexyl)oxy)benzaldehyde (2.7 g, 9.6 mmol) and tetrabutylammonium bromide (0.14 g, 0.44 mmol) were placed, and dissolved by adding toluene (20 ml) thereto. After raising the temperature to approximately 50° C., the result was degassed for approximately 30 minutes, 15 wt % NaOH (7 ml) was introduced thereto, and the result was reacted for approximately 18 hours at 60° C. Ammonium chloride was introduced thereto to terminate the reaction, water was added thereto, and the organic layer was extracted using EA. The obtained organic layer was dried with MgSO$_4$, concentrated, and then recrystallized using methylene chloride (MC) and ethanol to obtain Compound C.

In a 100 mL 1-neck RBF, CH$_3$PPh$_3$Br (5.4 g, 15.16 mmol) was placed, THF (20 mL) was introduced thereto, and the result was stirred. 2.5 M n-BuLi (5.7 ml) was slowly added dropwise thereto in an ice bath, and the result was reacted for approximately 30 minutes. Compound C (2.5 g, 4.7 mmol) dissolved in THF (20 mL) was slowly introduced thereto in an ice bath, and the result was reacted for approximately 3 hours. The reaction was terminated using water, water was further added thereto, and the organic layer was extracted using ethyl acetate (EA). The obtained organic layer was dried using Na$_2$SO$_4$, concentrated and then flash columned to obtain Intermediate 1. An MS graph of Intermediate 1 is shown in FIG. 6.

2) Synthesis of Intermediate 2

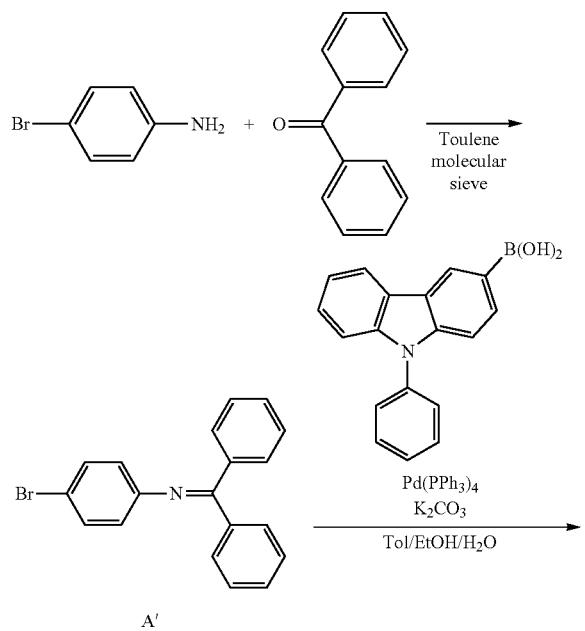

A'

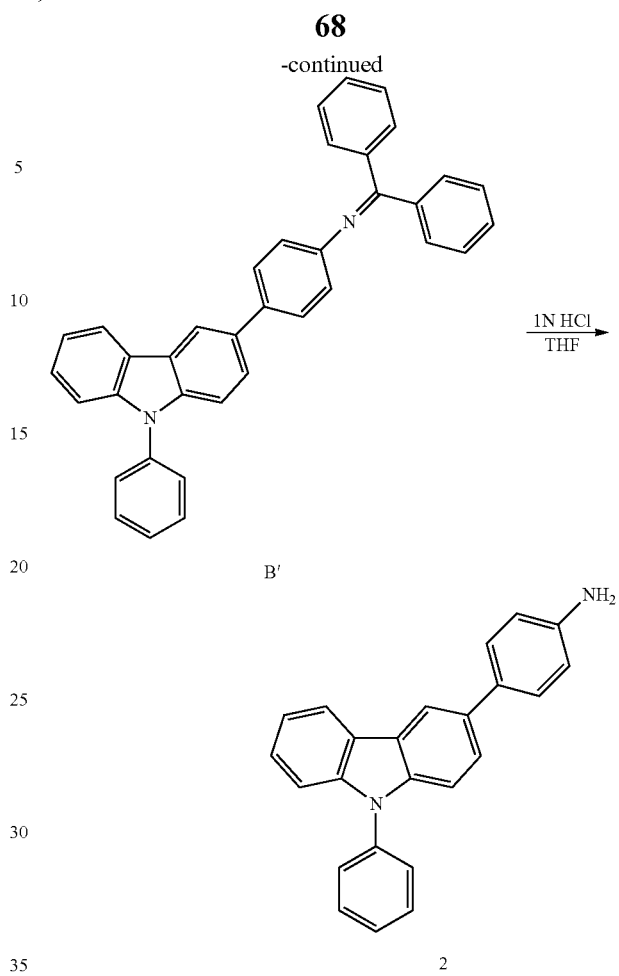

B'

2

In a 1 L 1-neck RBF, benzophenone (20 g, 109.8 mmol) and 4-bromoaniline (20.8 g, 120.7 mmol) were placed, and dissolved by introducing toluene (350 ml) thereto. Activated molecular sieves were introduced thereto, and the result was reacted for approximately 24 hours at 120° C. The temperature was lowered, and the molecular sieves were removed by filtering while washing with ether. The filtrate was concentrated, and recrystallized using methanol to obtain Compound A'.

In a 500 mL 1-neck RBF, (9-phenyl-9H-carbazol-3-yl) boronic acid (4.69 g, 16.4 mmol), A' (5 g, 14.87 mmol), K$_2$CO$_3$ (6.16 g, 44.6 mmol) and Pd(PPh$_3$)$_4$ (0.17 g, 0.15 mmol) were placed, and N$_2$ purged. Toluene (55 ml), ethanol (25 ml) and water (25 ml) were each introduced to dissolve the reactant, and after raising the temperature to 90° C. by installing a reflux, the result was reacted for approximately 18 hours. The reaction temperature was lowered, water was added thereto, and the organic layer was extracted using EA. The result was dried by introducing MgSO$_4$ thereto, and after adsorbing palladium by introducing charcoal thereto, the result was filtered with each of celite and silica, and then concentrated. The result was recrystallized with methanol to obtain Compound B'.

In a 250 mL 1-neck RBF, B' (7.3 g, 14.6 mmol) was placed, and dissolved by introducing THF (50 ml) thereto. 1 N HCl (approximately 0.2 ml) was introduced thereto, and the result was stirred for 3 hours at room temperature. An aqueous K$_2$CO$_3$ solution was introduced thereto to neutralize the reaction, and the organic layer was extracted using ethyl acetate (EA). The reaction solution was concentrated and columned to obtain Intermediate 2. An MS graph of Intermediate 2 is shown in FIG. 7.

3) Synthesis of Compound 1-1

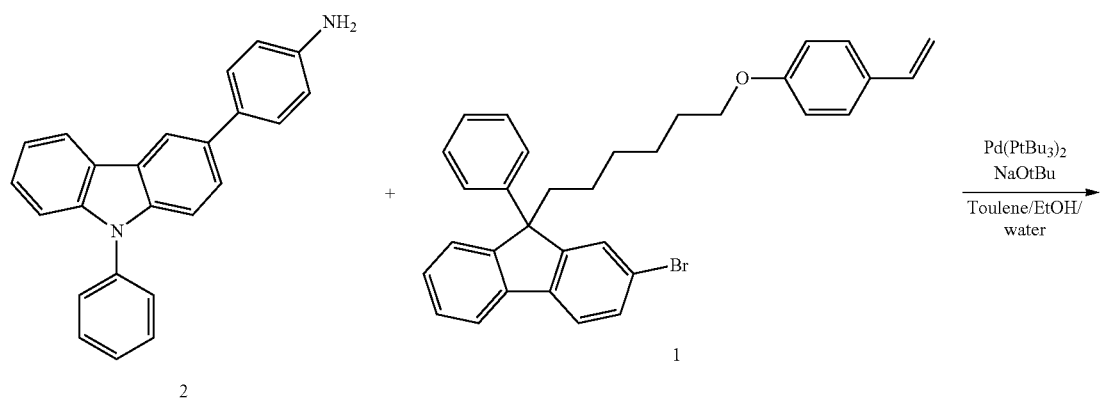

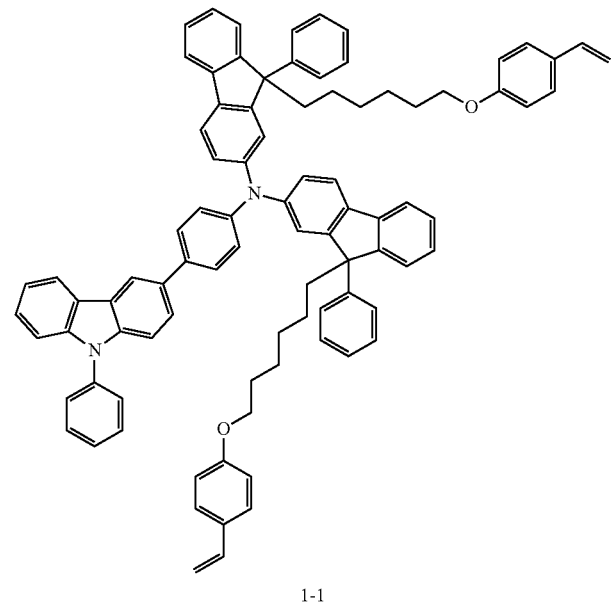

1-1

After Intermediate 2 (3.01 g, 5.74 mmol) was placed in a 100 mL 1-neck RBF and then dissolved in p-xylene (45 ml), the result was $N_2$ degassed. (RBF1) In a 100 mL 1-neck RBF, Intermediate 1 (0.94 g, 2.8 mmol), NaOtBu (1.34 g, 14 mmol) and $Pd(PtBu_3)_2$ (0.07 g, 0.14 mmol) were placed, and $N_2$ purged. (RBF2) The solution in RBF 1 was introduced to RBF 2 using a cannula, the reaction temperature was raised to 90° C., and the result was stirred for approximately 1 hour. After lowering the temperature to room temperature and precipitating the result in ethanol, a portion that was not dissolved was worked-up using water and EA. The organic layer was extracted, dried using $MgSO_4$, and after adsorbing palladium using charcoal, the result was filtered with each of celite and silica. The solution was concentrated and flash columned to obtain Compound 1-1.

FIG. 2 is a diagram showing a graph measuring Compound 1-1 using a differential scanning calorimeter (DSC), and FIG. 3 is a diagram showing MS data of Compound 1-1.

Preparation Example 2. Preparation of Compound 1-2

1) Synthesis of Intermediate 2

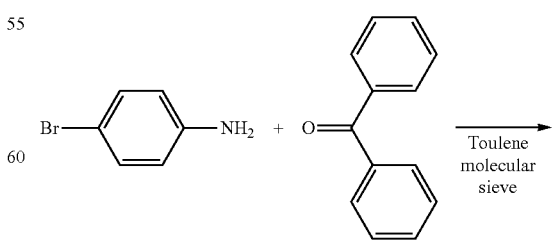

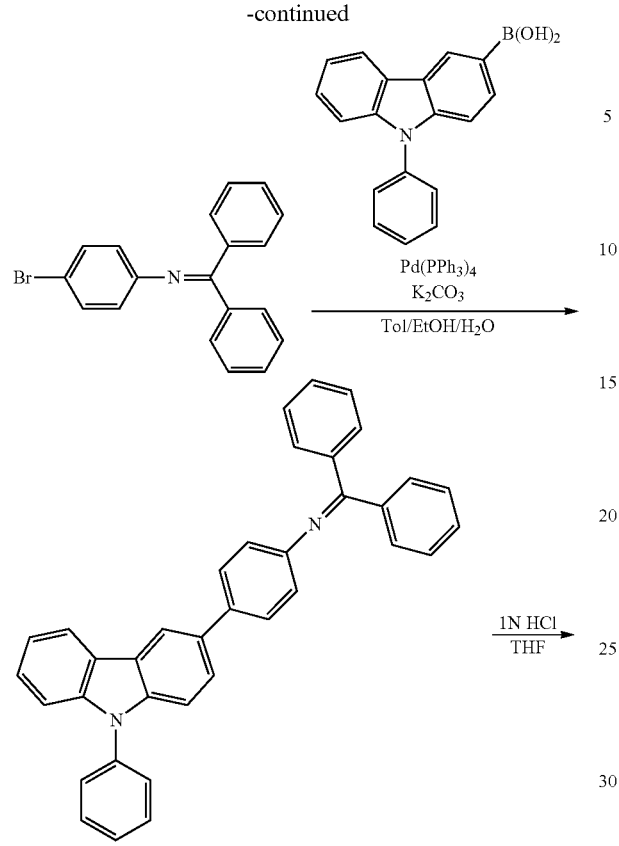
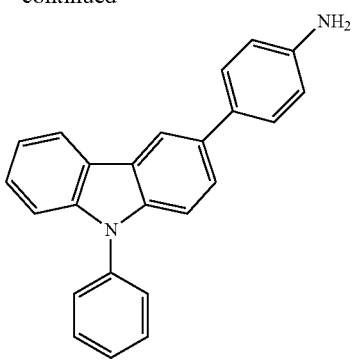
Intermediate 2 was prepared in the same manner as in the preparation of Compound 1-1.
2) Synthesis of Intermediate 3
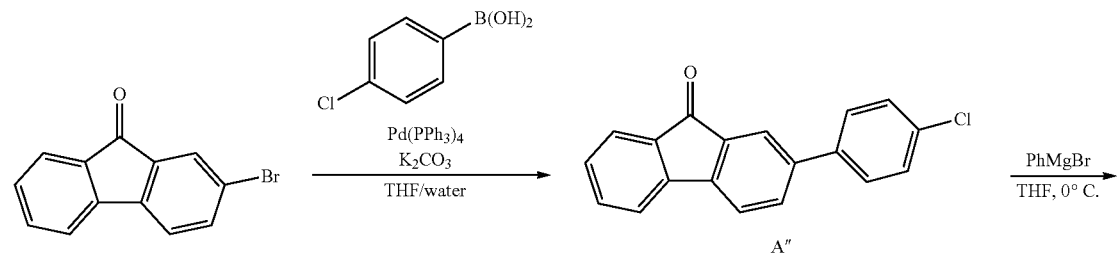
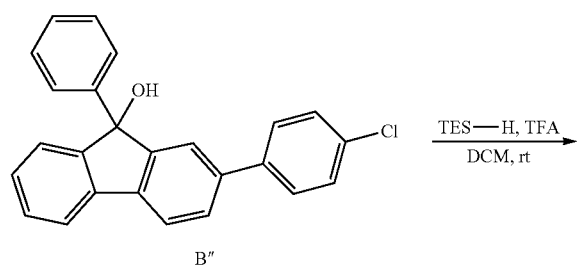

-continued

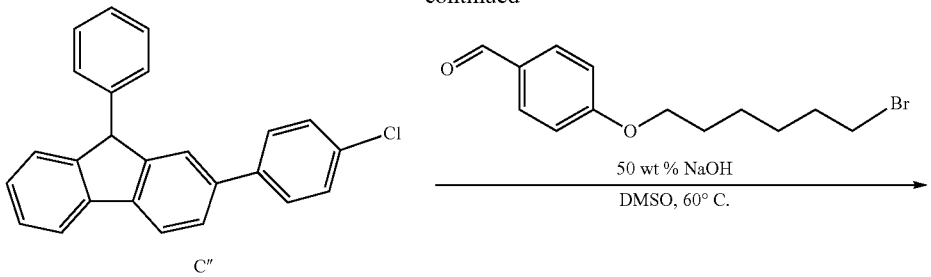

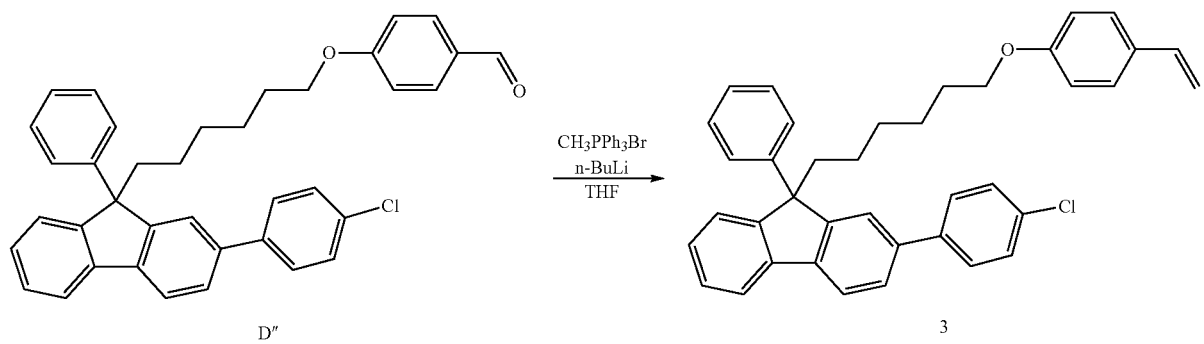

In a 250 mL 1-neck RBF, 2-bromo-9H-fluoren-9-one (5 g, 19.3 mmol), (4-chlorophenyl)boronic acid (3.3 g, 21.2 mmol), $K_2CO_3$ (8 g, 57.9 mmol) and $Pd(PPh_3)_4$ (0.22 g, 0.193 mmol) were placed, and dissolved by adding toluene, ethanol and water (60 ml, 20 ml and 20 ml, respectively) thereto. The temperature was raised up to 90° C., and the result was reacted for approximately 2 hours under reflux. The temperature was lowered, water was added thereto, and the organic layer was extracted with EA. The result was dried with $MgSO_4$, palladium was adsorbed using charcoal and removed, and the result was filtered with each of celite and silica. The reaction solution was concentrated, and recrystallized using methanol to obtain Compound A". Compound B" may be synthesized in the same manner as Compound A described above. Compound C" may be synthesized in the same manner as Compound B described above. Compound D" may be synthesized in the same manner as Compound C described above. Intermediate 3 may be synthesized in the same manner as Intermediate 2 described above. FIG. 8 is a diagram showing MS data of Intermediate 3.

3) Synthesis of Compound 1-2

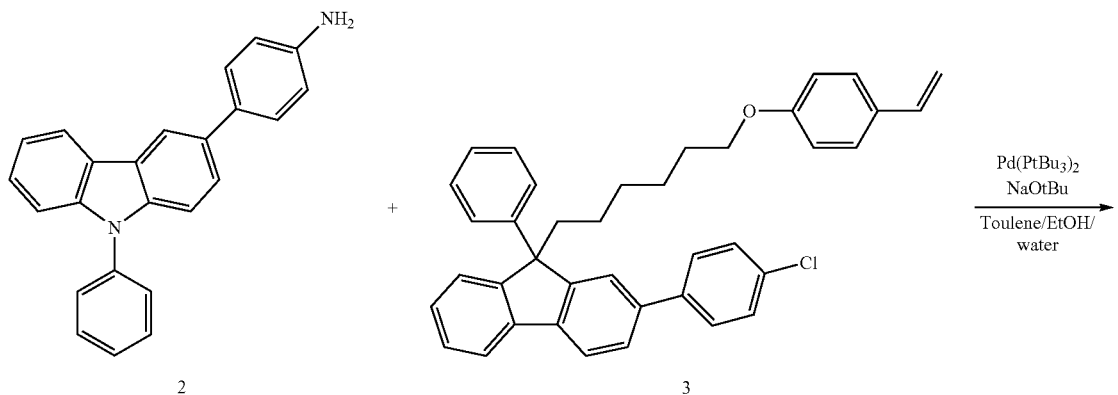

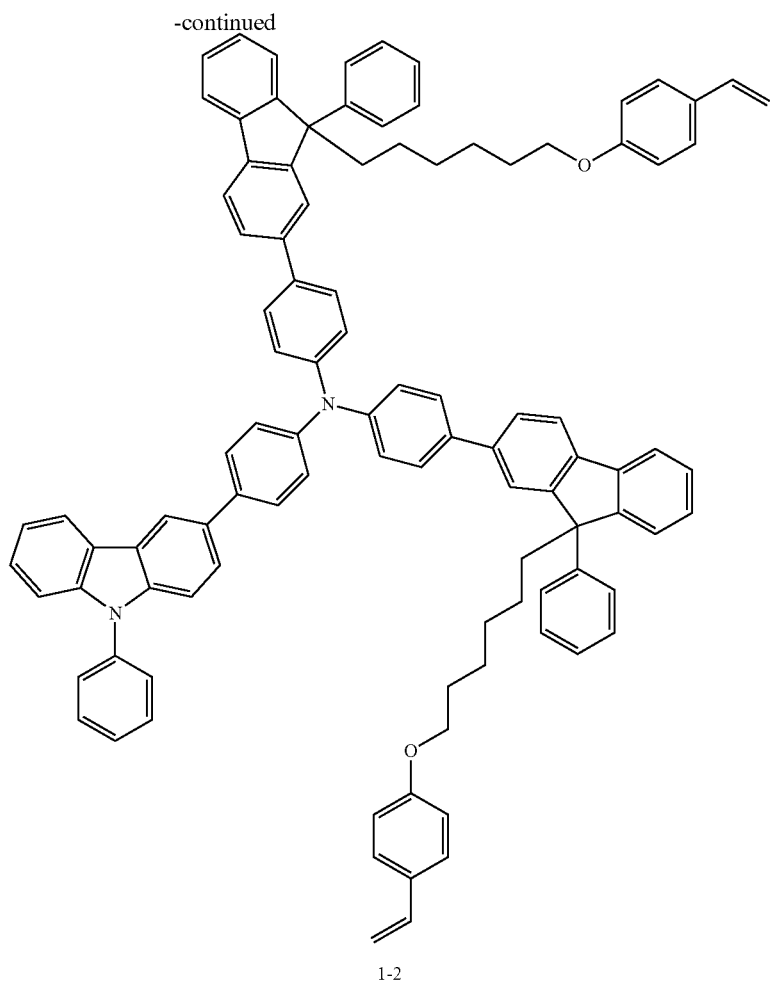
1-2
Compound 1-2 was synthesized in the same manner as in the synthesis method of Compound 1-1 except that Intermediate 3 was used instead of Intermediate 1.
Preparation Example 3. Preparation of Compound 1-3
1) Synthesis of Intermediate 1
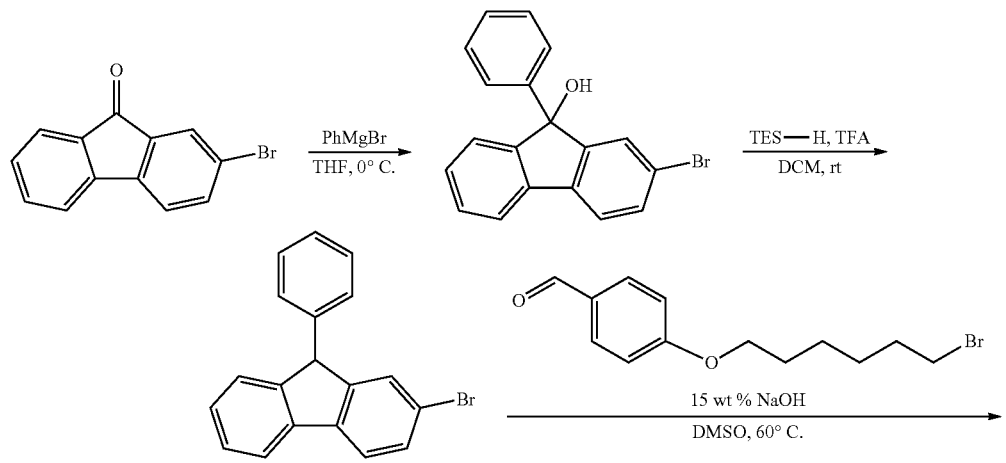

-continued
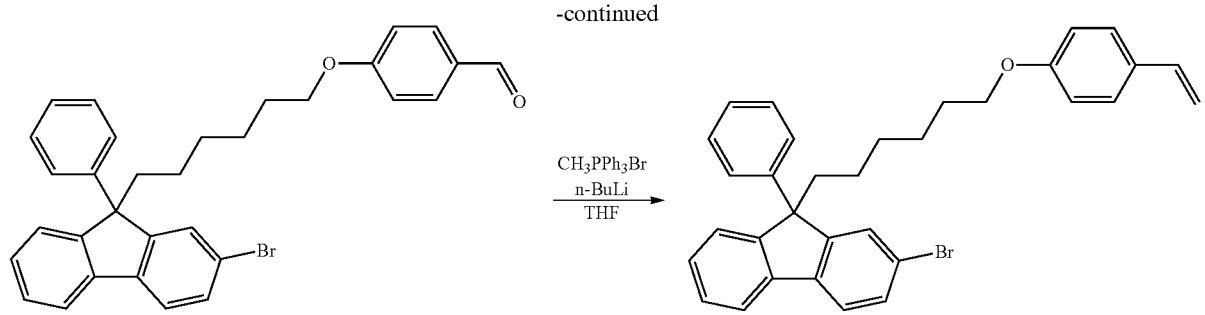
Intermediate 1 was prepared in the same manner as in the preparation of Compound 1-1.
2) Synthesis of Compound 1-3
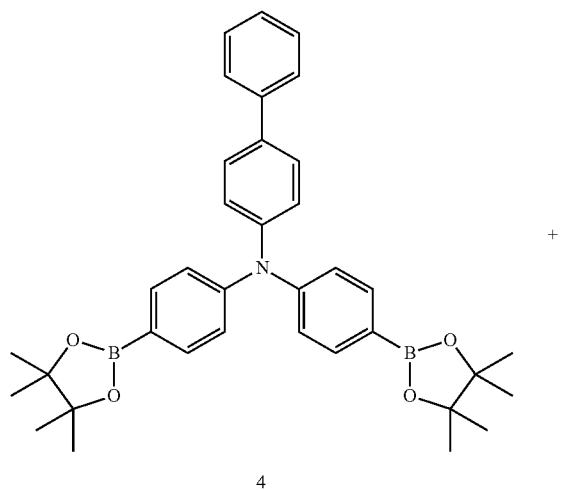
4
+
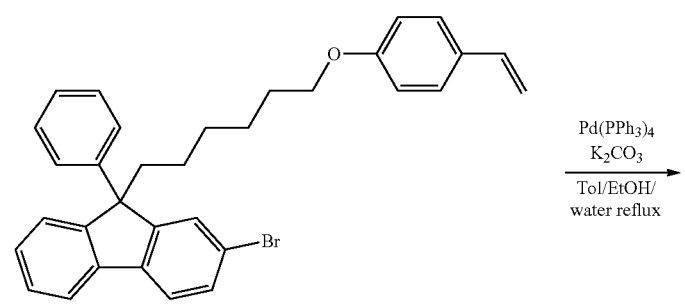
1
Pd(PPh₃)₄
K₂CO₃
Tol/EtOH/
water reflux

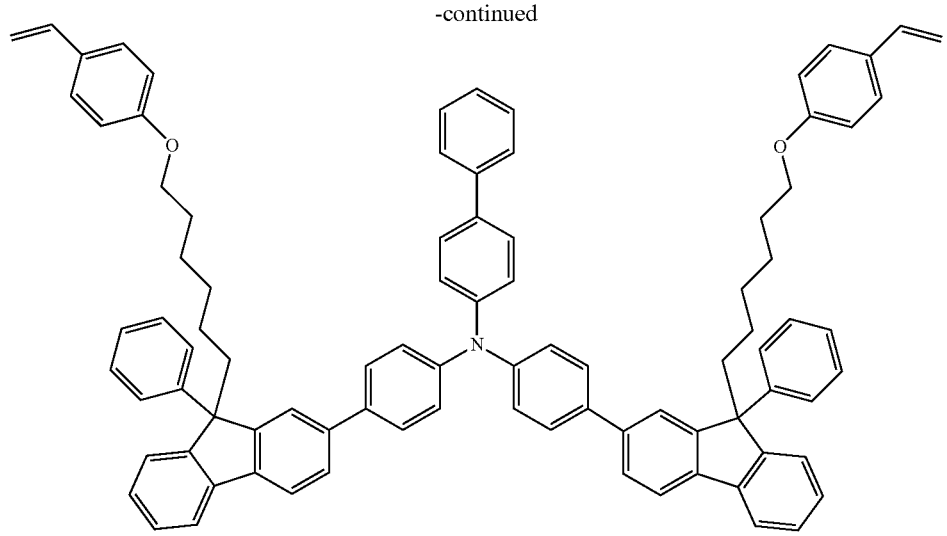

1-3

In a 250 mL 1-neck RBF, N,N-bis(4-(4,4,5,5-tetramethyl-1,3,2-dioxaborolan-2-yl)phenyl)-[1,1'-biphenyl]-4-amine (1.64 g, 2.86 mmol), Intermediate 1 (3 g, 5.7 mmol), $K_2CO_3$ (1.58 g, 11.44 mmol) and $Pd(PPh_3)_4$ (0.03 g, 0.028 mmol) were placed, and dissolved by adding toluene, ethanol and water (20 ml, 5 ml and 5 ml, respectively) thereto. The temperature was raised up to 90° C., and the result was reacted for approximately 2 hours under reflux. The temperature was lowered, water was added thereto, and the organic layer was extracted with EA. The result was dried with $MgSO_4$, palladium was adsorbed using charcoal and removed, and the result was filtered with each of celite and silica. The reaction solution was concentrated, and flash columned to synthesize Compound 1-3.

FIG. 4 is a diagram showing a graph measuring Compound 1-3 using a differential scanning calorimeter (DSC), and FIG. 5 is a diagram showing MS data of Compound 1-3.

Experimental Example

Experimental Example 1. Experiment on Film Retention Rate

Example 1-1

Compound 1-1 (20 mg) was dissolved in cyclohexanone (1 ml). The obtained solution was spin coated on a glass substrate for 1 minute at 1200 rpm. The result was heat treated for 2 minutes at 80° C. and 30 minutes at 200° C. under nitrogen atmosphere, and then cooled at room temperature to prepare a thin film.

Example 1-2

A thin film was prepared in the same manner as in Example 1-1 except that Compound 1-2 was used instead of Compound 1-1.

Example 1-3

A thin film was prepared in the same manner as in Example 1-1 except that Compound 1-3 was used instead of Compound 1-1.

Comparative Example 1-1

A thin film was prepared in the same manner as in Example 1-1 except that the following Compound A was used instead of Compound 1-1.

[Compound A]

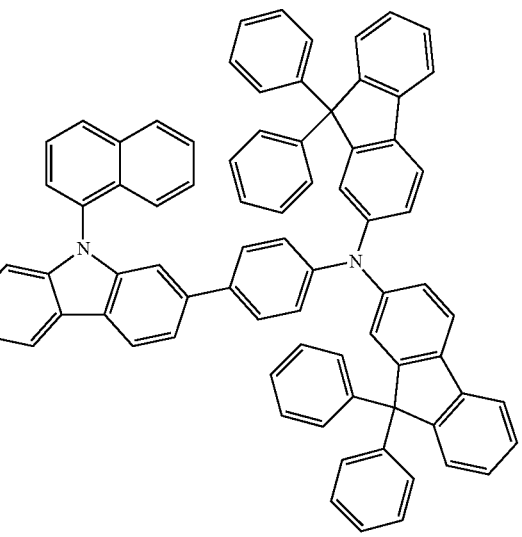

Comparative Example 1-2

A thin film was prepared in the same manner as in Example 1-1 except that the following Compound B was used instead of Compound 1-1.

[Compound B]

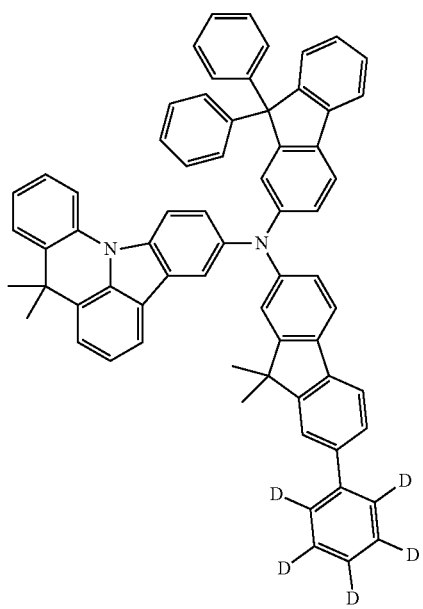

A film retention rate of each of the thin films prepared in Examples 1-1 to 1-3 and Comparative Examples 1-1 and 1-2 was measured. The film retention rate was obtained by measuring a UV spectrum of the thin film without any treatment, measuring a UV spectrum after dipping the thin film in toluene for 10 minutes, and comparing the λmax values. In the following Table 1, measured values of the film retention rates of Examples 1-1 to 1-3 and Comparative Examples 1-1 and 1-2 are described, and in FIG. 9 to FIG. 13, graphs measuring UV spectra before/after dipping each of the thin films of Examples 1-1 to 1-3 and Comparative Examples 1-1 and 1-2 in toluene are shown. In FIGS. 9 to 13, the vertical axis means optical density (OD). The film retention rate was calculated by the following equation.

Film retention rate (%)=λmax value after dipping in toluene/λmax value before dipping in toluene× 100

TABLE 1

| | Film Retention Rate (%) |
| --- | --- |
| Example 1-1 | 100 |
| Example 1-2 | 100 |

TABLE 1-continued

| | Film Retention Rate (%) |
| --- | --- |
| Example 1-3 | 99 |
| Comparative Example 1-1 | 0 |
| Comparative Example 1-2 | 0 |

In a solution process, when a hole transfer layer material is dissolved in a solvent used for forming each adjacent layer in light emitting device manufacture, a design to avoid the material from being dissolved in the solvent is required. For this, the hole transfer layer material preferably has a crosslinking group, and preferably becomes insoluble by being crosslinked at a heat treatment temperature range of the hole transfer layer (process temperature of 80° C. to 220° C.)

In Table 1, it was seen that, in Examples 1-1 to 1-3, the films were retained through being sufficiently crosslinked at 200° C. compared to Comparative Examples 1-1 and 1-2 that did not have a crosslinking group.

Experimental Example 2. Manufacture of Organic Light Emitting Device

Example 2-1

A glass substrate on which indium tin oxide (ITO) was coated as a thin film to a thickness of 1,500 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer having a thickness of 400 Å was formed by spin coating a composition mixing VNPB and a p-dopant (the following Chemical Formula 6) in a weight ratio of 0.8:0.2, and curing the result under a condition of 220° C. and 30 minutes on a hot plate under nitrogen atmosphere.

On the hole injection layer formed as above, a hole transfer layer having a thickness of 200 Å was formed by spin coating a solution dissolving Compound 1-1 in toluene, and curing the result under a condition of 200° C. and 30 minutes on a hot plate.

On the hole transfer layer formed as above, a light emitting layer having a thickness of 550 Å was formed by spin coating a solution dissolving the following Compound C in toluene, and heat treating the result for 30 minutes at 180° C.

This was introduced into a vacuum depositor, and when the base pressure became $2\times10^{-5}$ Pa or lower, LiF (10 Å) and Al (1,000 Å) were consecutively deposited to manufacture an organic light emitting device. In the above-mentioned process, the deposition rate of the LiF was maintained at 0.01 nm/s to 0.05 nm/s, and the deposition rates of the materials other than the LiF were maintained at 0.1 nm/s to 0.5 nm/s.

[VNPB]

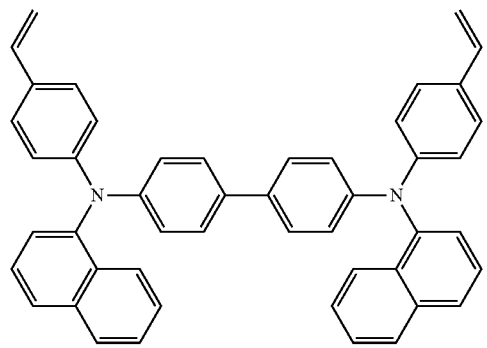

Chemical Formula 6

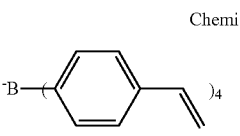

Compound C

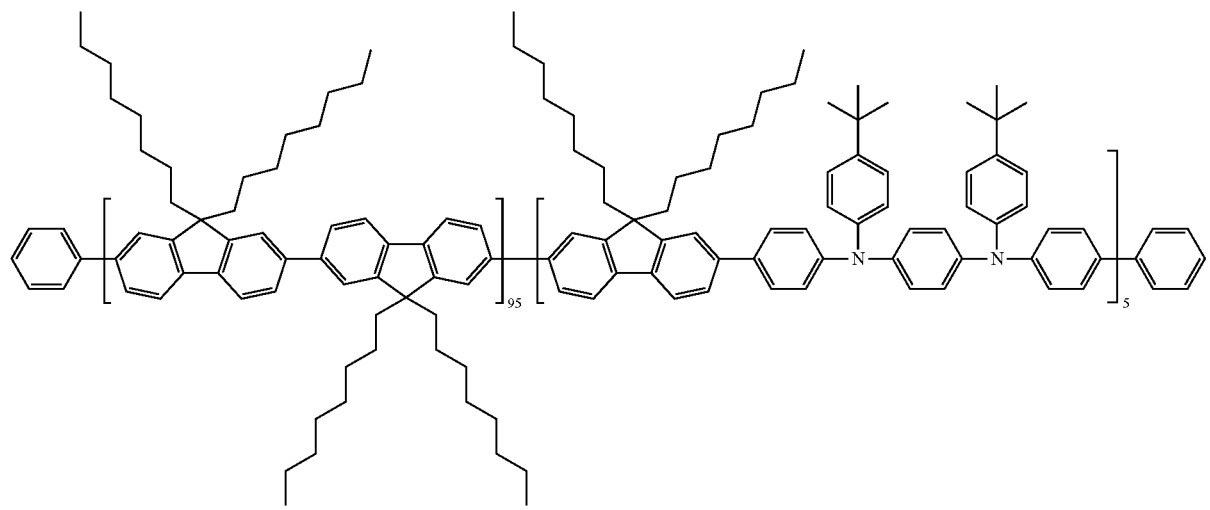

Example 2-2

An organic light emitting device was manufactured in the same manner as in Example 2-1 except that Compound 1-2 was used instead of Compound 1-1.

Example 2-3

An organic light emitting device was manufactured in the same manner as in Example 2-1 except that Compound 1-3 was used instead of Compound 1-1.

Comparative Example 2-1

An organic light emitting device was manufactured in the same manner as in Example 2-1 except that the following Compound A was used instead of Compound 1-1.

[Compound A]

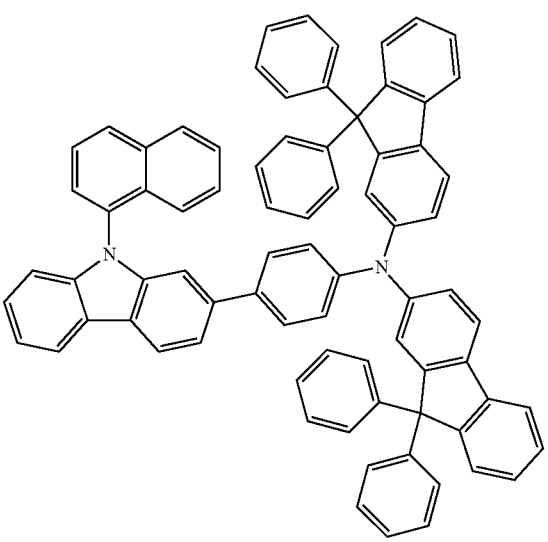

Comparative Example 2-2

An organic light emitting device was manufactured in the same manner as in Example 2-1 except that the following Compound B was used instead of Compound 1-1.

[Compound B]

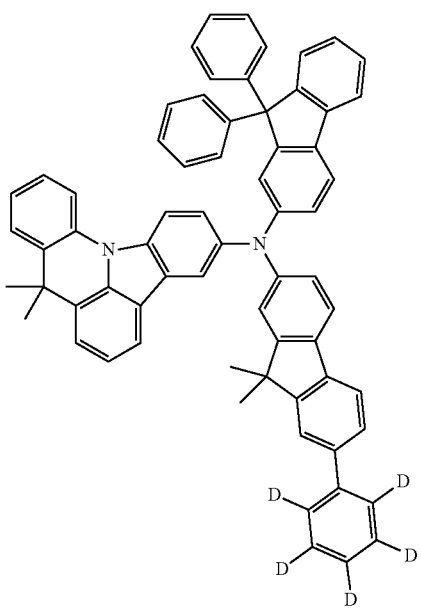

For the organic light emitting devices manufactured in Examples 2-1 to 2-3 and Comparative Example 2-1, driving voltage and light emission efficiency were measured at current density of 10 mA/cm$^2$, and time taken for the luminance decreasing to 95% compared to its initial luminance (T$_{95}$) was measured at current density of 10 mA/cm$^2$. The results are shown in the following Table 2.

TABLE 2

| | Voltg. (V) | Current Density (mA/cm) | Voltage Efficiency (Cd/A) | Power Efficiency (lm/A) | Quantum Efficiency (%) | Luminance (Cd/m$^2$) | CIEx | CIEy | T95 |
|---|---|---|---|---|---|---|---|---|---|
| Example 2-1 | 4.72 | 10 | 3.76 | 2.50 | 4.05 | 376.0 | 0.137 | 0.105 | 46.5 |
| Example 2-2 | 4.5 | 10 | 3.37 | 2.35 | 3.63 | 337.12 | 0.141 | 0.1 | 45.3 |
| Example 2-3 | 4.49 | 10 | 3.29 | 2.3 | 3.67 | 328.79 | 0.14 | 0.096 | 35.2 |
| Comparative Example 2-1 | 11.48 | 10 | 2.05 | 0.56 | 1.74 | 0.156 | 0.143 | 0.132 | — |
| Comparative Example 2-2 | 10.4 | 10 | 2.15 | 0.65 | 2.34 | 215 | 0.141 | 0.129 | — |

As described in Table 2, it was identified that the organic light emitting devices manufactured in Examples 2-1 to 2-3 of the present application had a lower driving voltage, and had excellent efficiency, luminance and lifetime properties compared to the organic light emitting devices manufactured in Comparative Examples 2-1 and 2-2.

The invention claimed is:

1. A compound represented by the following Chemical Formula 1:

[Chemical Formula 1]

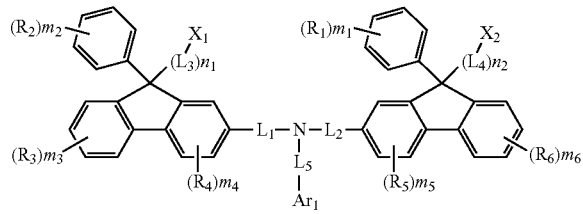

wherein, in Chemical Formula 1, $L_1$ and $L_2$ are the same as or different from each other, and each independently a direct bond; a substituted or unsubstituted arylene group; or a substituted or unsubstituted heteroarylene group;

$L_3$ and $L_4$ are the same as or different from each other, and each independently a direct bond; or a substituted or unsubstituted alkylene group;

$L_5$ is a direct bond; or a substituted or unsubstituted arylene group;

$R_1$ to $R_6$ are the same as or different from each other, and each independently hydrogen; deuterium; a halogen group; a nitrile group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted aryl group; a substituted or unsubstituted alkylamine group; a substituted or unsubstituted arylamine group; a substituted or unsubstituted heteroarylamine group; a substituted or unsubstituted arylheteroarylamine group; or a substituted or unsubstituted heteroaryl group;

$Ar_1$ is hydrogen; a substituted or unsubstituted aryl group; a substituted or unsubstituted alkylamine group; a substituted or unsubstituted arylamine group; a substituted or unsubstituted heteroarylamine group; a substituted or unsubstituted arylheteroarylamine group; or a substituted or unsubstituted heteroaryl group;

$X_1$ and $X_2$ are the same as or different from each other, and each independently a functional group crosslinkable by heat or light;

$n_1$ and $n_2$ are each an integer of 0 to 12;

$m_1$ and $m_2$ are each an integer of 0 to 5;

$m_3$ and $m_6$ are each an integer of 0 to 4; and $m_4$ and $m_5$ are each an integer of 0 to 3.

2. The compound of claim 1, wherein the functional group crosslinkable by heat or light of $X_1$ and $X_2$ is any one of the following structures:

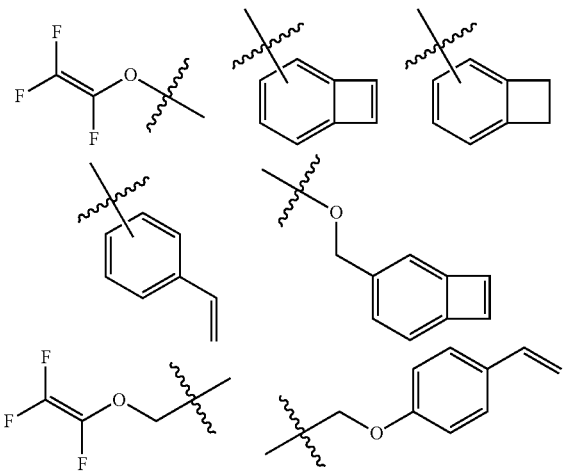

-continued

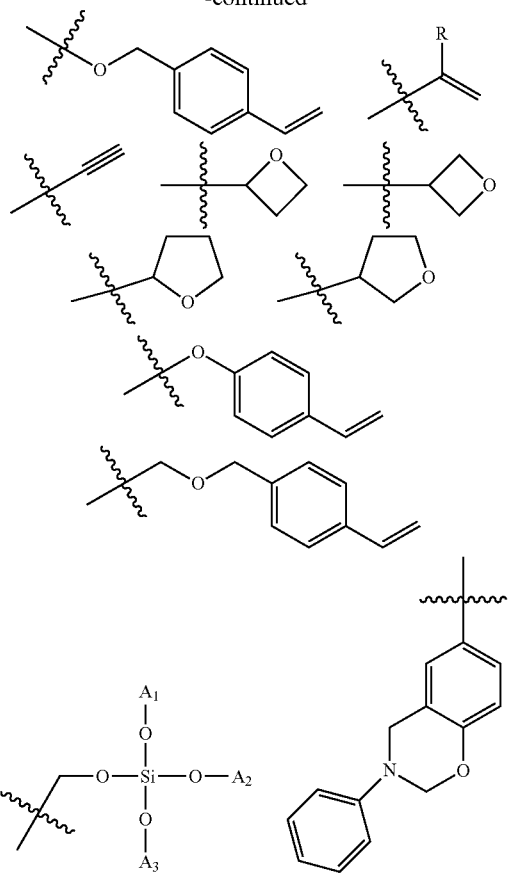

-continued

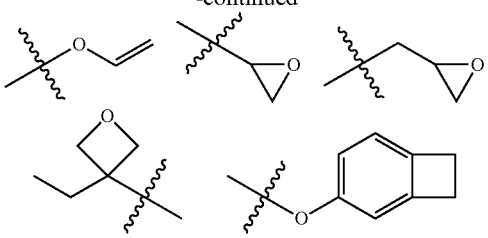

in the structures,

R is hydrogen; or a substituted or unsubstituted alkyl group; and $A_1$ to $A_3$ are the same as or different from each other, and each independently a substituted or unsubstituted alkyl group having 1 to 6 carbon atoms.

3. The compound of claim 1, wherein $L_1$ and $L_2$ are the same as or different from each other, and each independently a direct bond; a substituted or unsubstituted phenylene group; a substituted or unsubstituted biphenylylene group; or a substituted or unsubstituted naphthylene group.

4. The compound of claim 1, wherein $Ar_1$ is hydrogen; a substituted or unsubstituted aryl group; a substituted or unsubstituted arylamine group; or a substituted or unsubstituted heteroaryl group.

5. The compound of claim 1, wherein the compound represented by Chemical Formula 1 is any one selected from among the following structures:

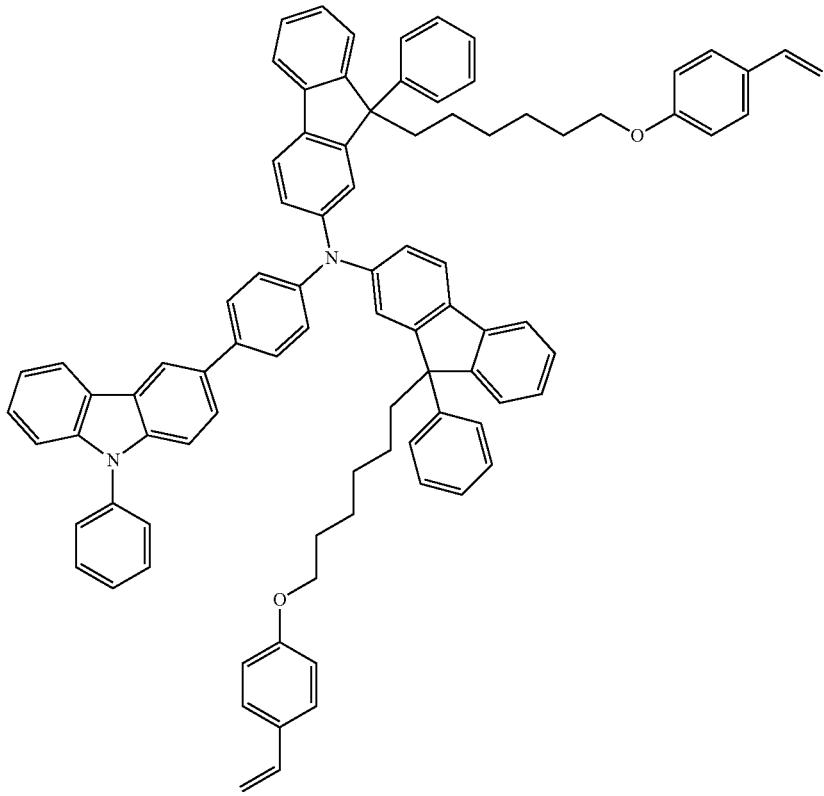

89
90
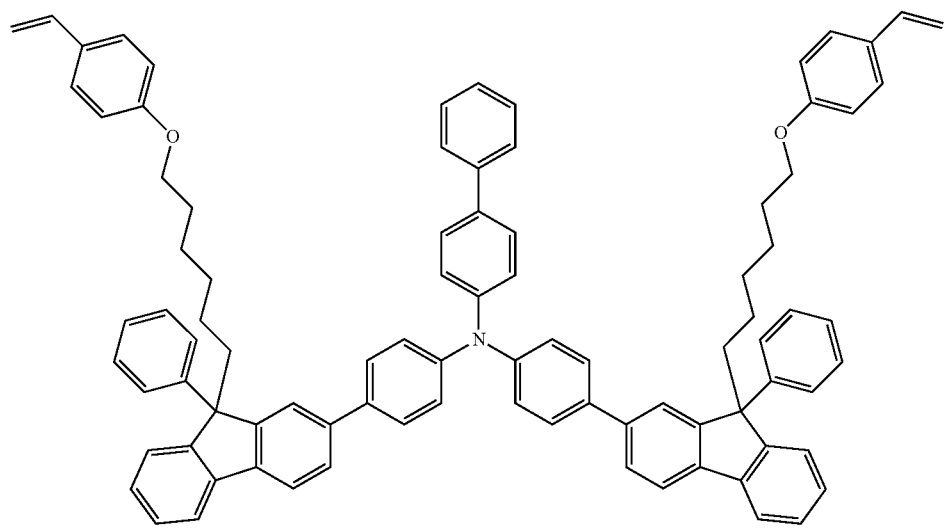
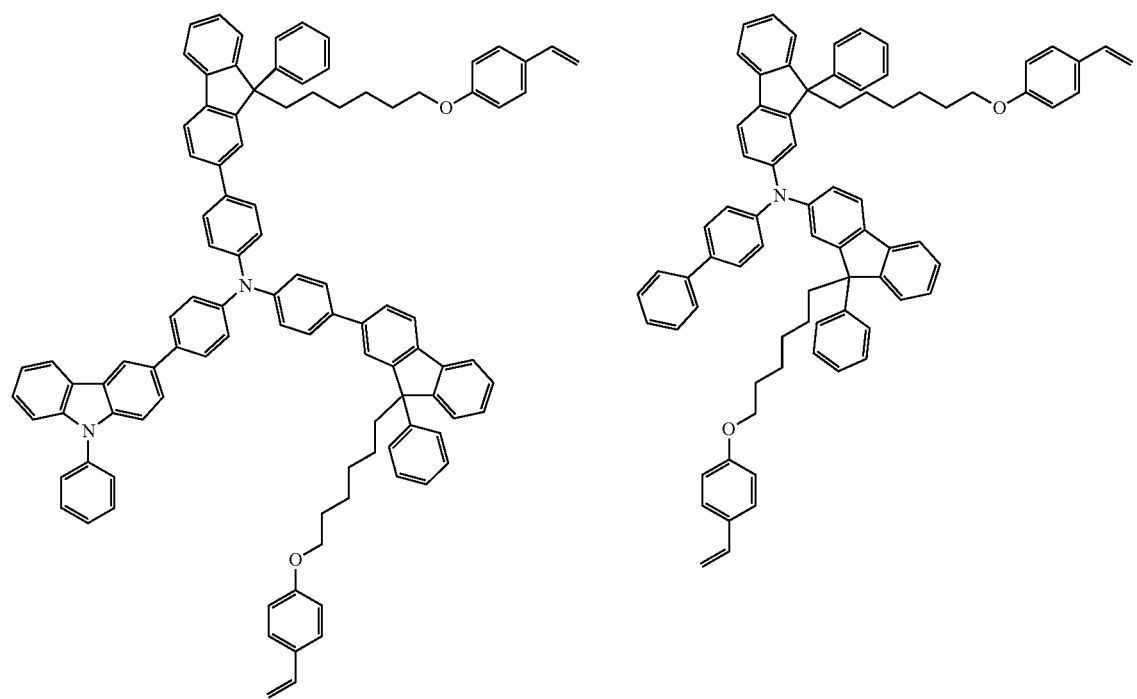

91
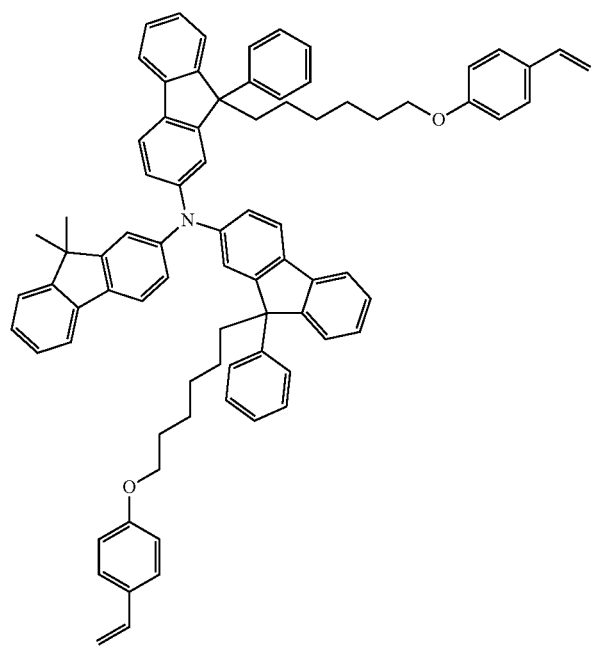
92
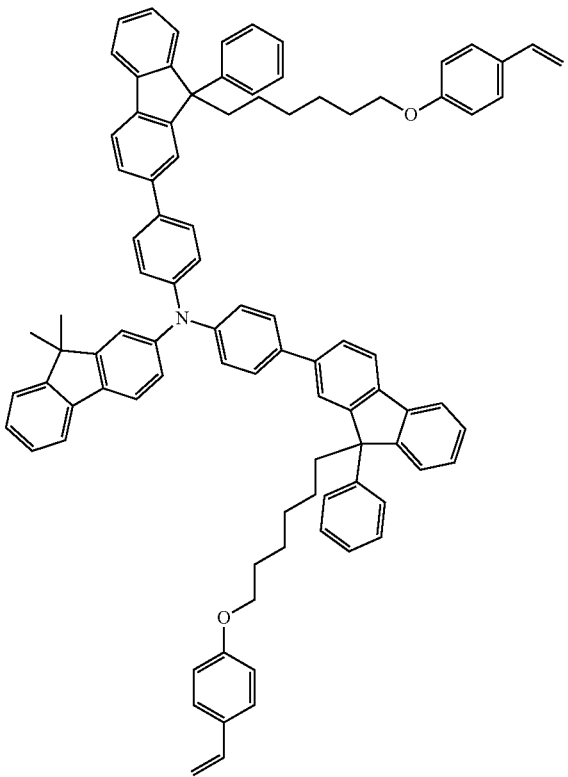
-continued
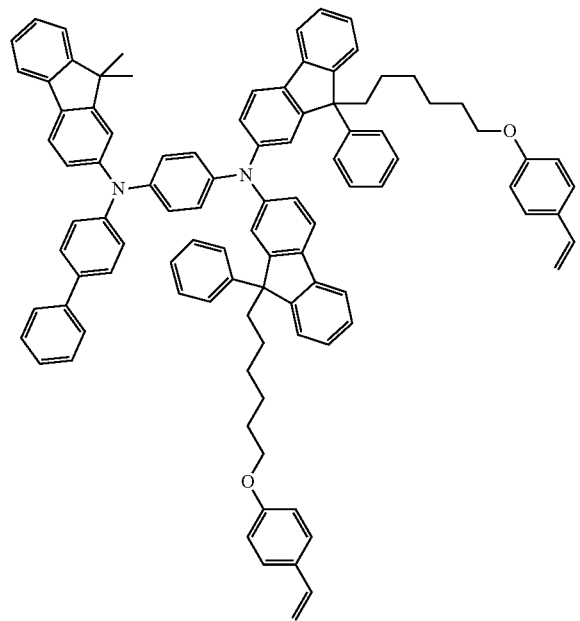
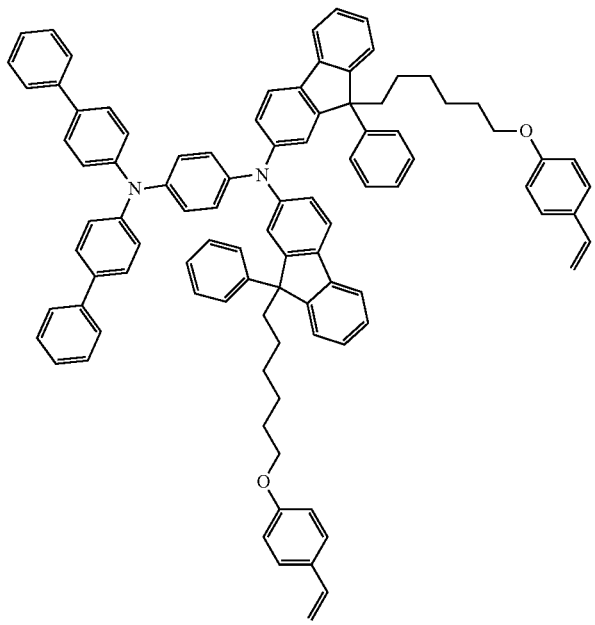

-continued
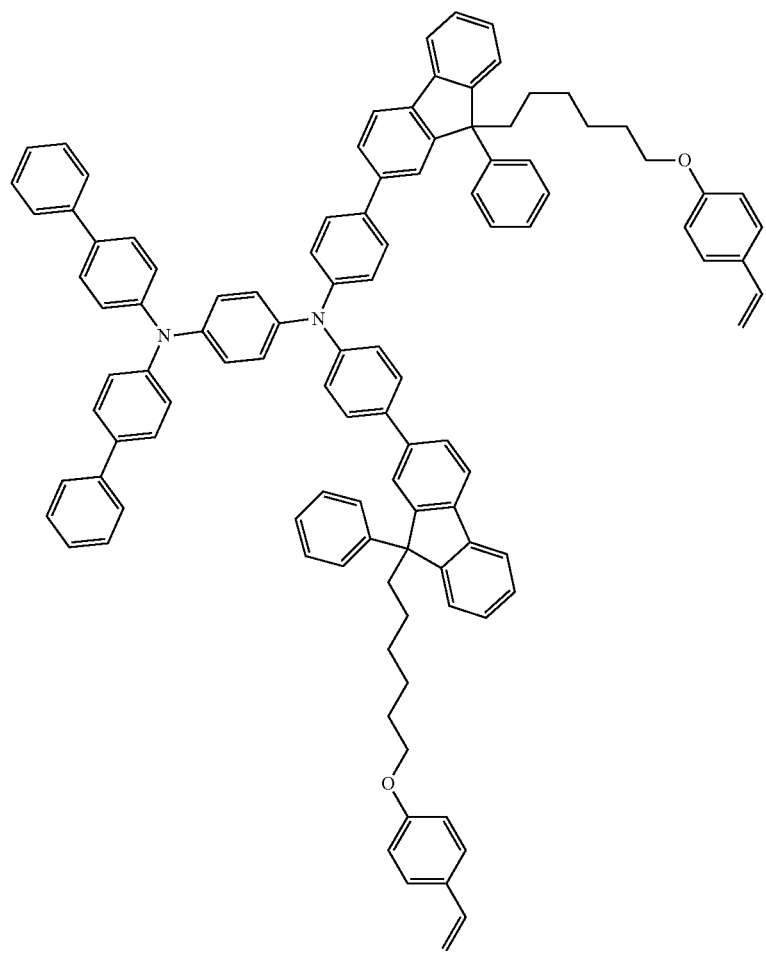
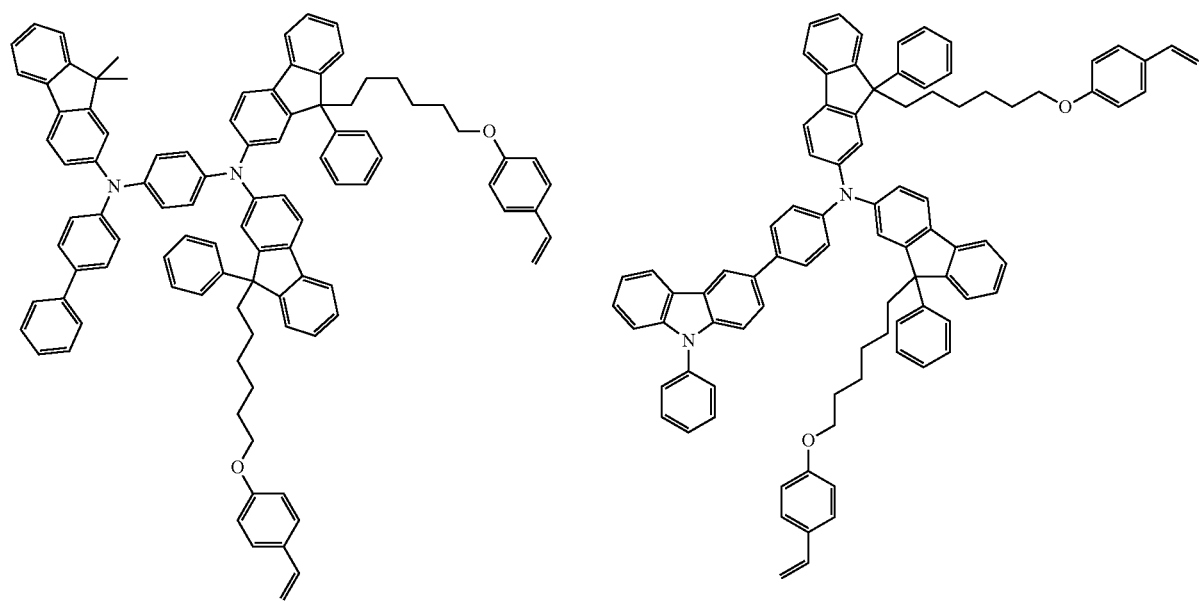

95
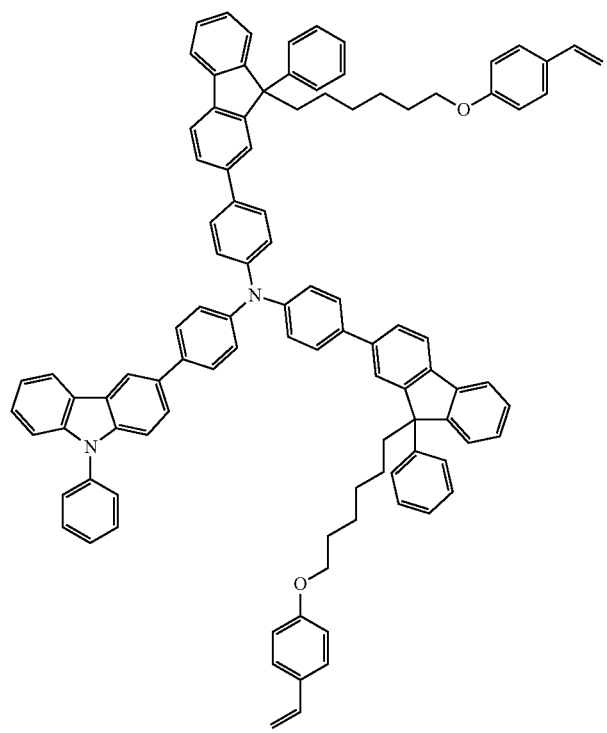
96
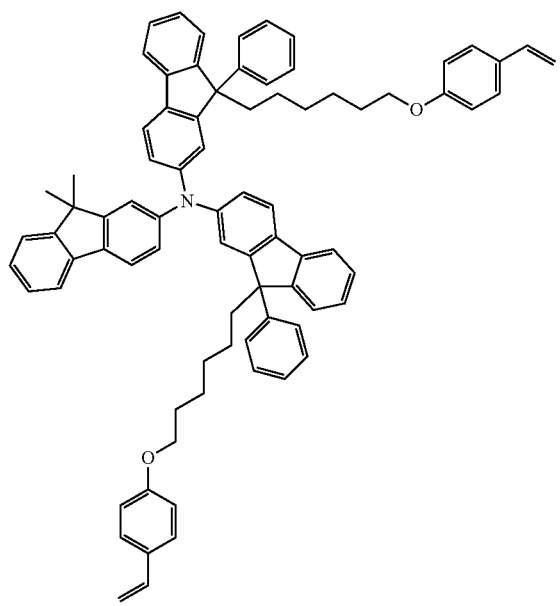
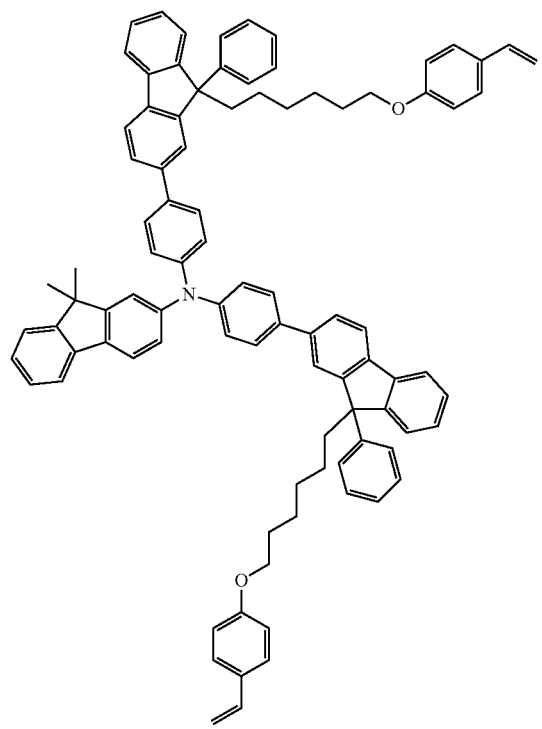
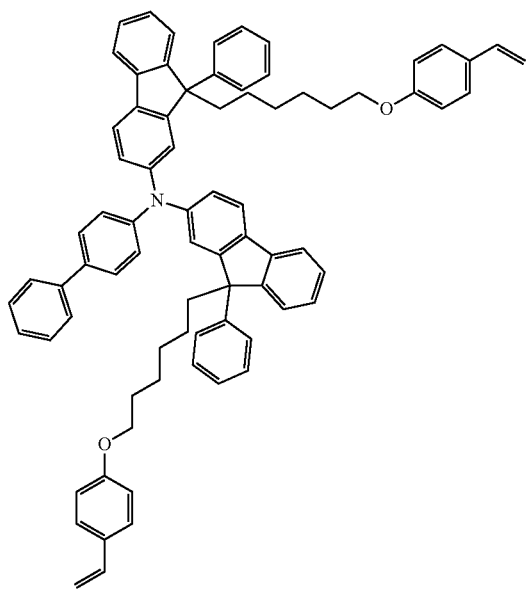

-continued
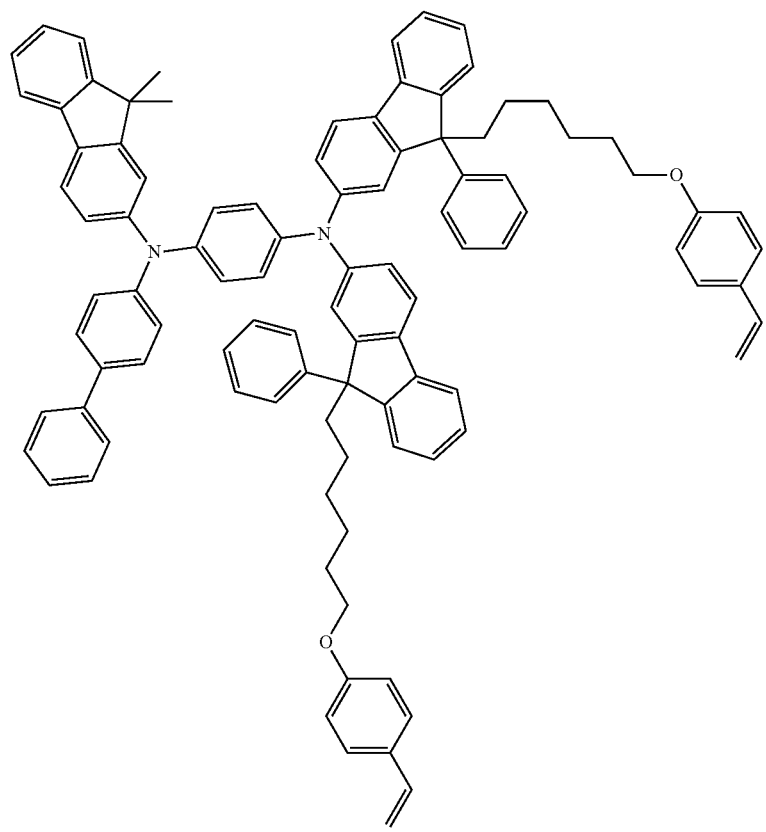
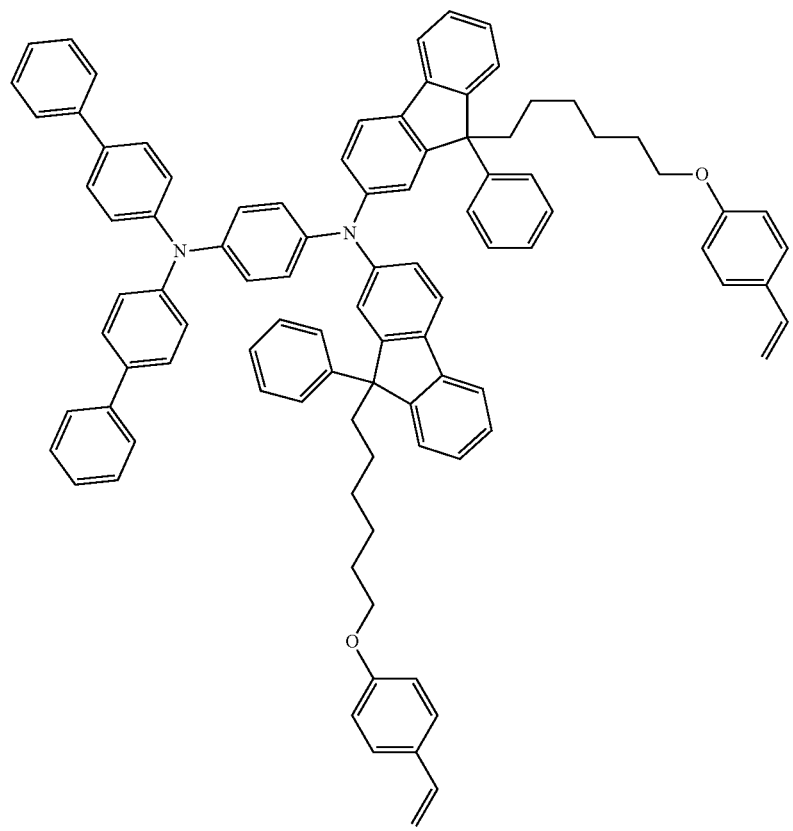

-continued
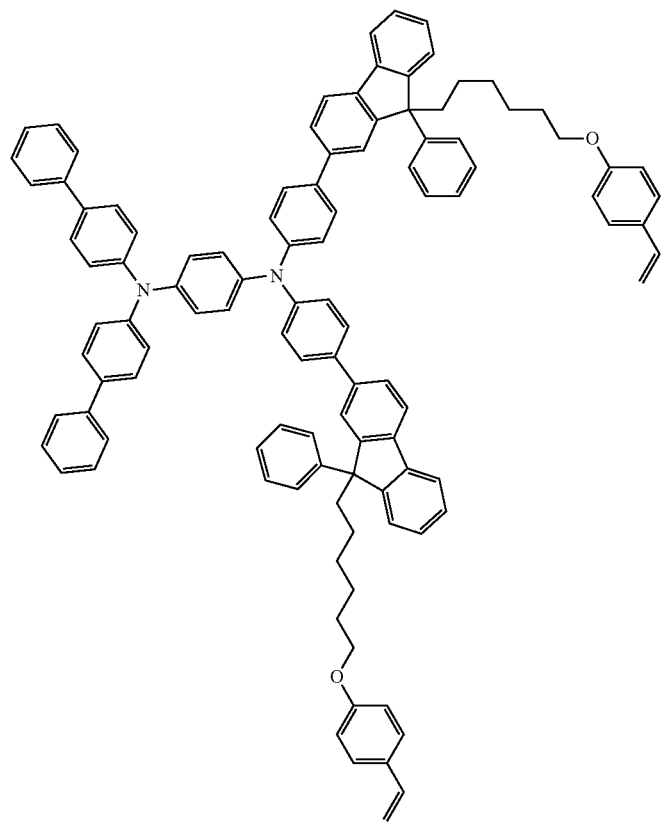
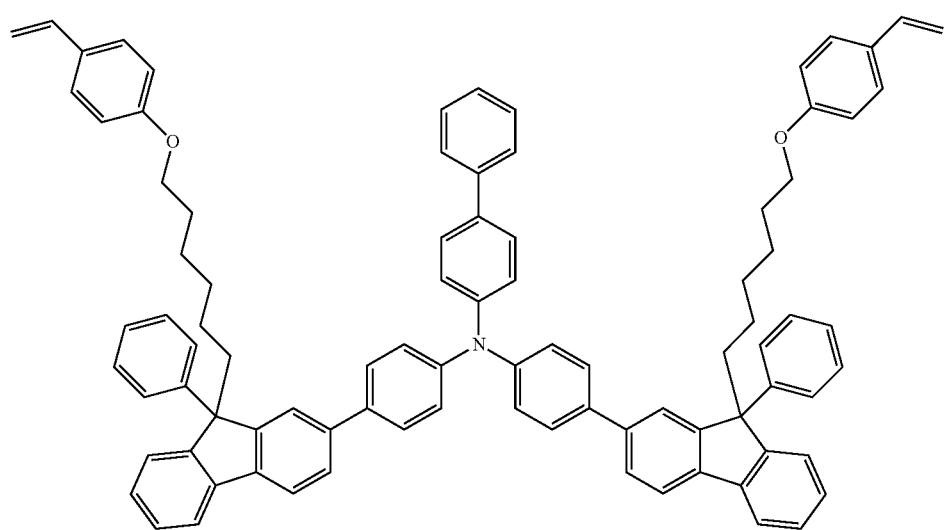

101
-continued
102
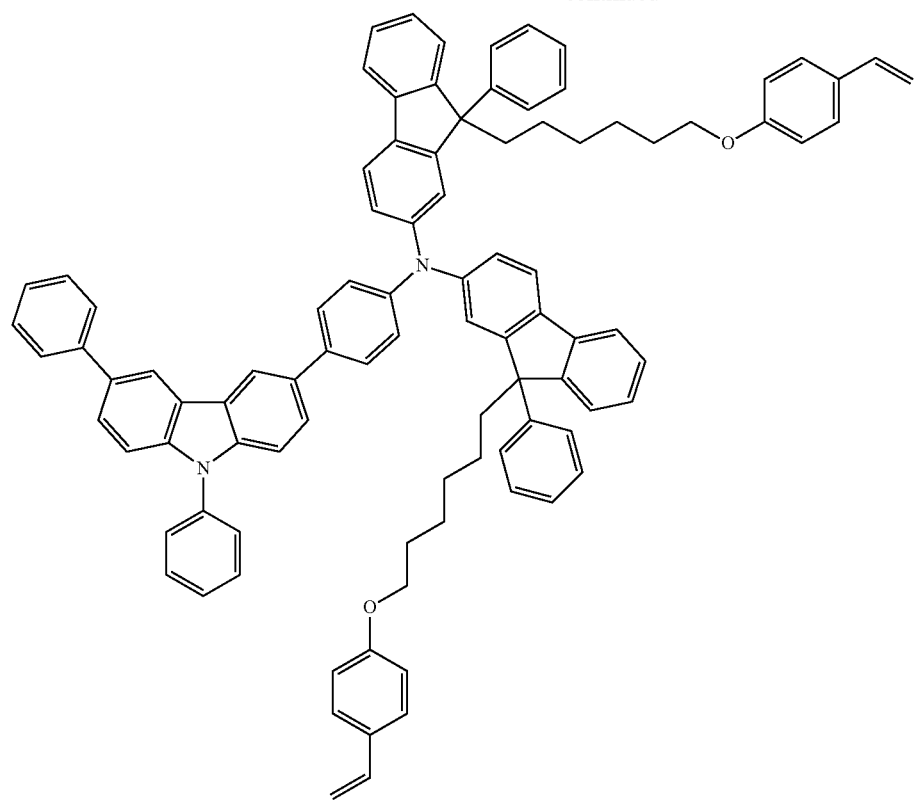
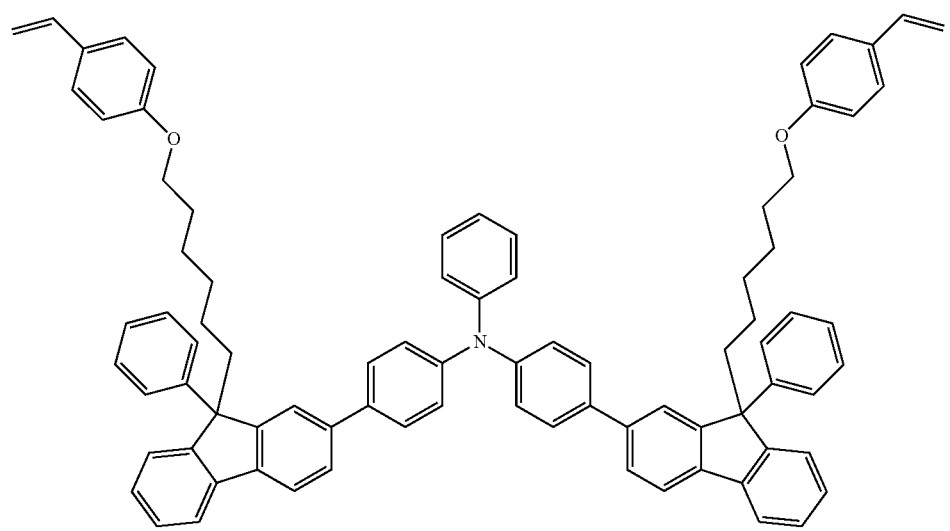

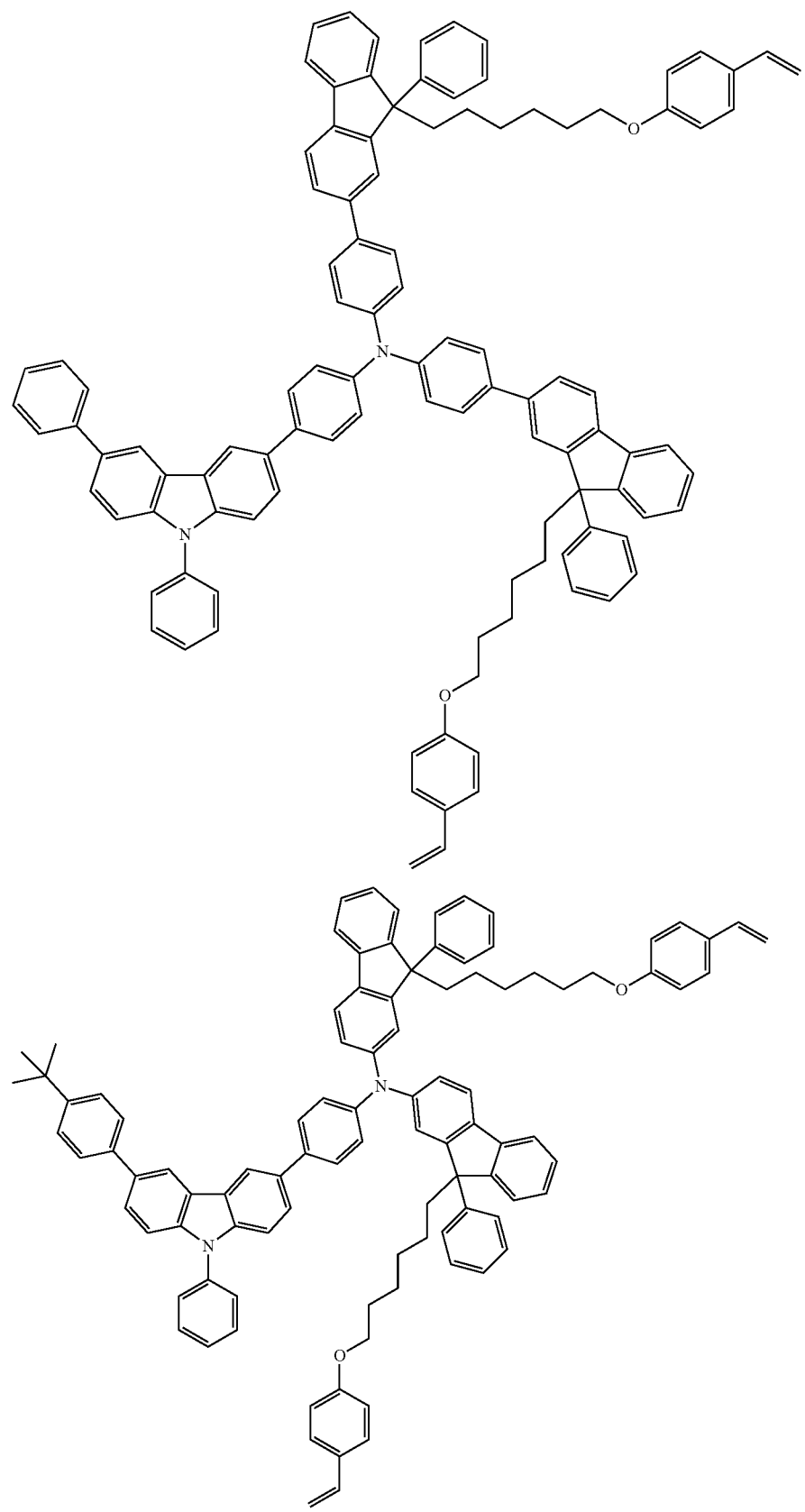

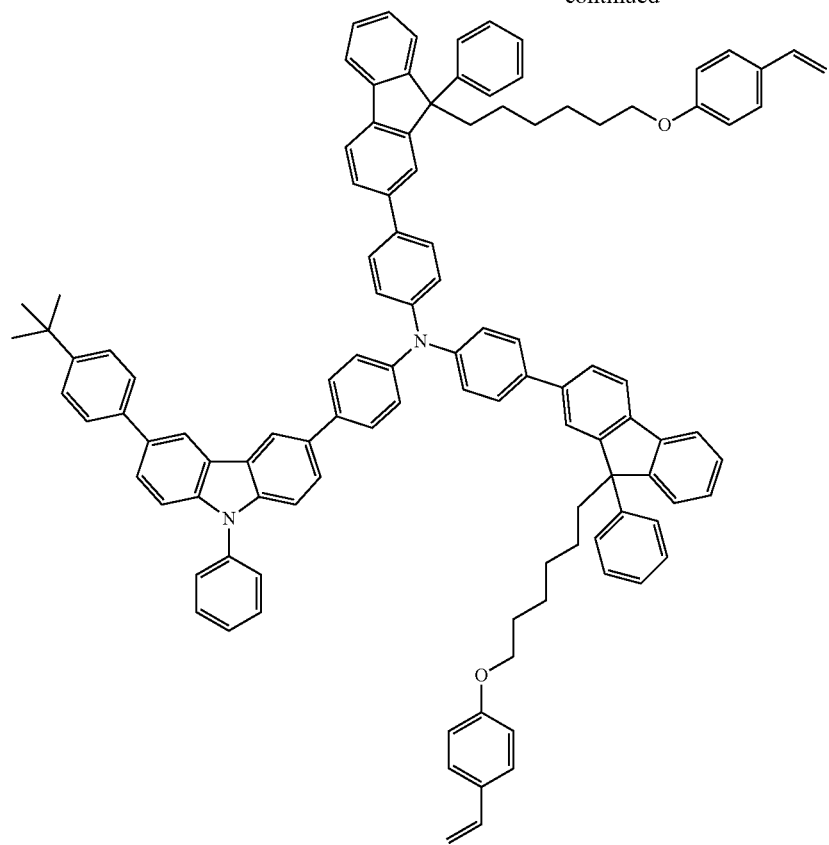
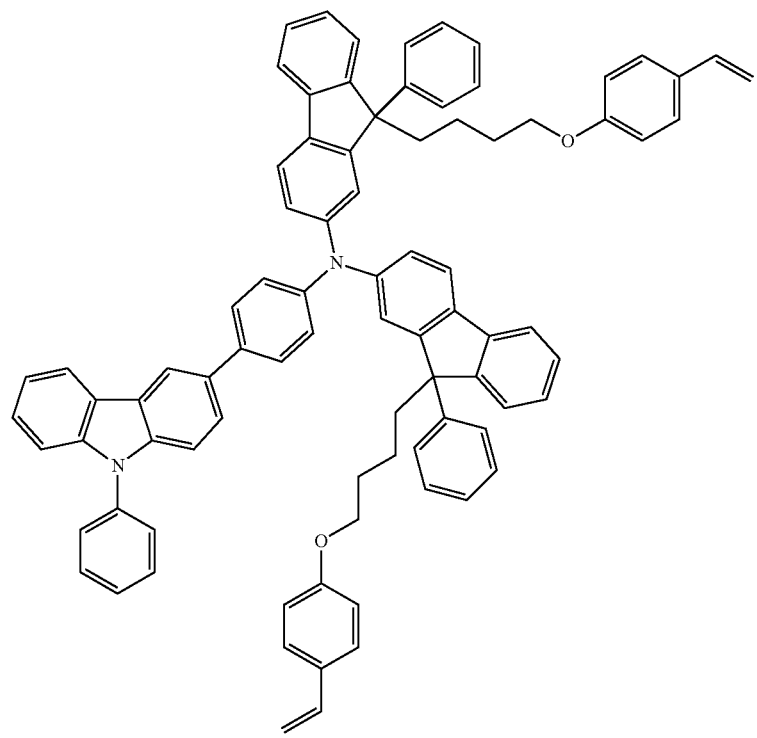

-continued
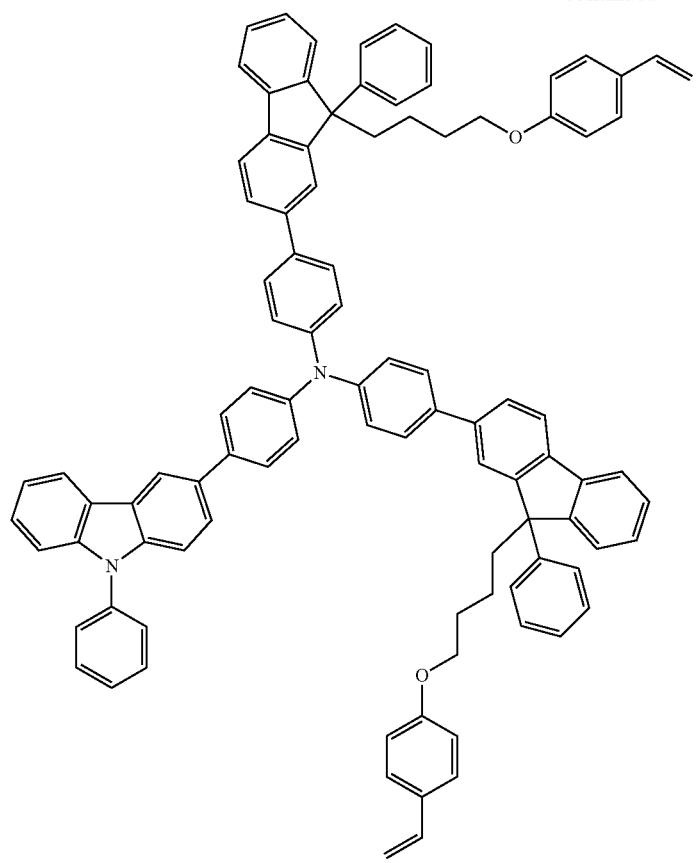
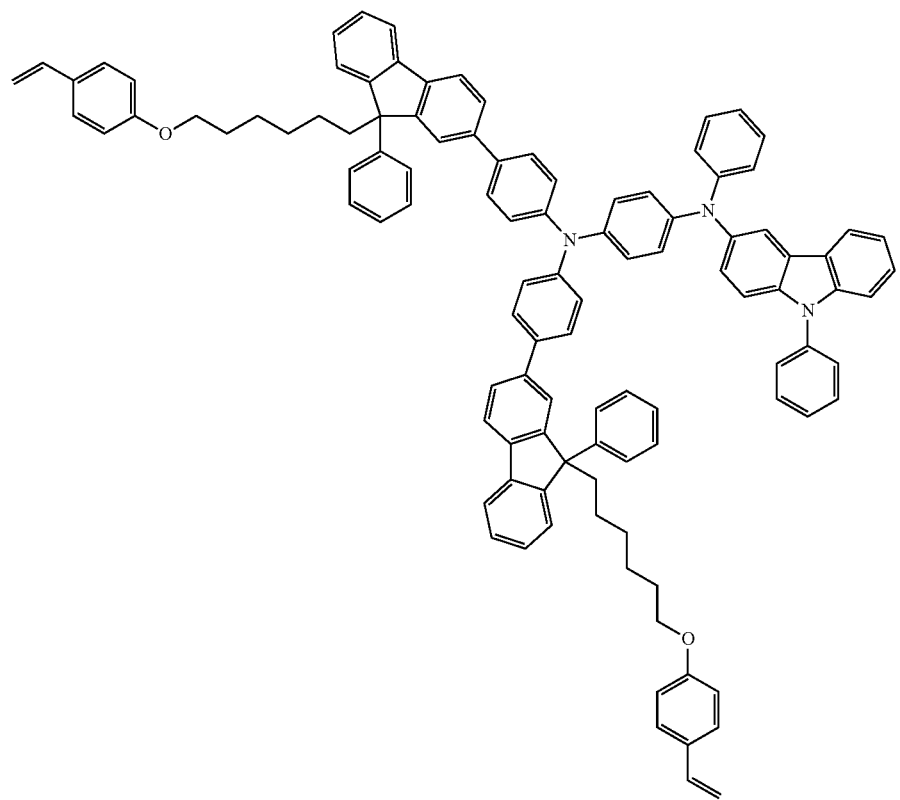

-continued
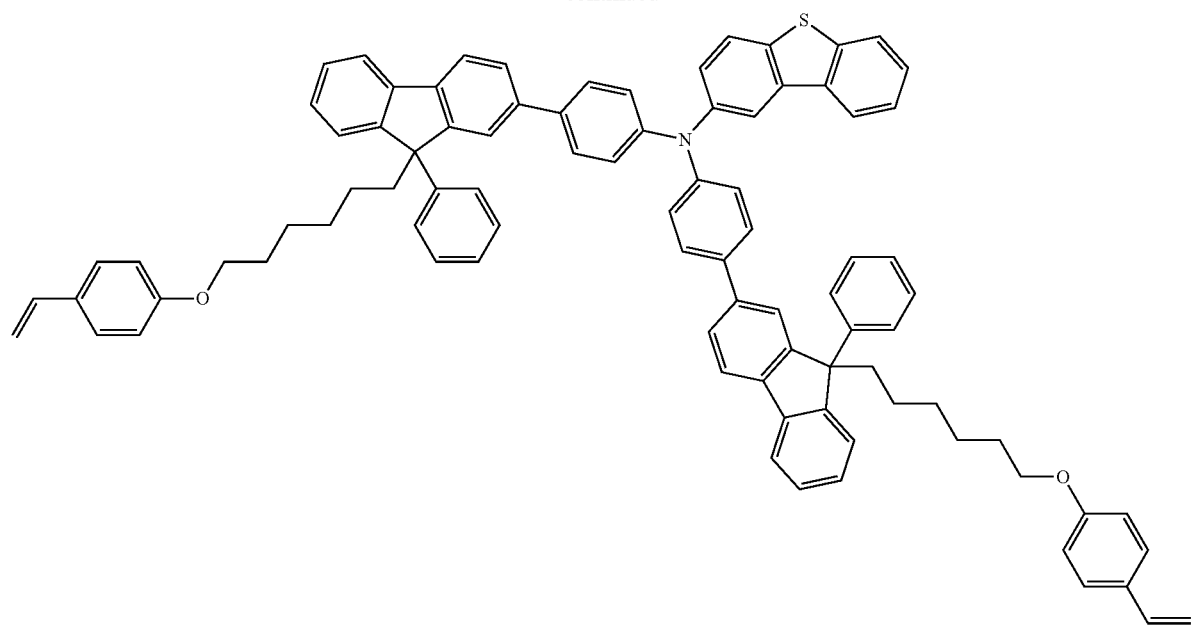
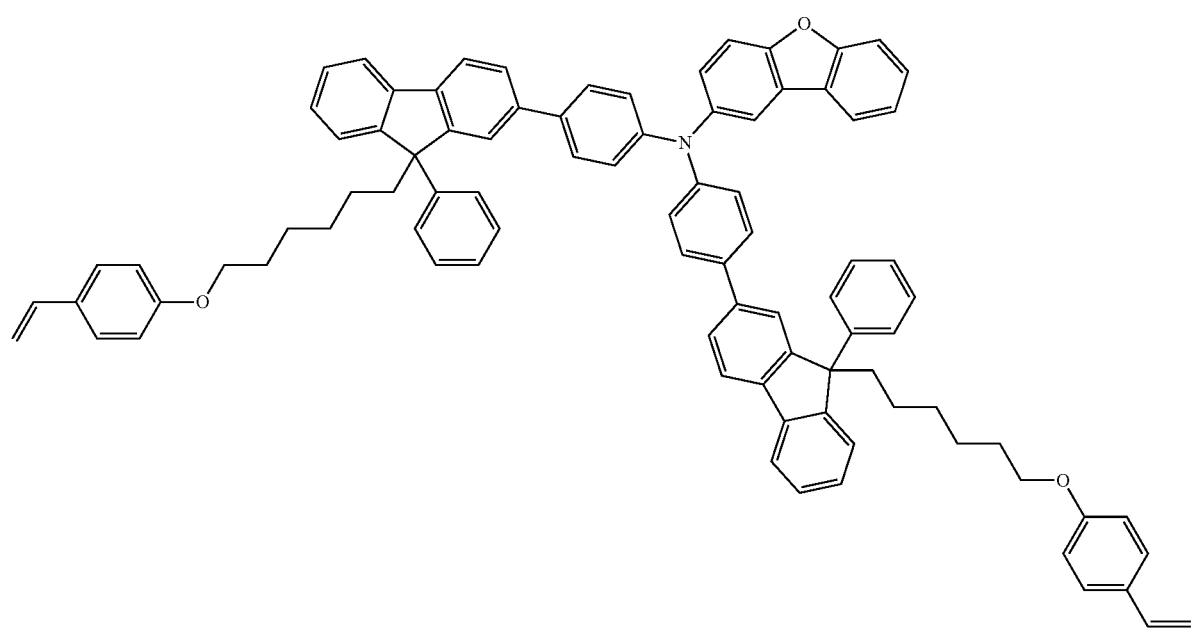

-continued
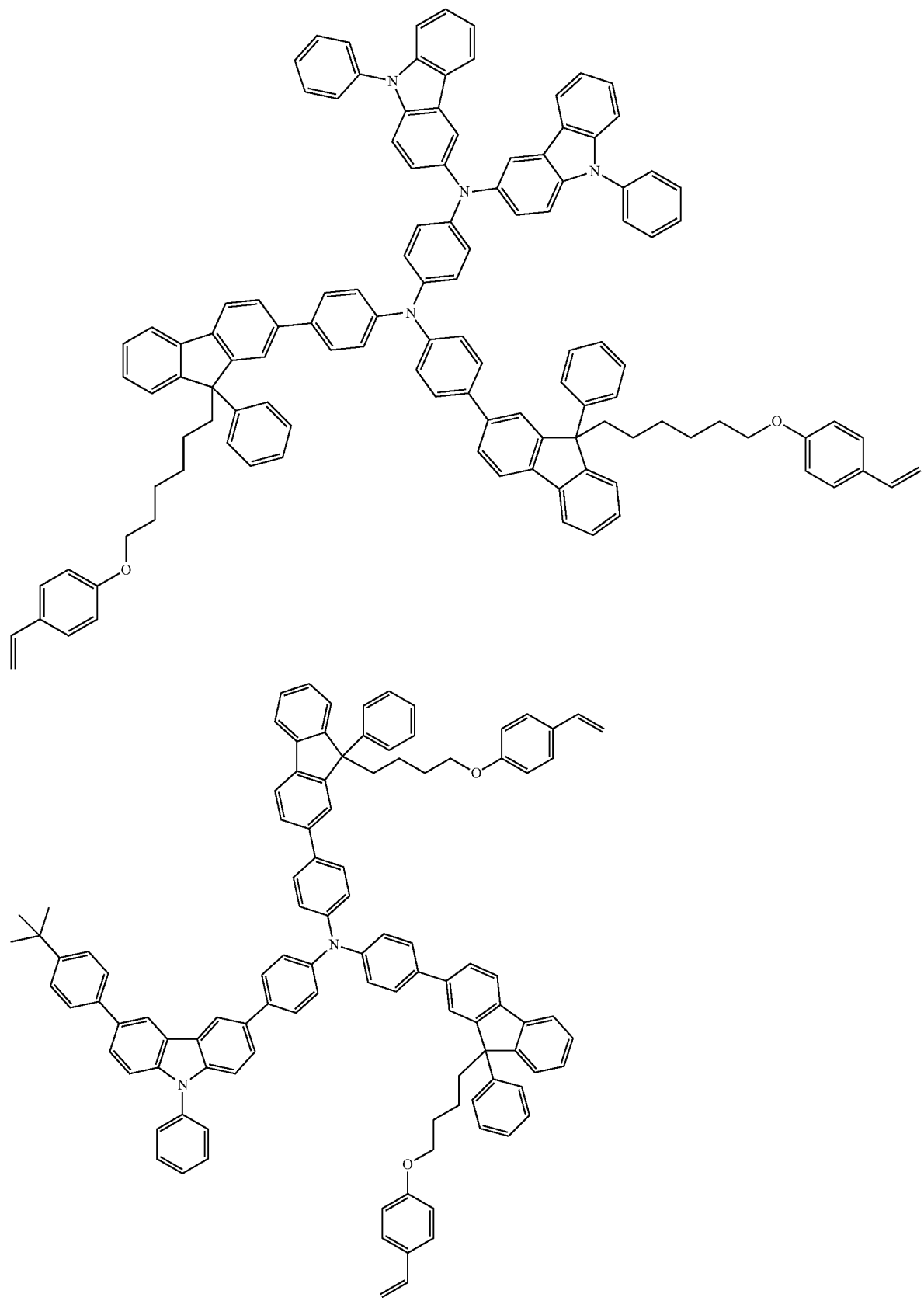

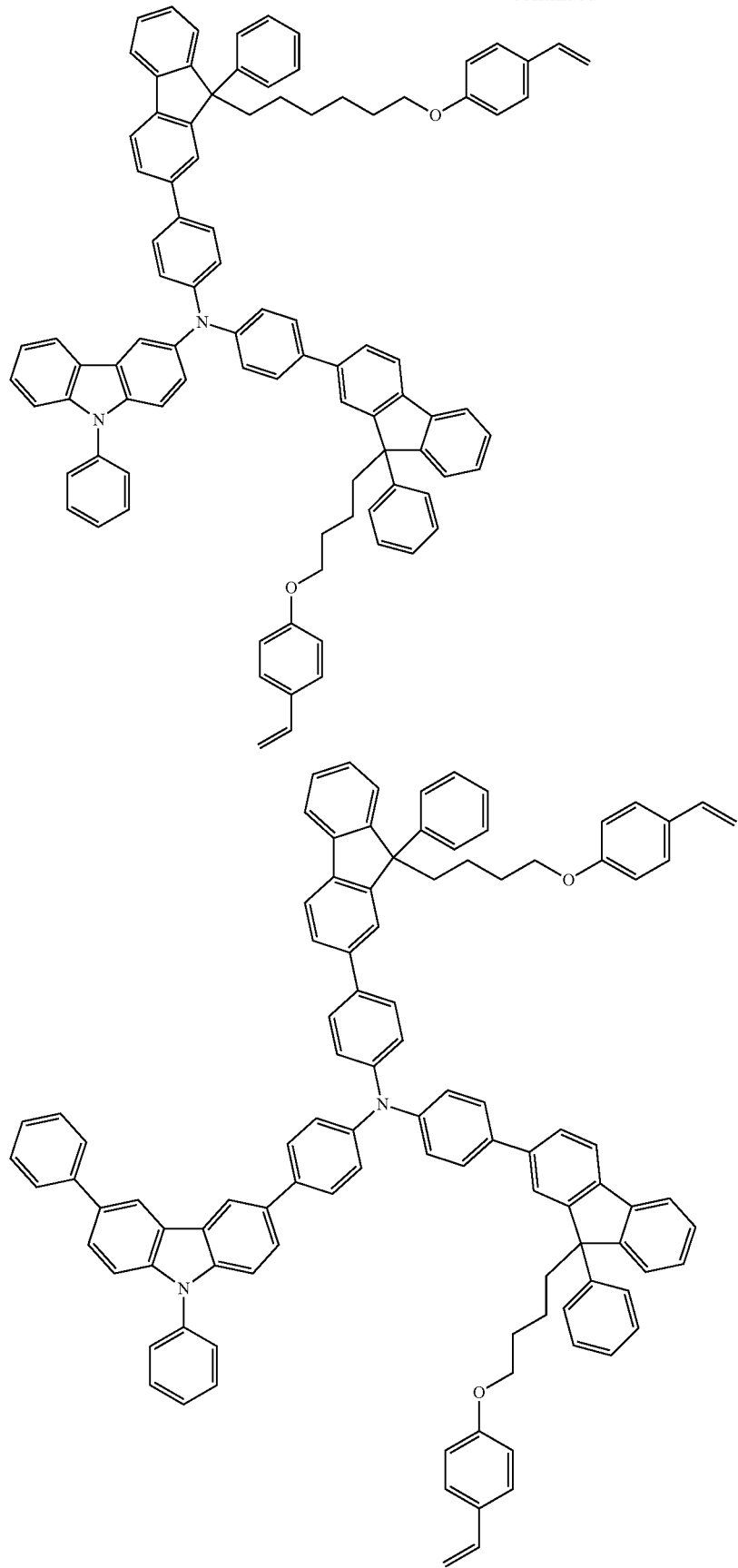

-continued
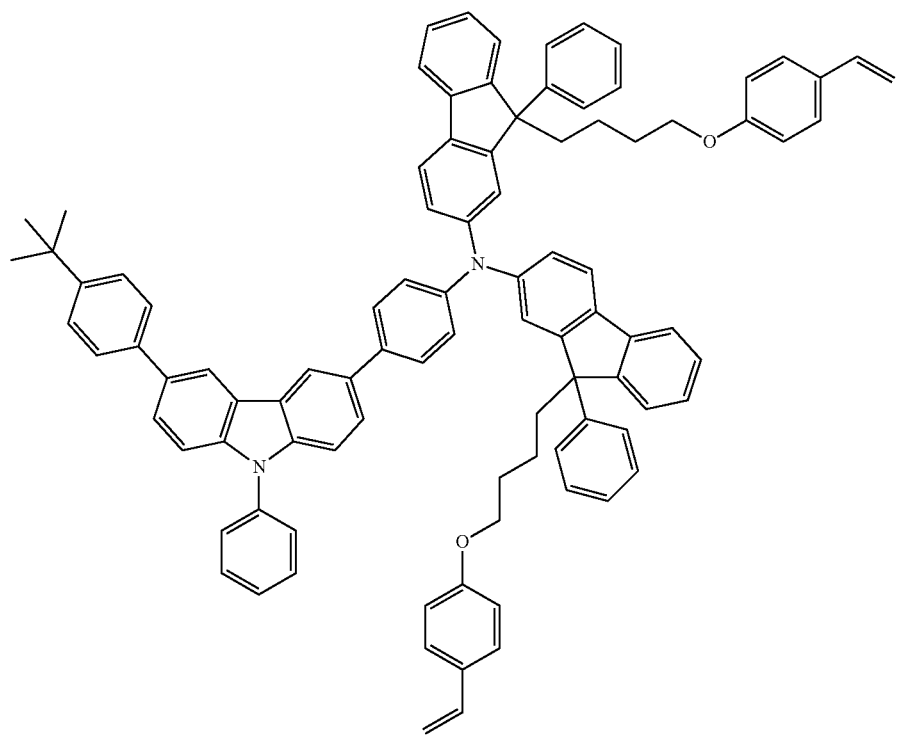
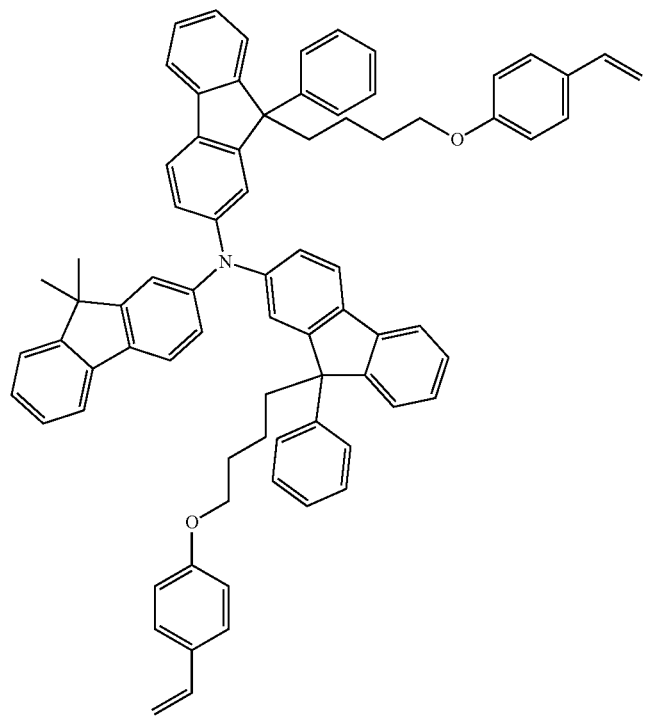

-continued
117
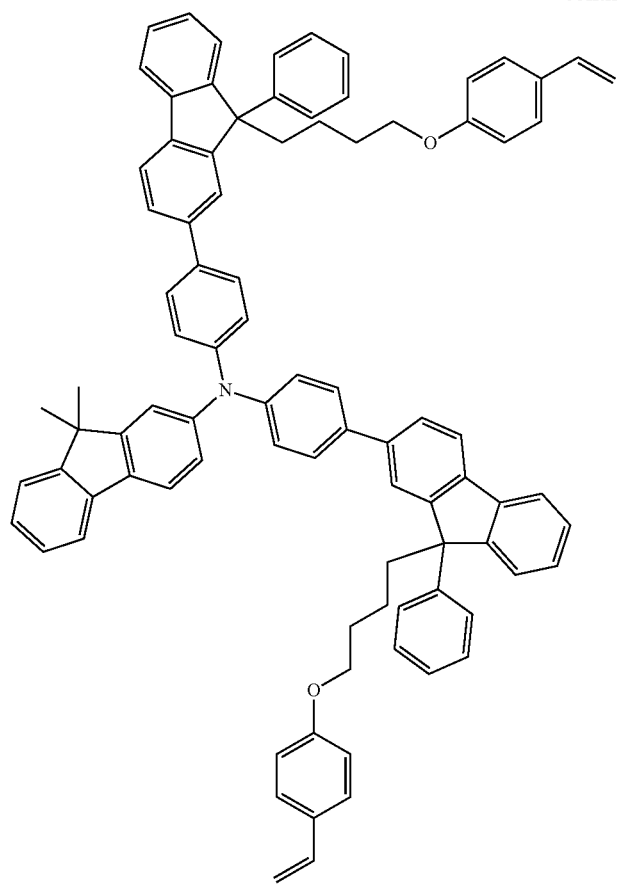
118
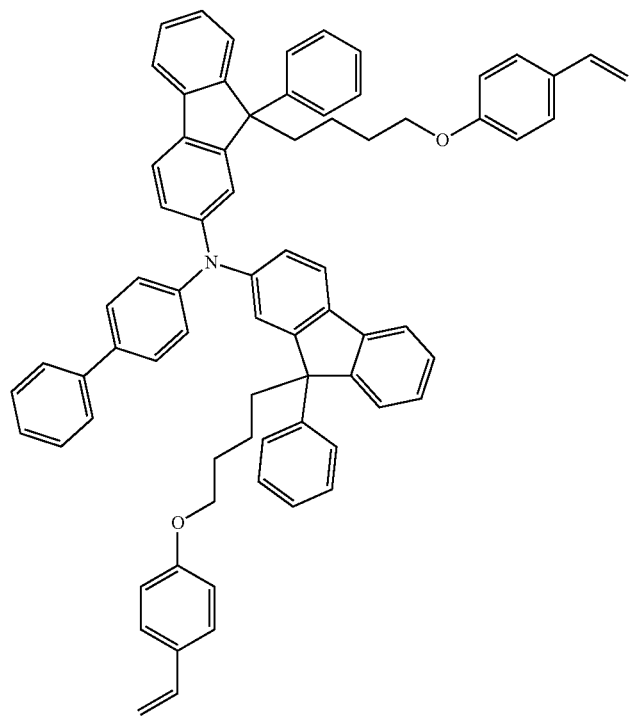

-continued
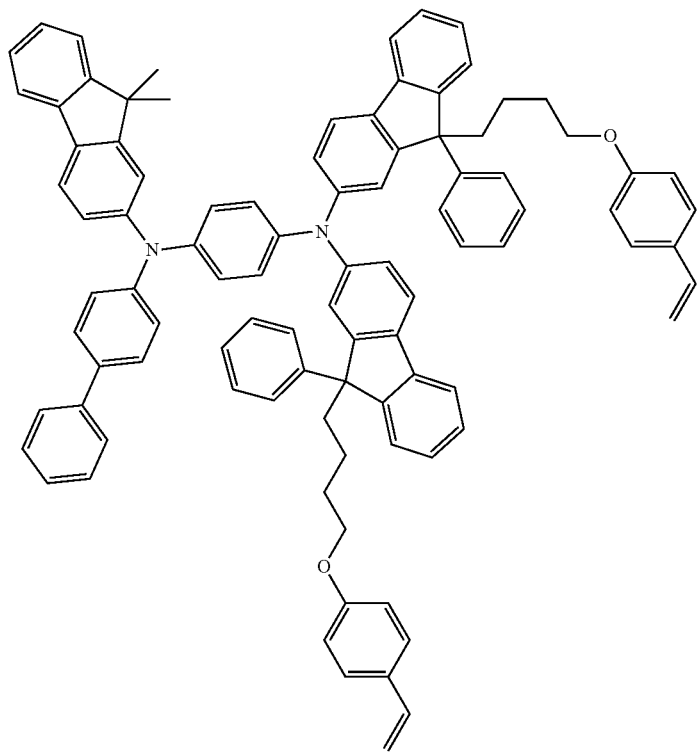
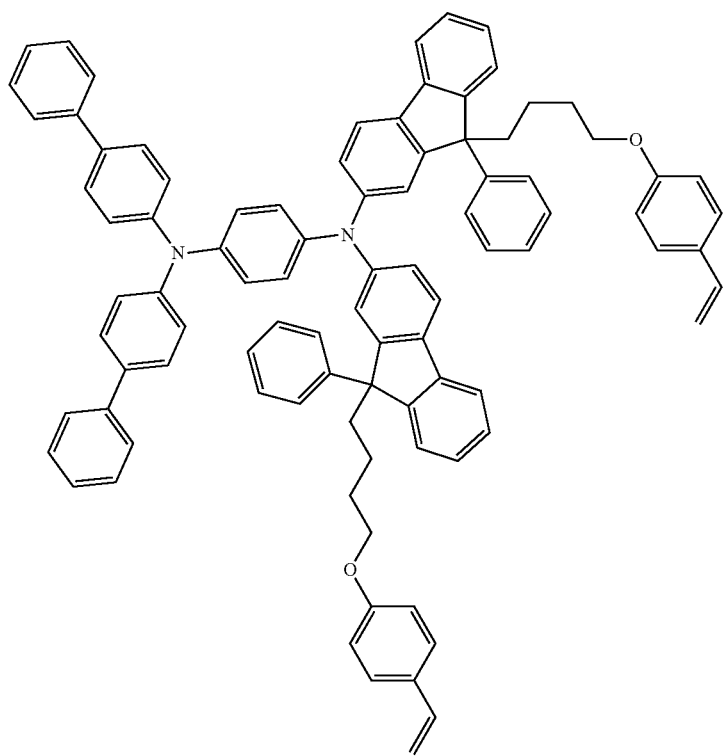

-continued
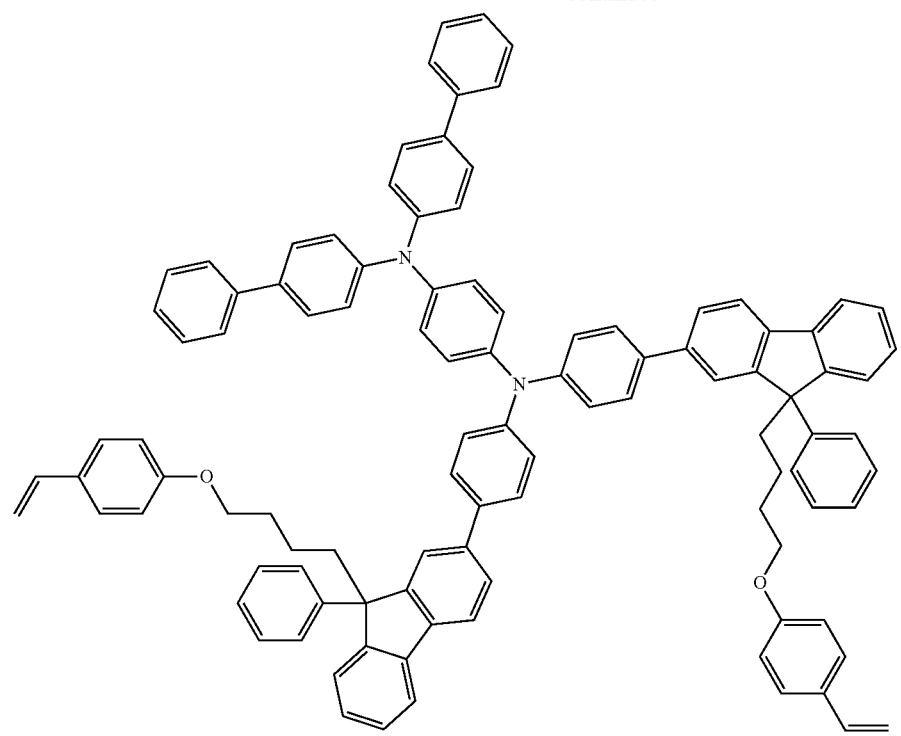
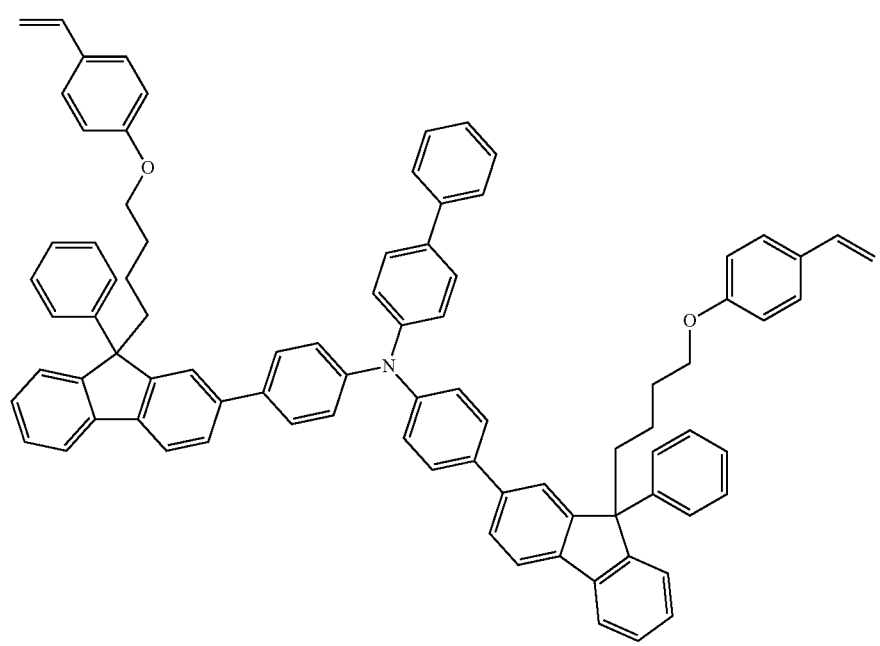

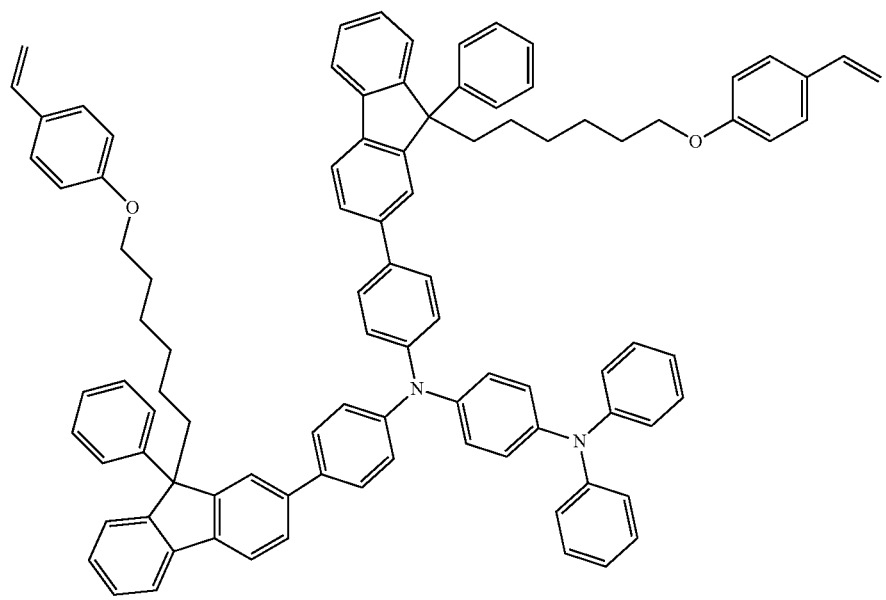
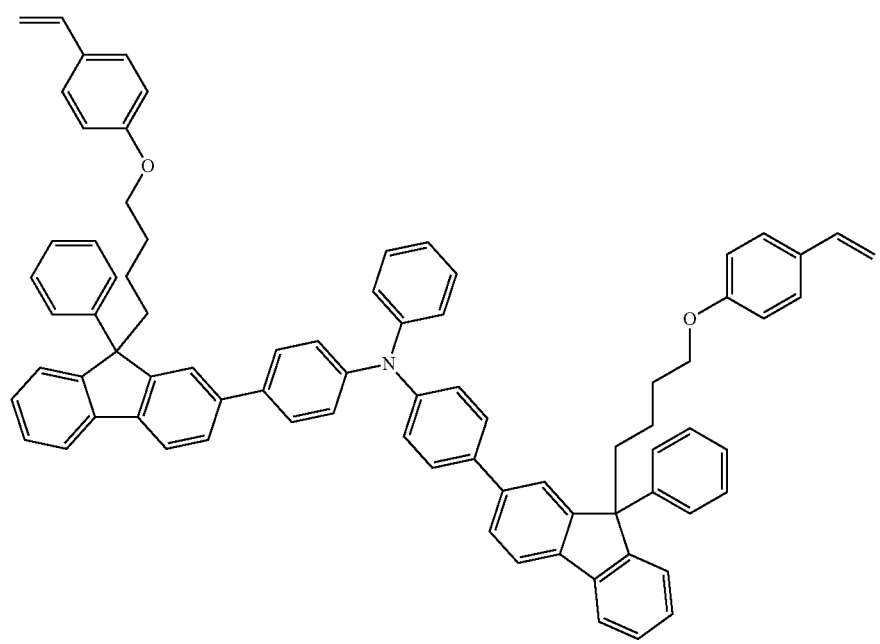

-continued
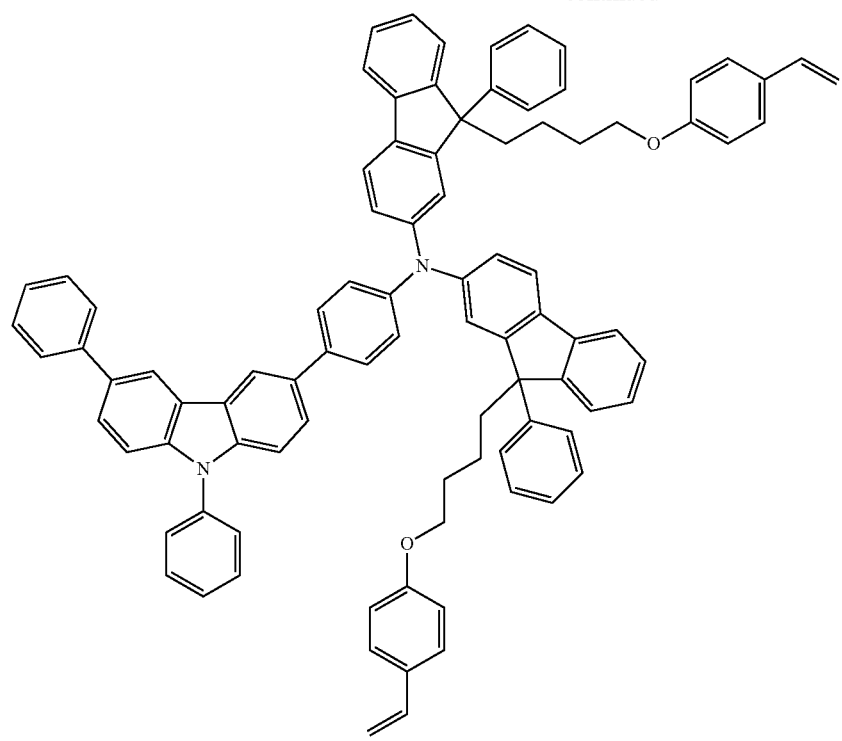
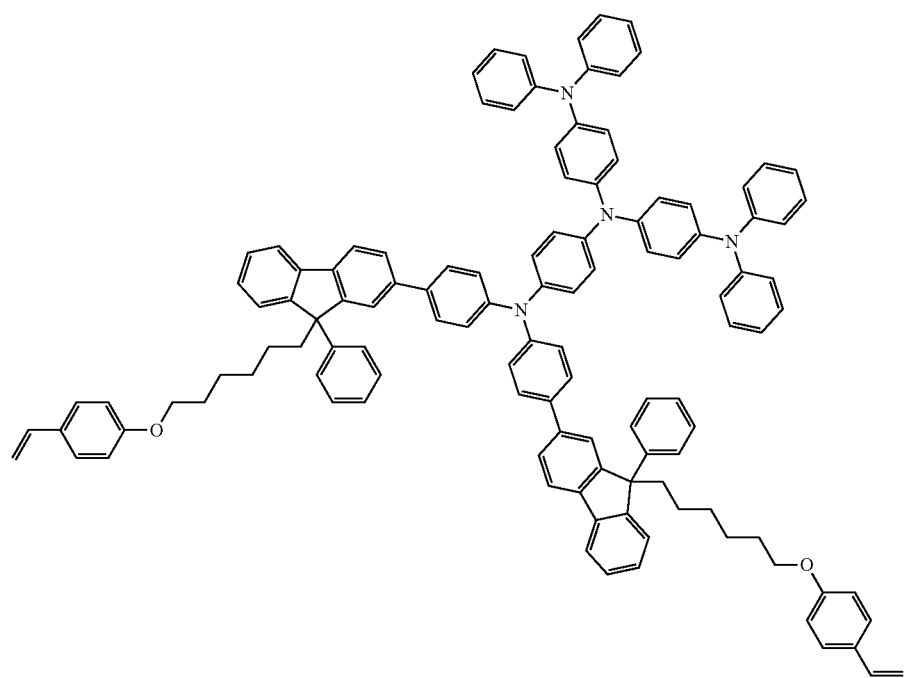

-continued
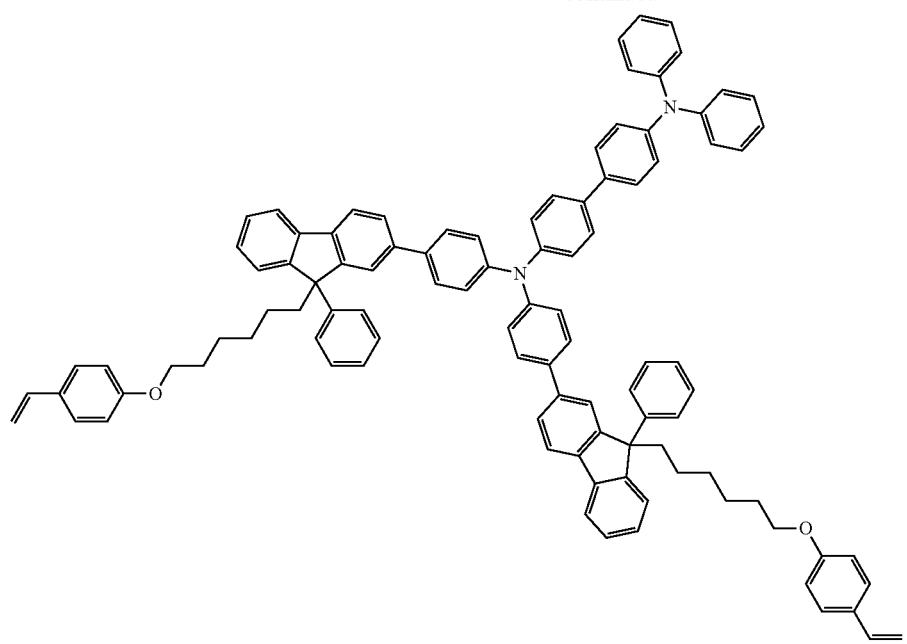 [SMILES: C=Cc1ccc(OCCCCCCC2(c3ccccc3)c3ccccc3-c3ccc(-c4ccc(N(c5ccc(-c6ccc(N(c7ccccc7)c7ccccc7)cc6)cc5)c5ccc(-c6ccc7c(c6)C(CCCCCCOc6ccc(C=C)cc6)(c6ccccc6)c6ccccc6-7)cc5)cc4)cc32)cc1]
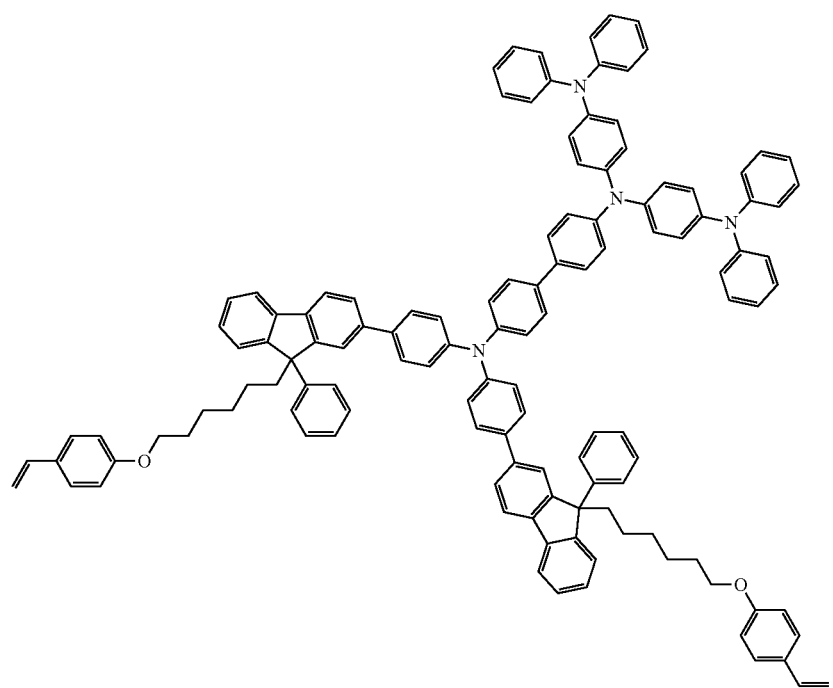 [SMILES: C=Cc1ccc(OCCCCCCC2(c3ccccc3)c3ccccc3-c3ccc(-c4ccc(N(c5ccc(-c6ccc(N(c7ccc(N(c8ccccc8)c8ccccc8)cc7)c7ccc(N(c8ccccc8)c8ccccc8)cc7)cc6)cc5)c5ccc(-c6ccc7c(c6)C(CCCCCCOc6ccc(C=C)cc6)(c6ccccc6)c6ccccc6-7)cc5)cc4)cc32)cc1]

-continued

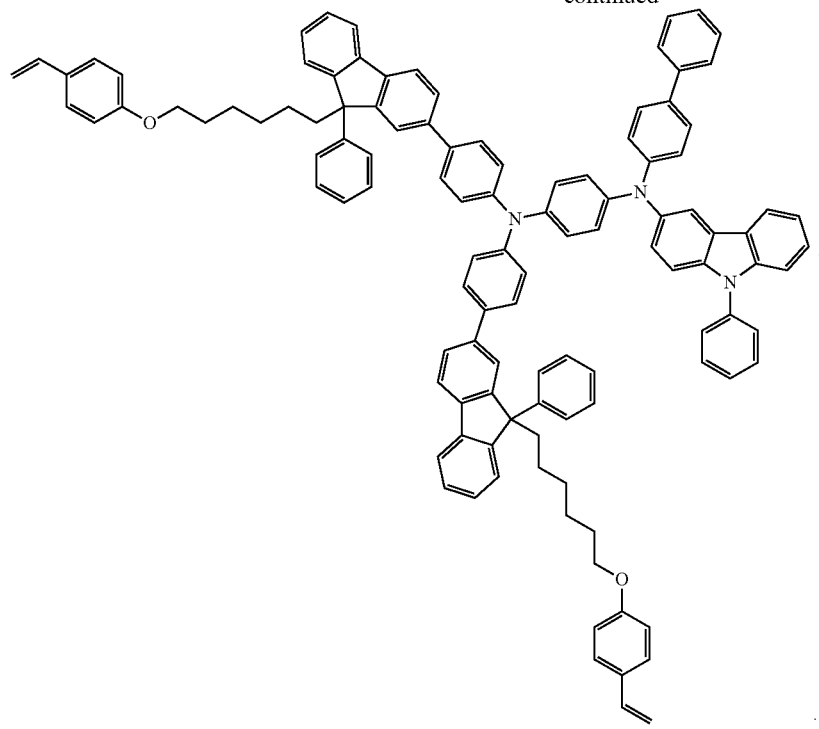

6. A coating composition comprising the compound of claim 1.

7. The coating composition of claim 6, further comprising a p-doping material.

8. The coating composition of claim 6, which has viscosity of 2 cP to 15 cP.

9. An organic light emitting device comprising:
a cathode;
an anode; and
one or more organic material layers provided between the cathode and the anode,
wherein one or more layers of the organic material layers comprise a cured coating composition of claim 6; and
the cured coating composition is in a cured state by heat treating or light treating the coating composition.

10. The organic light emitting device of claim 9, wherein the organic material layer comprising the cured material of the coating composition is a hole transfer layer, a hole injection layer, or a layer carrying out hole transfer and hole injection at the same time.

11. A method for manufacturing an organic light emitting device comprising:

preparing a substrate;
forming a cathode or an anode on the substrate;
forming one or more organic material layers on the cathode or the anode; and
forming an anode or a cathode on the organic material layer,
wherein the forming of organic material layers comprises forming one or more organic material layers using the coating composition of claim 6.

12. The method for manufacturing an organic light emitting device of claim 11, wherein the organic material layer formed using the coating composition is formed using spin coating.

13. The method for manufacturing an organic light emitting device of claim 11, wherein the forming of organic material layers formed using the coating composition includes coating the coating composition on the cathode or the anode; and heat treating or light treating the coated coating composition.

* * * * *